US008940185B2

(12) United States Patent
Tanaka

(10) Patent No.: US 8,940,185 B2
(45) Date of Patent: Jan. 27, 2015

(54) LIQUID CRYSTAL COMPOUND, LIQUID CRYSTAL COMPOSITION AND LIQUID CRYSTAL DISPLAY DEVICE

(75) Inventor: Hiroyuki Tanaka, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 0 days.

(21) Appl. No.: 13/520,343

(22) PCT Filed: Dec. 20, 2010

(86) PCT No.: PCT/JP2010/072903

§ 371 (c)(1), (2), (4) Date: Jul. 3, 2012

(87) PCT Pub. No.: WO2011/083677

PCT Pub. Date: Jul. 14, 2011

(65) Prior Publication Data

US 2013/0119310 A1 May 16, 2013

(30) Foreign Application Priority Data

Jan. 6, 2010 (JP) ................................ 2010-001036

(51) Int. Cl.

| | |
|---|---|
| ***C09K 19/06*** | (2006.01) |
| ***C09K 19/52*** | (2006.01) |
| ***C09K 19/34*** | (2006.01) |
| ***C09K 19/32*** | (2006.01) |
| ***C09K 19/12*** | (2006.01) |
| ***C07D 239/00*** | (2006.01) |
| ***C07D 315/00*** | (2006.01) |
| ***C07D 211/72*** | (2006.01) |
| ***C07C 41/00*** | (2006.01) |
| ***C07C 19/08*** | (2006.01) |
| ***C09K 19/16*** | (2006.01) |
| ***C07C 25/24*** | (2006.01) |
| ***C09K 19/30*** | (2006.01) |
| *C09K 19/04* | (2006.01) |

(52) U.S. Cl.

CPC ................. *C09K 19/16* (2013.01); *C07C 25/24* (2013.01); *C09K 19/3048* (2013.01); *C09K 19/3402* (2013.01); *C09K 19/3444* (2013.01); *C09K 19/3458* (2013.01); *C09K 19/32* (2013.01); *C09K 19/3447* (2013.01); *C09K 2019/0459* (2013.01); *C09K 2019/3422* (2013.01)

USPC .............. 252/299.6; 252/299.01; 252/299.61; 252/299.62; 252/299.66; 428/1.1; 544/242; 546/346; 570/128; 568/661; 549/369; 549/428

(58) Field of Classification Search

USPC ............... 252/299.01, 299.6, 299.61, 299.62, 252/299.66; 544/242; 546/346; 549/369, 549/428; 570/128; 568/661

See application file for complete search history.

(56) References Cited

U.S. PATENT DOCUMENTS

| | | | | |
|---|---|---|---|---|
| 5,516,949 | A * | 5/1996 | Shinya et al. | 570/128 |
| 5,663,463 | A * | 9/1997 | Shinya et al. | 570/128 |
| 5,914,071 | A * | 6/1999 | Shinya et al. | 252/299.63 |
| 6,565,932 | B2 | 5/2003 | Iwamatsu et al. | |
| 7,732,022 | B2 * | 6/2010 | Klasen-Memmer et al. | 428/1.1 |

FOREIGN PATENT DOCUMENTS

| | | | |
|---|---|---|---|
| DE | 102006023898 | A1 * | 12/2006 |
| GB | 1215270 | | 12/1970 |
| JP | 03-041037 | | 2/1991 |
| JP | 03-294386 | | 12/1991 |
| JP | 06-025030 | | 2/1994 |
| JP | 06-040967 | | 2/1994 |
| JP | 06-329566 | | 11/1994 |
| JP | 07-126199 | | 5/1995 |
| JP | 07-133241 | | 5/1995 |
| JP | 07-165635 | | 6/1995 |
| JP | 10-109953 | | 4/1998 |
| WO | 2006/133783 | | 12/2006 |

* cited by examiner

*Primary Examiner* — Geraldina Visconti
(74) *Attorney, Agent, or Firm* — Jianq Chyun IP Office

(57) ABSTRACT

To provide a novel liquid crystal compound having general physical properties necessary for the compound, namely, stability to heat, light and so forth, a wide temperature range of a liquid crystal phase, a high clearing point, a good compatibility with other compounds, a large refractive index anisotropy, a large dielectric anisotropy and a small viscosity. The liquid crystal compound is provided as compound (1):

(1)

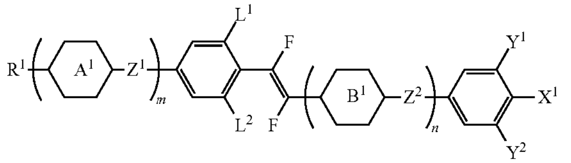

wherein, for example, $R^1$ is alkyl having 1 to 20 carbons; ring $A^1$ and ring $B^1$ are 1,4-cyclohexylene or 1,4-phenylene; $Z^1$ and $Z^2$ are a single bond, —$CH_2CH_2$—, —CH═CH— or —C≡C—; $L^1$ is fluorine; $L^2$, $Y^1$ and $Y^2$ are hydrogen, fluorine or chlorine; and $X^1$ is halogen, —C≡N or alkyl having 1 to 10 carbons, and in the alkyl, arbitrary —$CH_2$— may be replaced by —O— or —S—, and m is 1 and n is 0.

18 Claims, No Drawings

LIQUID CRYSTAL COMPOUND, LIQUID CRYSTAL COMPOSITION AND LIQUID CRYSTAL DISPLAY DEVICE

CROSS-REFERENCE TO RELATED APPLICATION

This application is a 371 of international application of PCT application serial no. PCT/JP2010/072903, filed on Dec. 20, 2010, which claims the priority benefit of Japan application no. 2010-001036, filed on Jan. 6, 2010. The entirety of each of the above-mentioned patent applications is hereby incorporated by reference herein and made a part of this specification.

TECHNICAL FIELD

The invention relates to a novel liquid crystal compound, liquid crystal composition and liquid crystal display device. More specifically, the invention relates to a liquid crystal compound having a wide temperature range of liquid crystal phases, a high clearing point, a good compatibility with other compounds, a large refractive index anisotropy, a large dielectric anisotropy and a small viscosity, and a liquid crystal composition containing the compound. A liquid crystal display device using the composition can be used in a wide temperature range, can be driven at a low voltage, and can obtain a large contrast ratio and steep electrooptical characteristics.

BACKGROUND ART

A display device using a liquid crystal compound has been widely used for a display for a watch, a calculator, a personal computer and so forth. The display devices utilize a refractive index anisotropy, a dielectric anisotropy and so forth of the liquid crystal compound.

In a liquid crystal display device, a classification based on an operating mode for liquid crystals includes a phase change (PC), twisted nematic (TN), super twisted nematic (STN), bistable twisted nematic (BTN), electrically controlled birefringence (ECB), optically compensated bend (OCB), in-plane switching (IPS), vertical alignment (VA) and polymer sustained alignment (PSA) mode. A classification based on a driving mode of a device includes passive matrix (PM) and active matrix (AM). The passive matrix (PM) is classified into static, multiplex and so forth, and the AM is classified into thin film transistor (TFT), metal insulator metal (MIM) and so forth.

The liquid crystal display device contains a liquid crystal composition having suitable physical properties. In order to improve characteristics of the device, the composition preferably has the suitable physical properties. General physical properties necessary for the liquid crystal compound being a component of the composition are as follows:

(1) being chemically stable and physically stable;

(2) having a high clearing point (clearing point: a phase transition temperature between a liquid crystal phase and an isotropic phase);

(3) having a low minimum temperature of liquid crystal phases (a nematic phase, a smectic phase or the like), in particular, a low minimum temperature of the nematic phase;

(4) having an excellent compatibility with other compounds;

(5) having a large dielectric anisotropy;

(6) having a large refractive index anisotropy; and (7) having a small viscosity When a composition containing a liquid crystal compound being chemically and physically stable as described in property (1) is used for the display device, a voltage holding ratio can be increased.

Because a composition containing a compound having a high clearing point or a low minimum temperature of liquid crystal phases as described in property (2) or (3) has a wide temperature range of the nematic phase, the device can be used in a wide temperature range.

In order to develop characteristics that are difficult to be output by a single compound, the liquid crystal compound is generally used in the form of the liquid crystal composition prepared by mixing with a number of other liquid crystal compounds. Accordingly, the liquid crystal compound to be used for the device preferably has a good compatibility with other compounds as described in property (4).

The liquid crystal display device having an excellent display performance in contrast, display capacity, response time characteristics and so forth has been required in recent years. For example, in order to decrease a driving voltage of the device, a liquid crystal compound allowing a decrease of a threshold voltage of the composition is required.

As is well known, the threshold voltage ($V_{th}$) is represented by the following equation (see H. J. Deuling et al., Mol. Cryst. Liq. Cryst., 27, 81 (1975)):

$$V_{th}=\pi(K/\epsilon_0\Delta\epsilon)^{1/2}$$

wherein, in the formula, K is an elastic constant and $\epsilon_0$ is a dielectric constant of vacuum. As is understood from the equation, in order to decrease the threshold voltage ($V_{th}$), two ways are conceivable, in which the dielectric anisotropy ($\Delta\epsilon$) is increased or the elastic constant (K) is decreased. However, the elastic constant is not easily controlled with the present art. Therefore, a compound having a large dielectric anisotropy is ordinarily used to respond to a demand. Under such circumstances, the liquid crystal compound having the large dielectric anisotropy as described in property (5) has been actively developed.

Furthermore, in order to obtain a good display performance, a thickness of a cell of the liquid crystal display device for constituting the display performance, and a value of refractive index anisotropy ($\Delta n$) of the composition to be used are preferably constant (see E. Jakeman et al., Phys. Lett., 39A., 69 (1972)). Moreover, a response speed of the device is inversely proportional to a square of the thickness of the cell to be used. Therefore, in order to manufacture a device that can be applied to displaying moving images and so forth and also can respond at a high speed, a composition having a large refractive index anisotropy should be used. Accordingly, the liquid crystal compound having the large refractive index anisotropy as described in property (6) has been required.

Moreover, the response speed of the device is correlated with viscosity of the liquid crystal composition. Therefore, in order to manufacture the device that can respond at a high speed, a composition having a small viscosity should be used. Accordingly, the liquid crystal compound having the small viscosity as described in property (7) has been required.

As the liquid crystal compound having the large dielectric anisotropy, the large refractive index anisotropy and the small viscosity, a variety of difluorostilbene derivatives having a positive dielectric anisotropy have been prepared so far. For example, Patent literatures Nos. 1 to 6 show two-ring compounds. However, the compounds have an insufficiently high clearing point. Thus, when the compounds are combined into the composition, a temperature range in which the composition is used as the device is insufficiently wide.

Moreover, Patent literatures Nos. 3 to 6 show three-ring compounds, and Patent literature No. 4 shows compound (S-1), compound (S-2) and so forth. However, the compounds have an insufficiently large dielectric anisotropy, and furthermore compatibility with other compounds are insufficient in many cases.

(S-1)

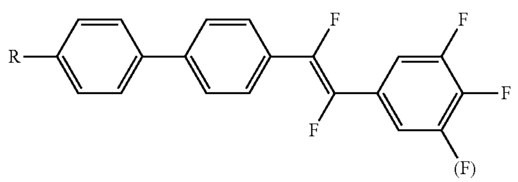

(S-2)

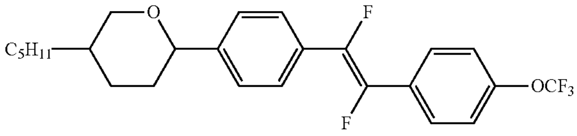

CITATION LIST

Patent Literature

Patent literature No. 1: JP H6-329566 A.

Patent literature No. 2: GB 1215270 B.

Patent literature No. 3: U.S. Pat. No. 6,565,932B.

Patent literature No. 4: WO 2006/133783 A.

Patent literature No. 5: JP 2598830 B.

Patent literature No. 6: JP 2505907 B.

SUMMARY OF INVENTION

Technical Problem

A first aim of the invention is to provide a liquid crystal compound having general physical properties necessary for the compound, namely, stability to heat, light and so forth, a wide temperature range of liquid crystal phases, a high clearing point, a good compatibility with other compounds, a large refractive index anisotropy, a large dielectric anisotropy and a small viscosity. A second aim is to provide a liquid crystal composition that contains the compound and has a wide temperature range of a liquid crystal phase, a large refractive index anisotropy, a low threshold voltage and a small viscosity. A third aim is to provide a liquid crystal display device that contains the composition and has a wide temperature range in which the device can be used, a short response time, a small electric power consumption, a large contrast ratio and a low driving voltage.

Solution to Problem

The invention provides a liquid crystal compound, a liquid crystal composition and a liquid crystal display device containing the liquid crystal composition and so forth as described below. Moreover, in the following, preferred examples of a terminal group, a ring, a bonding group and so forth in a compound represented by formula (1) are also described.

Item 1. A compound represented by formula (1):

(1)

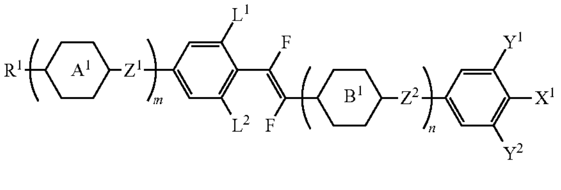

wherein, in formula (1), $R^1$ is alkyl having 1 to 20 carbons, and in the alkyl, arbitrary $—CH_2—$ may be replaced by —O— or —S—, and in the groups, arbitrary $—CH_2CH_2—$ may be replaced by —CH═CH—; ring $A^1$ is 1,4-cyclohexylene, 1,3-dioxane-2,5-diyl, tetrahydropyran-2,5-diyl, pyrimidine-2,5-diyl, pyridine-2,5-diyl, 1,4-phenylene, or 1,4-phenylene in which arbitrary hydrogen is replaced by halogen; ring $B^1$ is 1,4-phenylene, 3-fluoro-1,4-phenylene, 3,5-difluoro-1,4-phenylene, 3-chloro-1,4-phenylene or 3-chloro-5-fluoro-1,4-phenylene; $Z^1$ and $Z^2$ are independently a single bond, $—CH_2CH_2—$, —CH═CH— or —C≡C—; $L^1$, $L^2$, $Y^1$ and $Y^2$ are independently hydrogen, fluorine or chlorine; $X^1$ is hydrogen, halogen, —C≡N, —N═C═S, $—SF_5—$ or alkyl having 1 to 10 carbons, and in the alkyl, arbitrary $—CH_2—$ may be replaced by —O— or —S—, and in the groups, arbitrary $—CH_2CH_2—$ may be replaced by —CH═CH—, and arbitrary hydrogen may be replaced by halogen; m is 1 or 2; n is 0 or 1; and $L^1$ is fluorine, when m is 1 and n is 0.

Item 2. The compound according to item 1, wherein, in formula (1), $R^1$ is alkyl having 1 to 20 carbons, alkenyl having 2 to 20 carbons, alkoxy having 1 to 19 carbons, alkenyloxy having 2 to 19 carbons or alkylthio having 1 to 19 carbons; and $X^1$ is hydrogen, halogen, —C≡N, —N═C═S, $—SF_5$, alkyl having 1 to 10 carbons, alkenyl having 2 to 10 carbons, alkoxy having 1 to 9 carbons, alkenyloxy having 2 to 9 carbons, thioalkyl having 2 to 9 carbons, $—CH_2F$, $—CHF_2$, $—CF_3$, $—(CH_2)_2—F$, $—CF_2CH_2F$, $—CF_2CHF_2$, $—CH_2CF_3$, $—CF_2CF_3$, $—(CH_2)_3—F$, $—(CF_2)_3—F$, $—CF_2CHFCF_3$, $—CHFCF_2CF_3$, $—(CH_2)_4—F$, $—(CF_2)_4—F$, $—(CH_2)_5—F$, $—(CF_2)_5—F$, $—OCH_2F$, $—OCHF_2$, $—OCF_3$, $—O—(CH_2)_2—F$, $—OCF_2CH_2F$, $—OCF_2CHF_2$, $—OCH_2CF_3$, $—O—(CH_2)_3—F$, $—O—(CF_2)_3—F$, $—OCF_2CHFCF_3$, $—OCHFCF_2CF_3$, $—O(CH_2)_4—F$, $—O—(CF_2)_4—F$, $—O—(CH_2)_5—F$, $—O—(CF_2)_5—F$, —CH═CHF, $—CH═CF_2$, —CF═CHF, $—CH═CHCH_2F$, $—CH═CHCF_3$, $—(CH_2)_2—CH═CF_2$, $—CH_2CH═CHCF_3$ or $—CH═CHCF_2CF_3$.

Item 3. The compound according to item 1, wherein, in formula (1), $R^1$ is alkyl having 1 to 12 carbons, alkenyl having 2 to 12 carbons, alkoxy having 1 to 12 carbons or alkenyloxy having 2 to 12 carbons, $Z^1$ and $Z^2$ are independently a single bond, $—CH_2CH_2—$ or —CH═CH—, and $X^1$ is fluorine, chlorine, $—CF_3$, $—CHF_2$, $—CH_2F$, $—OCF_3$, $—OCHF_2$ or $—OCH_2F$.

Item 4. The compound according to item 1, wherein, in formula (1), $R^1$ is alkyl having 1 to 12 carbons, alkenyl having 2 to 12 carbons or alkoxy having 1 to 12 carbons, $Z^1$ and $Z^2$ are independently a single bond or $—CH_2CH_2—$, and $X^1$ is fluorine, chlorine, $—CF_3$ or $—OCF_3$.

Item 5. The compound according to item 1, represented by any one of formula (1-1) to formula (1-4):

(1-1)

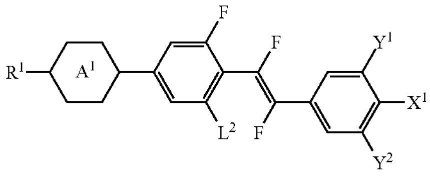

(1-2)

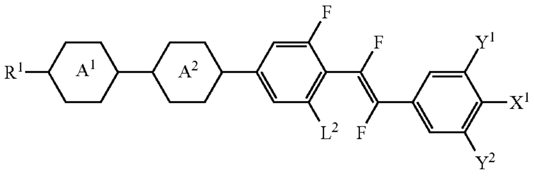

(1-3)

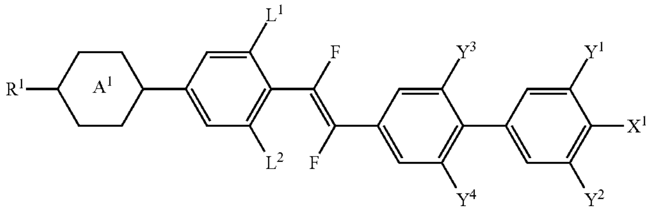

(1-4)

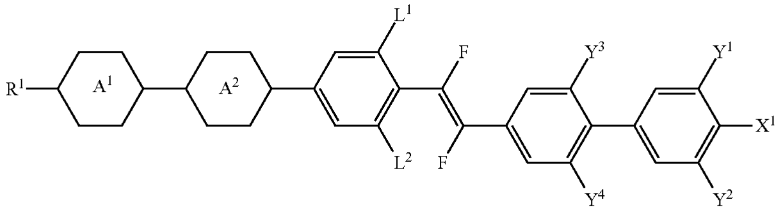

wherein, in the formulas, $R^1$ is alkyl having 1 to 12 carbons or alkenyl having 2 to 12 carbons; ring $A^1$ and ring $A^2$ are independently 1,4-cyclohexylene, 1,3-dioxane-2,5-diyl, tetrahydropyran-2,5-diyl, pyrimidine-2,5-diyl, pyridine-2,5-diyl, 1,4-phenylene, or 1,4-phenylene in which arbitrary hydrogen is replaced by halogen; $L^1$, $L^2$, $Y^1$, $Y^2$, $Y^3$ and $Y^4$ are independently hydrogen, fluorine or chlorine; and $X^1$ is fluorine, chlorine, —$CF_3$ or —$OCF_3$.

Item 6. The compound according to item 1, represented by any one of formula (1-5) to formula (1-33):

(1-5)

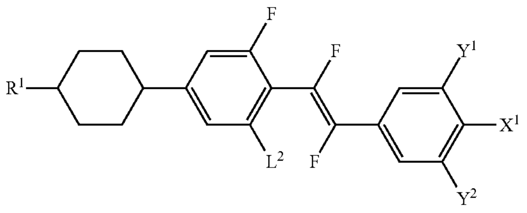

(1-6)

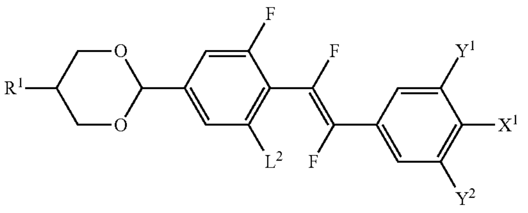

(1-7)

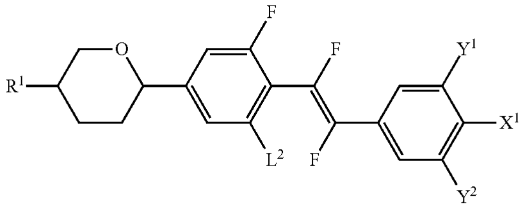

(1-8)

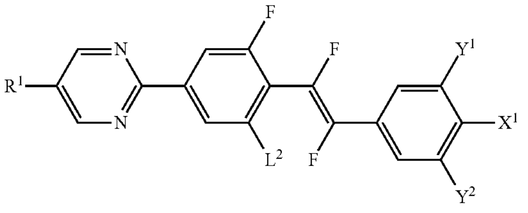

(1-9)

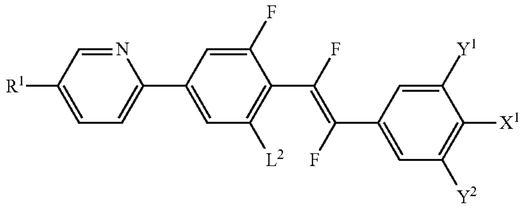

(1-10)

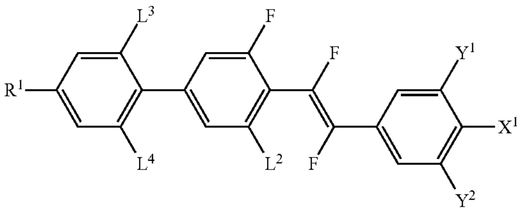

-continued
(1-11)
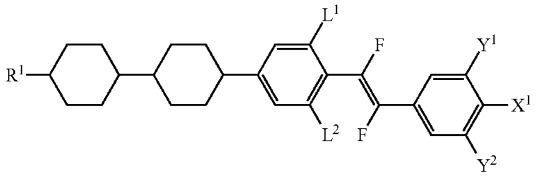
(1-12)
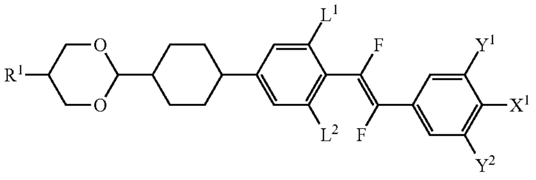
(1-13)
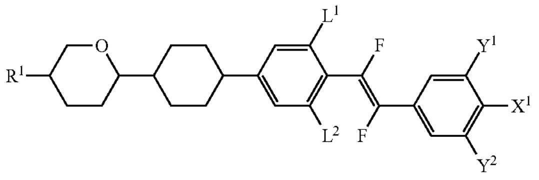
(1-14)
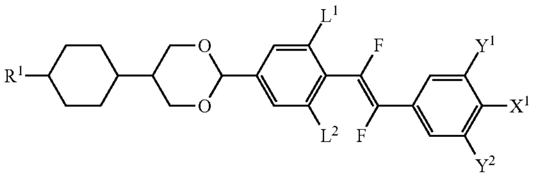
(1-15)
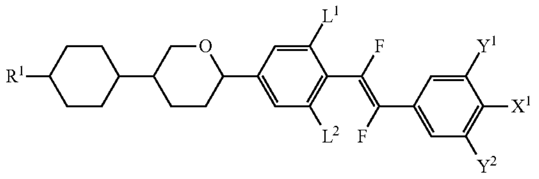
(1-16)
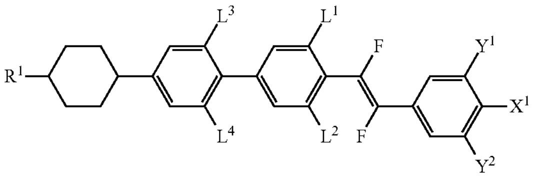
(1-17)
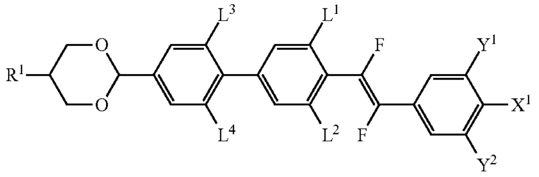
(1-18)
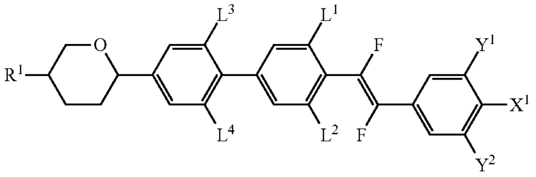
(1-19)
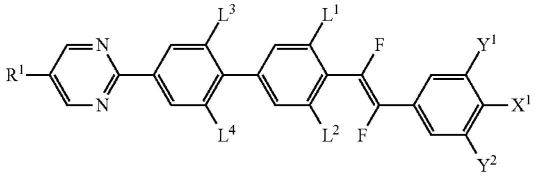
(1-20)
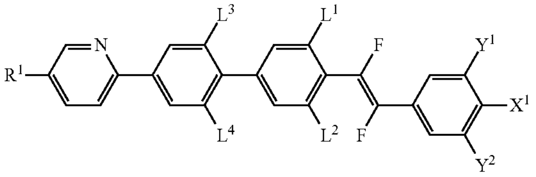
(1-21)
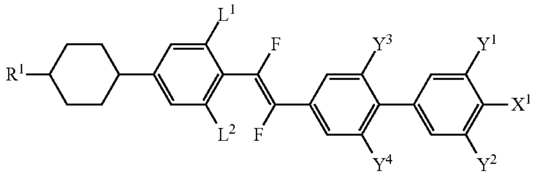
(1-22)
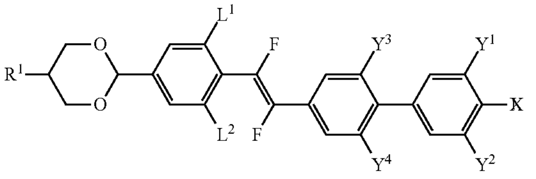
(1-23)
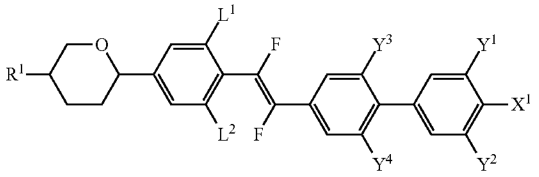
(1-24)
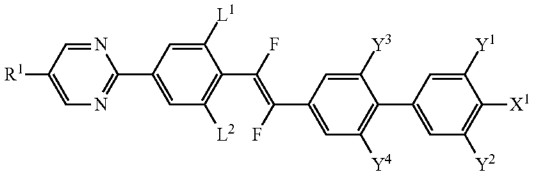

-continued
(1-25)
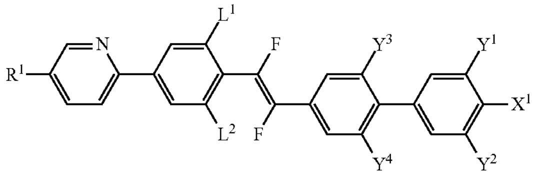
(1-26)
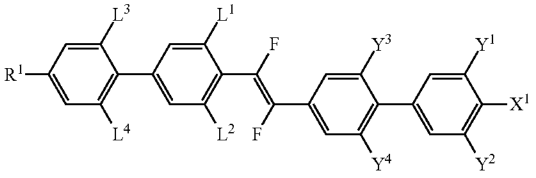
(1-27)
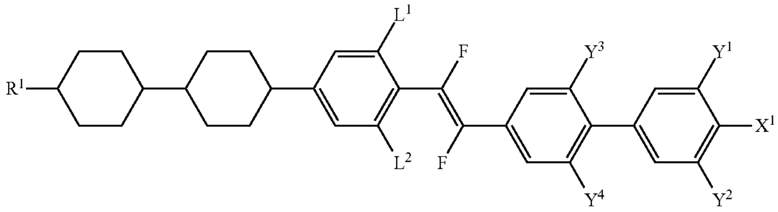
(1-28)
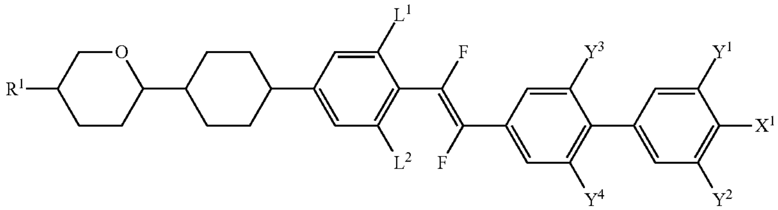
(1-29)
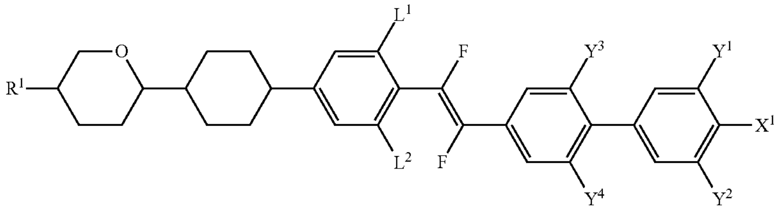
(1-30)
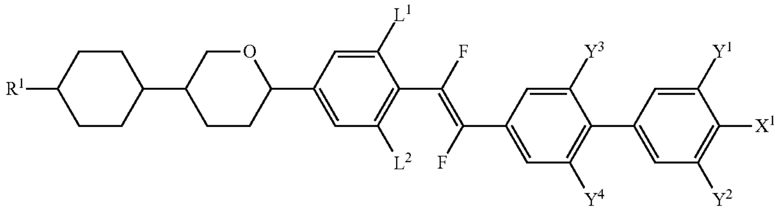
(1-31)
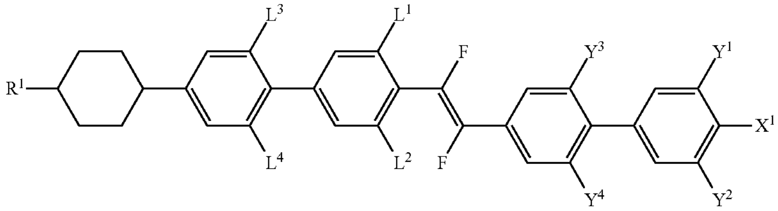
(1-32)
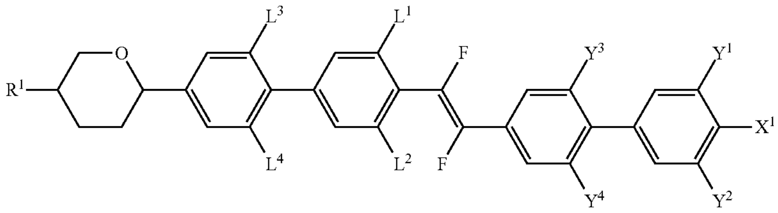

-continued (1-33)

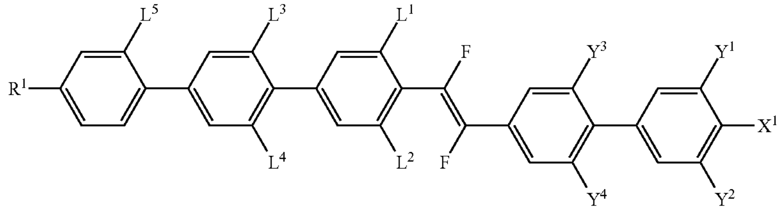

wherein, in the formulas, $R^1$ is alkyl having 1 to 12 carbons; $L^1$, $L^2$, $L^3$, $L^4$, $L^5$, $Y^1$, $Y^2$, $Y^3$ and $Y^4$ are independently hydrogen, chlorine or fluorine; and $X^1$ is fluorine, chlorine, $-CF_3$ or $-OCF_3$.

Item 7. The compound according to item 1, represented by any one of formula (1-34) to formula (1-38):

(1-34)

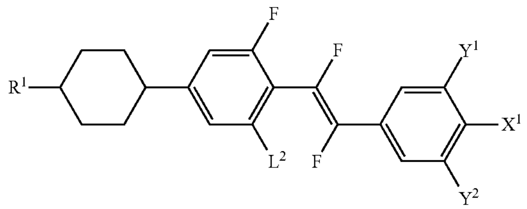

(1-35)

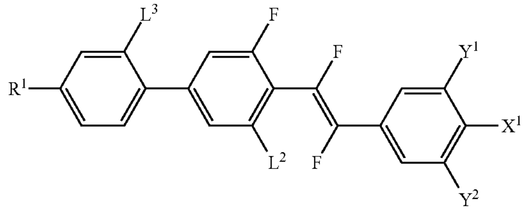

(1-36)

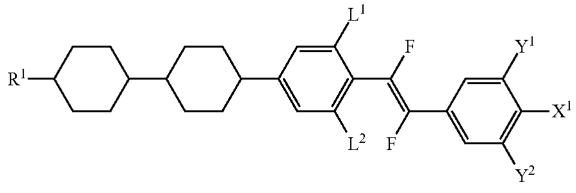

(1-37)

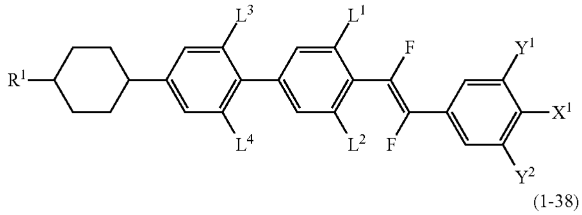

(1-38)

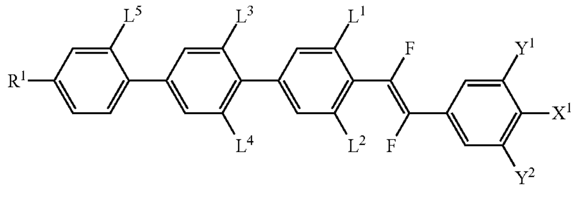

wherein, in the formulas, $R^1$ is alkyl having 1 to 12 carbons; $L^1$, $L^2$, $L^3$, $L^4$, $L^5$, $Y^1$ and $Y^2$ are independently hydrogen or fluorine; and $X^1$ is fluorine, $-CF_3$ or $-OCF_3$.

Item 8. A liquid crystal composition, containing at least one compound according to any one of items 1 to 7 as one component, and including two or more components.

Item 9. The liquid crystal composition according to item 8, containing at least one compound selected from the group of compounds represented by formulas (2), (3) and (4) as one component:

(2)

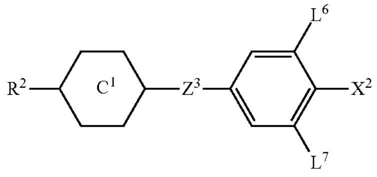

(3)

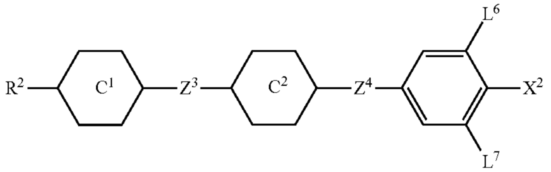

(4)

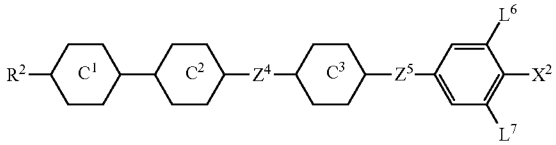

wherein, in the formulas, $R^2$ is alkyl having 1 to 10 carbons or alkenyl having 2 to 10 carbons, and in the alkyl and the alkenyl, arbitrary hydrogen may be replaced by fluorine, and in the groups, arbitrary $-CH_2-$ may be replaced by $-O-$; $X^2$ is fluorine, chlorine, $-OCF_3$, $-OCHF_2$, $-CF_3$, $-CHF_2$, $-CH_2F$, $-OCF_2CHF_2$ or $-OCF_2CHFCF_3$; ring $C^1$, ring $C^2$ and ring $C^3$ are independently 1,4-cyclohexylene, 1,3-dioxane-2,5-diyl, pyrimidine-2,5-diyl, tetrahydropyran-2,5-diyl, 1,4-phenylene, or 1,4-phenylene in which arbitrary hydrogen is replaced by fluorine; $Z^3$, $Z^4$ and $Z^5$ are independently $-(CH_2)_2-$, $-(CH_2)_4-$, $-COO-$, $-CF_2O-$, $-OCF_2-$, $-CH{=}CH-$, $-C{\equiv}C-$, $-CH_2O-$ or a single bond; and $L^6$ and $L^7$ are independently hydrogen or fluorine.

Item 10. The liquid crystal composition according to item 8, containing at least one compound selected from the group of compounds represented by formula (5) as one component:

(5)

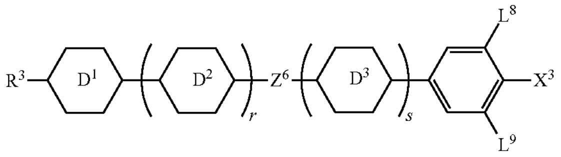

wherein, in formula (5), $R^3$ is alkyl having 1 to 10 carbons or alkenyl having 2 to 10 carbons, and in the alkyl and the alkenyl, arbitrary hydrogen may be replaced by fluorine, and in the groups, arbitrary $—CH_2—$ may be replaced by —O—; $X^3$ is —C≡N or —C≡C—C≡N; ring $D^1$, ring $D^2$ and ring $D^3$ are independently 1,4-cyclohexylene, 1,4-phenylene, 1,4-phenylene in which arbitrary hydrogen is replaced by fluorine, 1,3-dioxane-2,5-diyl, tetrahydropyran-2,5-diyl or pyrimidine-2,5-diyl; $Z^6$ is $—(CH_2)_2—$, —COO—, $—CF_2O—$, $—OCF_2—$, —C≡C—, $—CH_2O—$ or a single bond; $L^8$ and $L^9$ are independently hydrogen or fluorine; and r and s are independently 0 or 1.

Item 11. The liquid crystal composition according to item 8, containing at least one compound selected from the group of compounds represented by formulas (6), (7), (8), (9) and (10) as one component:

(11)

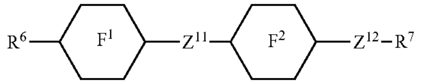

(12)

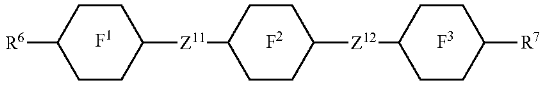

(13)

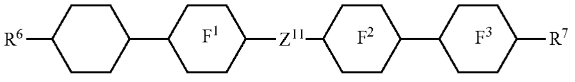

wherein, in the formulas, $R^6$ and $R^7$ are independently alkyl having 1 to 10 carbons or alkenyl having 2 to 10 carbons, and in the alkyl and the alkenyl, arbitrary hydrogen may be replaced by fluorine, and in the groups, arbitrary $—CH_2—$ may be replaced by —O—; ring $F^1$, ring $F^2$ and ring $F^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{11}$ and $Z^{12}$ are independently —C≡C—, —COO—, $—(CH_2)_2—$, —CH═CH— or a single bond.

(6)

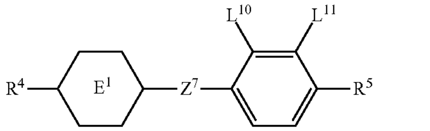

(7)

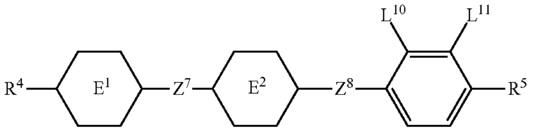

(8)

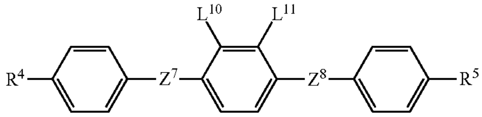

(9)

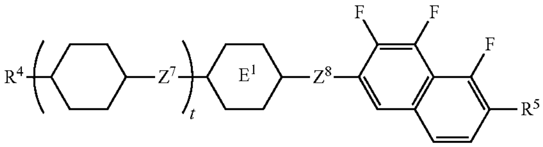

(10)

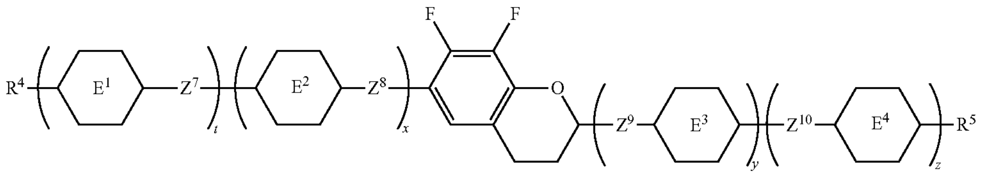

wherein, in the formulas, $R^4$ and $R^5$ are independently alkyl having 1 to 10 carbons or alkenyl having 2 to 10 carbons, and in the alkyl and the alkenyl, arbitrary hydrogen may be replaced by fluorine, and in the groups, arbitrary $—CH_2—$ may be replaced by —O—; ring $E^1$, ring $E^2$, ring $E^3$ and ring $E^4$ are independently 1,4-cyclohexylene, 1,4-cyclohexenylene, 1,4-phenylene, 1,4-phenylene in which arbitrary hydrogen is replaced by fluorine, tetrahydropyran-2,5-diyl or decahydronaphthalene-2,6-diyl; $Z^7$, $Z^8$, $Z^9$ and $Z^{10}$ are independently $—(CH_2)_2—$, —COO—, $—CH_2O—$, $—OCF_2—$, $—OCF_2—(CH_2)_2—$ or a single bond; $L^{10}$ and $L^{11}$ are independently fluorine or chlorine; and t, u, x, y and z are independently 0 or 1, and a sum of u, x, y and z is 1 or 2.

Item 12. The liquid crystal composition according to item 8, containing at least one compound selected from the group of compounds represented by formulas (11), (12) and (13) as one component:

Item 13. The liquid crystal composition according to item 9, further containing at least one compound selected from the group of compounds represented by formula (5) according to item 10.

Item 14. The liquid crystal composition according to item 9, further containing at least one compound selected from the group of compounds represented by formulas (11), (12) and (13) according to item 12.

Item 15. The liquid crystal composition according to item 10, further containing at least one compound selected from the group of compounds represented by formulas (11), (12) and (13) according to item 12.

Item 16. The liquid crystal composition according to item 11, further containing at least one compound selected from the group of compounds represented by formulas (11), (12) and (13) according to item 12.

Item 17. The liquid crystal composition according to any one of items 8 to 16, further containing at least one optically active compound.

Item 18. The liquid crystal composition according to any one of items 8 to 17, further containing at least one antioxidant and/or at least one ultraviolet light absorber.

Item 19. A liquid crystal display device containing the liquid crystal composition according to any one of items 8 to 18.

Usage of terms in the invention is as described below. The liquid crystal compound is a generic term for a compound having a liquid crystal phase such as a nematic phase or a smectic phase, and a compound having no liquid crystal phase but being useful as a component of the liquid crystal composition. "Liquid crystal compound," "liquid crystal composition" and "liquid crystal display device" may be abbreviated as "compound," "composition" and "device," respectively. The liquid crystal display device is a generic term for a liquid crystal display panel and a liquid crystal display module. A higher limit of a temperature range of the nematic phase is a phase transition temperature between the nematic phase and an isotropic phase, and may simply be abbreviated as "clearing point" or "maximum temperature." A lower limit of the temperature range of the nematic phase may simply be abbreviated as "minimum temperature." The compound represented by formula (1) may be abbreviated as "compound (1)." The abbreviation may also apply to the compound represented by formula (2) and so forth. In formula (1) to formula (13), symbols such as $A^1$, $B^1$ and $C^1$ surrounded by a hexagonal shape correspond to ring $A^1$, ring $B^1$ and ring $C^1$, respectively. A plurality of identical symbols such as ring $A^1$, $Y^1$ and B are described in identical or different formulas, and two of arbitrary symbols may be identical or different. An amount of the compound expressed in terms of "percentage" is expressed in terms of "weight percent (% by weight)" based on the total weight of the composition.

An expression "arbitrary A may be replaced by B, C or D" includes a case where arbitrary A is replaced by B, a case where arbitrary A is replaced by C, a case where arbitrary A is replaced by D, and also a case where at least two of A are replaced by at least two of B to D. For example, alkyl in which arbitrary $—CH_2—$ may be replaced by —O—, and arbitrary $—CH_2CH_2—$ may be replaced by —CH═CH— includes alkyl, alkenyl, alkoxy, alkoxyalkyl, alkoxyalkenyl and alkenyloxyalkyl. According to the invention, it is not preferred that two successive $—CH_2—$ are replaced by —O— to form —O—O— or the like. It is not preferred either that $—CH_2—$ of terminal $CH_3$ of alkyl or the like is replaced by —O— to form —O—H or the like. The invention will be further explained below.

Advantageous Effects of Invention

A liquid crystal compound of the invention has general physical properties necessary for the compound, namely, stability to heat, light and so forth, a wide temperature range of liquid crystal phases, a high clearing point, a good compatibility with other compounds, a large refractive index anisotropy, a large dielectric anisotropy and a small viscosity. A liquid crystal composition of the invention has a high maximum temperature of a nematic phase, a low minimum temperature of the nematic phase, a small viscosity, a refractive index anisotropy of a suitable magnitude and a low threshold voltage. A liquid crystal display device of the invention contains the composition and has a wide temperature range in which the device can be used, a short response time, a small electric power consumption, a large contrast ratio and a low driving voltage.

DESCRIPTION OF EMBODIMENTS

1-1. Compound of the Invention

A first embodiment of the invention concerns a compound represented by formula (1):

(1)

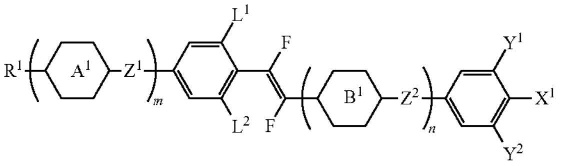

wherein, in formula (1), $R^1$ is alkyl having 1 to 20 carbons, and in the alkyl, arbitrary $—CH_2—$ may be replaced by —O— or —S—, and in the groups, arbitrary $—CH_2CH_2—$ may be replaced by —CH═CH—. For example, in $CH_3—(CH_2)_3—$, a group in which arbitrary $—CH_2—$ is replaced by —O— or —S—, and arbitrary $—CH_2CH_2—$ is replaced by —CH═CH— includes $CH_3—(CH_2)_2—O—$, $CH_3O—(CH_2)_2—$, $CH_3OCH_2O—$, $CH_3—(CH_2)_2—S—$, $CH_3S—(CH_2)_2—$, $CH_3SCH_2S—$, $CH_2═CH—(CH_2)_2—$, $CH_3CH═CHCH_2—$ and $CH_2═CHCH_2O—$.

Such $R^1$ includes alkyl, alkoxy, alkoxyalkyl, alkoxyalkoxy, thioalkyl, thioalkylalkoxy, alkenyl, alkenyloxy, alkenyloxyalkyl and alkoxyalkenyl. In the groups, $R^1$ may have a straight chain or a branched chain, and the straight chain is preferred to the branched chain. Even if $R^1$ is a branched-chain group, $R^1$ when the group is optically active is preferred. A preferred configuration of —CH═CH— in alkenyl depends on a position of a double bond. A trans configuration is preferred in alkenyl having the double bond in an odd-numbered position, such as $—CH═CHCH_3$, $—CH═CHC_2H_5$, $—CH═CHC_3H_7$, $—CH═CHC_4H_9$, $—C_2H_4CH═CHCH_3$ and $—C_2H_4CH═CHC_2H_5$. A cis configuration is preferred in alkenyl having the double bond in an even-numbered position, such as $—CH_2CH═CHCH_3$, $—CH_2CH═CHC_2H_5$ and $—CH_2CH═CHC_3H_7$. An alkenyl compound having a preferred configuration has a high maximum temperature or a wide temperature range of a liquid crystal phase. A detailed description is found in Mol. Cryst. Liq. Cryst., 1985, 131, 109 and Mol. Cryst. Liq. Cryst., 1985, 131, 327.

The alkyl includes $—CH_3$, $—C_2H_5$, $—C_3H_7$, $—C_4H_9$, $—C_5H_{11}$, $—C_6H_{13}$, $—C_7H_{15}$, $—C_8H_{17}$, $—C_9H_{19}$, $—C_{10}H_{21}$, $—C_{11}H_{23}$, $—C_{12}H_{25}$, $—C_{13}H_{27}$, $—C_{14}H_{29}$ and $—C_{15}H_{31}$.

The alkoxy includes $—OCH_3$, $—OC_2H_5$, $—OC_3H_7$, $—OC_4H_9$, $—OC_5H_{11}$, $—OC_6H_{13}$, $—OC_7H_{15}$, $—OC_8H_{17}$, $—OC_9H_{19}$, $—OC_{10}H_{21}$, $—OC_{11}H_{23}$, $—OC_{12}H_{25}$, $—OC_{13}H_{27}$ and $—OC_{14}H_{29}$.

The alkoxyalkyl includes $—CH_2OCH_3$, $—CH_2OC_2H_5$, $—CH_2OC_3H_7$, $—(CH_2)_2—OCH_3$, $—(CH_2)_2—OC_2H_5$, $—(CH_2)_2—OC_3H_7$, $—(CH_2)_3—OCH_3$, $—(CH_2)_4—OCH_3$ and $—(CH_2)_5—OCH_3$.

The alkenyl includes $—CH═CH_2$, $—CH═CHCH_3$, $—CH_2CH═CH_2$, $—CH═CHC_2H_5$, $—CH_2CH═CHCH_3$, $—(CH_2)_2—CH═CH_2$, $—CH═CHC_3H_7$, $—CH_2CH═CHC_2H_5$, $—(CH_2)_2—CH═CHCH_3$ and $—(CH_2)_3—CH═CH_2$.

The alkenyloxy includes $—OCH_2CH═CH_2$, $—OCH_2—CH═CHCH_3$ and $—OCH_2CH═CHC_2H_5$.

Preferred $R^1$ includes alkyl having 1 to 15 carbons or alkenyl having 2 to 15 carbons.

Further preferred $R^1$ is $—CH_3$, $—C_2H_5$, $—C_3H_7$, $—C_4H_9$, $—C_5H_{11}$, $—C_6H_{13}$, $—C_7H_{15}$, $—C_8H_{17}$, $—C_9H_{19}$, $—C_{10}H_{21}$, $—C_{11}H_{23}$, $—C_{12}H_{25}$, $—C_{13}H_{27}$, $—C_{14}H_{29}$, $—C_{15}H_{31}$, $—CH═CH_2$, $—CH═CHCH_3$, $—CH_2CH═CH_2$, $—CH═CHC_2H_5$, $—CH_2CH═CHCH_3$, $—(CH_2)_2—CH═CH_2$, $—CH═CHC_3H_7$, $—CH_2CH═CHC_2H_5$, $—(CH_2)_2—CH═CHCH_3$ and $—(CH_2)_3—CH═CH_2$.

In formula (1), ring $A^1$ is 1,4-cyclohexylene (14-1), 1,3-dioxane-2,5-diyl (14-2), tetrahydropyran-2,5-diyl (14-3), pyrimidine-2,5-diyl (14-4), pyridine-2,5-diyl (14-5), 1,4-phenylene (14-6), or 1,4-phenylene in which arbitrary hydrogen is replaced by halogen. Herein, 1,4-phenylene in which arbitrary hydrogen is replaced by halogen includes 1,4-phenylene derivatives represented by formula (14-7) to formula (14-24). Preferred examples include 1,4-phenylene derivatives represented by formula (14-7) to formula (14-18).

(14-1)

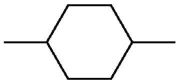

(14-2)

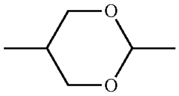

(14-3)

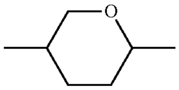

(14-4)

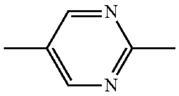

(14-5)

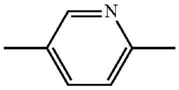

(14-6)

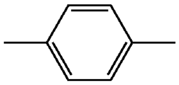

(14-7)

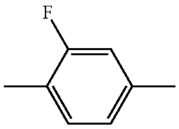

(14-8)

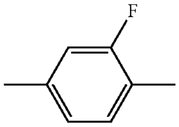

(14-9)

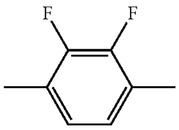

-continued (14-10)

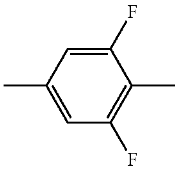

(14-11)

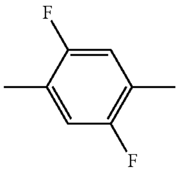

(14-12)

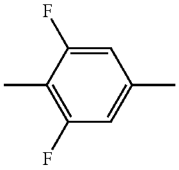

(14-13)

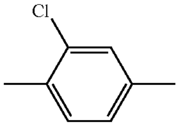

(14-14)

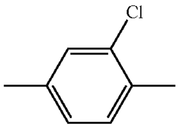

(14-15)

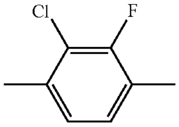

(14-16)

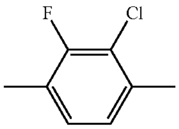

(14-17)

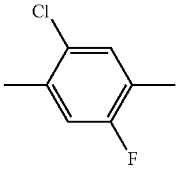

(14-18)

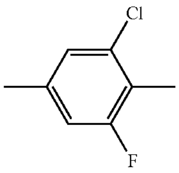

-continued (14-19)

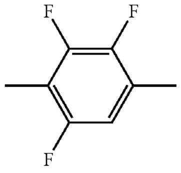

(14-20)

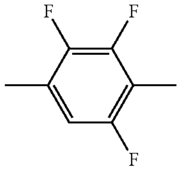

(14-21)

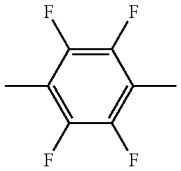

(14-22)

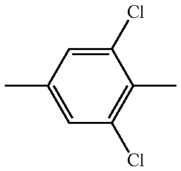

(14-23)

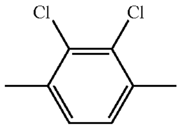

(14-24)

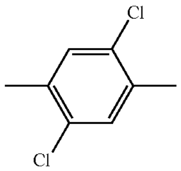

Preferred ring $A^1$ is 1,4-cyclohexylene (14-1), 1,3-dioxane-2,5-diyl (14-2), tetrahydropyran-2,5-diyl (14-3), pyrimidine-2,5-diyl (14-4), pyridine-2,5-diyl (14-5), 1,4-phenylene (14-6), 3-fluoro-1,4-phenylene (14-7) (14-8), 2,3-difluoro-1,4-phenylene (14-9), 2,5-difluoro-1,4-phenylene (14-11), 3,5-difluoro-1,4-phenylene (14-10), 2,6-difluoro-1,4-phenylene (14-12), 2-chloro-1,4-phenylene (14-13), 2-chloro-1,4-phenylene (14-14) and 3-chloro-5-fluoro-1,4-phenylene (14-18).

Further preferred ring $A^1$ is 1,4-cyclohexylene, 1,4-phenylene, 3-fluoro-1,4-phenylene and 3,5-difluoro-1,4-phenylene.

In formula (1), ring $B^1$ is 1,4-phenylene (14-6), 3-fluoro-1,4-phenylene (14-7), 3,5-difluoro-1,4-phenylene (14-10), 3-chloro-1,4-phenylene (14-14) or 3-chloro-5-fluoro-1,4-phenylene (14-18).

Preferred ring $B^1$ is 1,4-phenylene, 3-fluoro-1,4-phenylene and 3,5-difluoro-1,4-phenylene. Further preferred ring $B^1$ is 1,4-phenylene and 3-fluoro-1,4-phenylene.

In formula (1), $Z^1$ and $Z^2$ are independently a single bond, —$CH_2CH_2$—, —CH═CH— or With regard to the configuration of the double bond of —CH═CH—, trans is preferred to cis. Preferred $Z^1$ or $Z^2$ is a single bond, —$CH_2CH_2$— and —CH═CH—. Further preferred $Z^1$ or $Z^2$ is a single bond.

In formula (1), $L^1$, $L^2$, $Y^1$ and $Y^2$ are independently hydrogen, fluorine or chlorine. Then, when m is 1 and n is 0, at least one of $L^1$ and $L^2$ is fluorine. Preferred $L^1$, $L^2$, $Y^1$ or $Y^2$ is hydrogen or fluorine.

In formula (1), $X^1$ is hydrogen, halogen, —N═C═S, —$SF_5$ or alkyl having 1 to 10 carbons, and in the alkyl, arbitrary —$CH_2$— may be replaced by —O— or —S—, and arbitrary —$CH_2CH_2$— may be replaced by —CH═CH—. In alkyl having 1 to 10 carbons, a group in which arbitrary —$CH_2$— is replaced by —O— or —S—, and a group in which arbitrary —$CH_2CH_2$— is replaced by —CH═CH—, arbitrary hydrogen may be replaced by halogen.

Such $X^1$ includes alkyl, alkoxy, alkoxyalkyl, alkoxyalkoxy, thioalkyl, thioalkylalkoxy, alkenyl, alkenyloxy, alkenyloxyalkyl, alkoxyalkenyl, and halogenated groups thereof. In the groups, $X^1$ may have a straight chain or a branched chain, and the straight chain is preferred to the branched chain.

The alkyl in which arbitrary hydrogen is replaced by halogen includes —$CH_2F$, —$CHF_2$, —$CF_3$, —$(CH_2)_2$—F, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F and —$(CF_2)_5$—F.

The alkoxy in which arbitrary hydrogen is replaced by halogen includes —$OCH_2F$, —$OCHF_2$, —$OCF_3$, —O—$(CH_2)_2$—F, —$OCF_2CH_2F$, —$OCF_2CHF_2$, —$OCH_2CF_3$, —O—$(CH_2)_3$—F, —O—$(CF_2)_3$—F, —$OCF_2CHFCF_3$, —$OCHFCF_2CF_3$, —O—$(CH_2)_4$—F, —O—$(CF_2)_4$—F, —O—$(CH_2)_5$—F and —O—$(CF_2)_5$—F.

The alkenyl in which arbitrary hydrogen is replaced by halogen includes —CH═CHF, —CH═$CF_2$, —CF═CHF, —CH═$CHCH_2F$, —CH═$CHCF_3$, —$(CH_2)_2$—CH═$CF_2$, —$CH_2CH$═$CHCF_3$ and —CH═$CHCF_2CF_3$.

$X^1$ includes hydrogen, fluorine, chlorine, —C≡N, —$SF_5$, —$CH_3$, —$C_2H_5$, —$C_3H_7$—$C_4H_9$, —$C_5H_{11}$, —$C_6H_{13}$, —$C_7H_{ts}$, —$C_8H_{17}$, —$C_9H_{19}$, —$C_{10}H_{21}$, —$CH_2F$, —$CHF_2$, —$CF_3$—$(CH_2)_2$—F, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F, —$(CF_2$—F, —$OCH_3$, —$OC_2H_5$, —$OC_3H_7$, —$OC_4H_9$, —$OC_5H_{11}$, —$OCH_2F$, —$OCHF_2$, —$OCF_3$, —O—$(CH_2$—F, —$OCF_2CH_2F$, —$OCF_2CHF_2$, —$OCH_2CF_3$, —O—$(CH_2)_3$—F, —O—$(CF_2)_3$—F, —$OCF_2CHFCF_3$, —$OCHFCF_2CF_3$, —O$(CH_2)_4$—F, —O—$(CF_2)_4$—F, —O—$(CH_2)_5$—F, —O—$(CF_2)_5$—F, —CH═$CH_2$—CH═$CHCH_3$, —$CH_2CH$═$CH_2$, —CH═$CHC_2H_5$, —$CH_2CH$═$CHCH_3$, —$(CH_2)_2$—CH═$CH_2$, —CH═$CHC_3H_7$, —$CH_2CH$═$CHC_2H_5$—$(CH_2)_2$—CH═$CHCH_3$, —$(CH_2)_3$—CH═$CH_2$, —CH═CHF, —CH═$CF_2$, —CF═CHF, —CH═$CHCH_2F$, —CH═$CHCF_3$, —$(CH_2)_2$—CH═$CF_2$, —$CH_2CH$═$CHCF_3$ and —CH═$CHCF_2CF_3$.

Preferred $X^1$ is fluorine, chlorine, —CN, —$CF_3$, —$CHF_2$, —$CH_2F$, —$OCF_3$, —$OCHF_2$ or —$OCH_2F$. Further preferred $X^1$ is fluorine, —$CF_3$ or —$OCF_3$.

In formula (1), m is 1 or 2 and n is 0 or 1. More specifically, a combination of m and n includes (m=1 and n=0) as in formula (1-1), (m=2 and n=0) as in formula (1-2), (m=1 and n=1) as in formula (1-3) and (m=2 and n=1) as in formula (1-4). A preferred combination of m and n is (m=1 and n=0) as in formula (1-1) and (m=2 and n=0) as in formula (1-2).

(1-1)

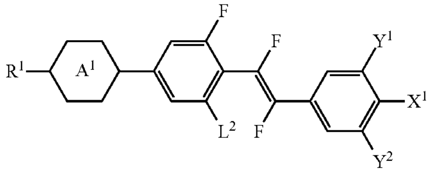

(1-2)

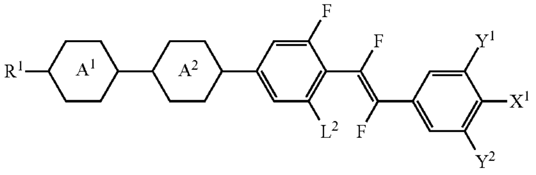

(1-3)

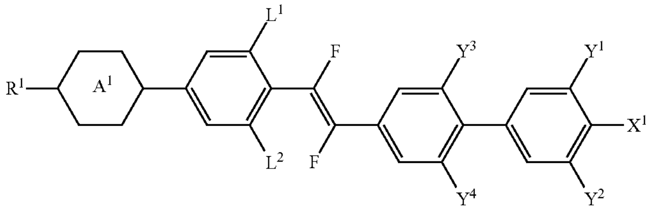

(1-4)

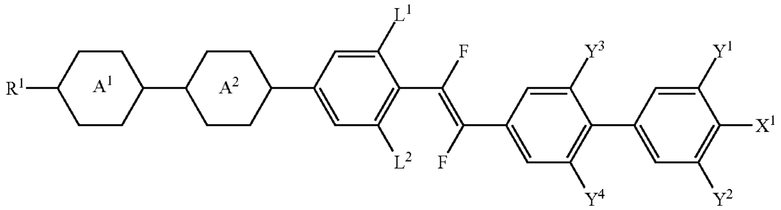

1-2. Properties of the Compound of the Invention, and a Preparation Method Therefor Compound (1) will be explained in more detail. Compound (1) is a three-ring, four-ring or five-ring compound having a difluoroethylene bonding group. The compound is physically and chemically stable under conditions in which a device is ordinarily used, and has a good compatibility with other compounds. A composition containing the compound is stable under conditions in which the device is ordinarily used. Even if the composition is stored at a low temperature, the compound does not precipitate in the form of crystals (or a smectic phase). In particular, the four-ring compound and the five-ring compound have a wide temperature range of the liquid crystal phase and a high clearing point. Accordingly, a temperature range of a nematic phase can be extended in the composition, and the compound can be used in the form of the device in the wide temperature range. The compound has a large refractive index anisotropy. Thus, a composition having a large refractive index anisotropy can be provided using the compound, and therefore the compound is suitable for preparing a device exhibiting a high display performance. Moreover, the compound has a large dielectric anisotropy, and therefore is useful as a component for decreasing a threshold voltage of the composition. Furthermore, the compound has a small viscosity, and a composition having a small viscosity can be provided using the compound. Therefore, the compound is suitable for manufacturing a device that can respond at a high speed.

Physical properties such as a clearing point, a refractive index anisotropy and a dielectric anisotropy can be arbitrarily adjusted by suitably selecting the combination of m and n, and types of ring $A^1$, ring $B^1$, left-terminal group $R^1$, right-terminal group $X^1$, lateral groups $L^1$, $L^2$, $Y^1$ and $Y^2$, and bonding groups $Z^1$ and $Z^2$ in compound (1). An effect of the combination and the types on the physical properties of compound (1) will be explained below.

When the combination of m and n is (m=1 and n=0) as in formula (1-1), compound (1) has a good compatibility with other compounds, a large dielectric anisotropy and a small viscosity. When the combination is (m=2 and n=0) as in formula (1-2), compound (1) has a wide temperature range of the liquid crystal phase, a high clearing point, a large refractive index anisotropy, a large dielectric anisotropy and a small viscosity. When the combination is (m=1 and n=1) as in formula (1-3), compound (1) has a good compatibility with other compounds and a large dielectric anisotropy. When the combination is (m=2 and n=1) as in formula (1-4), compound (1) has a high clearing point, a very large dielectric anisotropy and a very large refractive index anisotropy.

When ring $A^1$ is 1,4-cyclohexylene, compound (1) has a good compatibility with other compounds and a small viscosity. When ring $A^1$ is 1,3-dioxane-2,5-diyl, compound (1) has a large dielectric anisotropy. When ring $A^1$ is tetrahydropyran-2,5-diyl, compound (1) has a good compatibility with other compounds. When ring $A^1$ is pyrimidine-2,5-diyl or pyridine-2,5-diyl, compound (1) has a high clearing point, a large refractive index anisotropy and a large dielectric anisotropy. When ring $A^1$ is 1,4-phenylene, or 1,4-phenylene in which arbitrary hydrogen is replaced by halogen, compound (1) has a good compatibility with other compounds, a large refractive index anisotropy and a small viscosity.

When ring $B^1$ is 1,4-phenylene, compound (1) has a high clearing point and a large refractive index anisotropy. When ring $B^1$ is 3-fluoro-1,4-phenylene, compound (1) has a good compatibility with other compounds and a large dielectric anisotropy. When ring $B^1$ is 3,5-difluoro-1,4-phenylene, compound (1) has a large dielectric anisotropy. When ring $B^1$ is 3-chloro-1,4-phenylene or 3-chloro-5-fluoro-1,4-phenylene, compound (1) has a good compatibility with other compounds and a large dielectric anisotropy.

When left-terminal group $R^1$ has a straight chain, compound (1) has a wide temperature range of the liquid crystal phase and a small viscosity. When $R^1$ has a branched chain, compound (1) has a good compatibility with other compounds. A compound in which $R^1$ is an optically active group is useful as a chiral dopant. A reverse twisted domain that is generated in the device can be prevented by adding the compound to the composition. A compound in which $R^1$ is not the optically active group is useful as a component of the composition. When $R^1$ is alkenyl, a preferred configuration depends on the position of the double bond. An alkenyl compound having the preferred configuration has a high maximum temperature or a wide temperature range of the liquid crystal phase.

When right-terminal group $X^1$ is fluorine, chlorine, —C≡N, —N=C=S, $—SF_5$, $—CF_3$, $—CHF_2$, $—CH_2F$, $—OCF_3$, $—OCHF_2$ or $—OCH_2F$, compound (1) has a large dielectric anisotropy. When $X^1$ is —C≡N, —N=C=S or alkenyl, compound (1) has a large refractive index anisotropy. When $X^1$ is fluorine, $—CF_3$, $—OCF_3$ or alkyl, compound (1) has a chemical stability.

When lateral group $L^1$ is fluorine and $L^2$ is hydrogen, compound (1) has a good compatibility with other compounds. When both $L^1$ and $L^2$ are fluorine, compound (1) has a large dielectric anisotropy. When $L^1$ is fluorine and $L^2$ is chlorine, When bonding groups $Z^1$ and $Z^2$ are a single bond or $—CH_2CH_2—$, compound (1) has a small viscosity and a chemical stability. When $Z^1$ and $Z^2$ are —CH=CH—, compound (1) has a wide temperature range of the liquid crystal phase and a large elastic constant ratio $K_{33}/K_1$ ($K_{33}$: bend elastic constant, $K_{11}$: spray elastic constant). When the bonding groups are —C≡C—, compound (1) has a high clearing point and a large refractive index anisotropy.

As described above, a compound having targeted physical properties can be obtained by suitably selecting the types of rings, terminal groups, bonding groups and so forth. Accordingly, compound (1) is useful as a component of the composition to be used for a device having a mode such as PC, TN, STN, ECB, OCB, IPS or VA.

1-3. Preferred Examples of Compound (1)

Preferred compound (1) includes compound (1-1) to compound (1-4). Further preferred compound (1) includes compound (1-5) to compound (1-33). Still further preferred compound (1) includes compound (1-34) to compound (1-38).

(1-1)

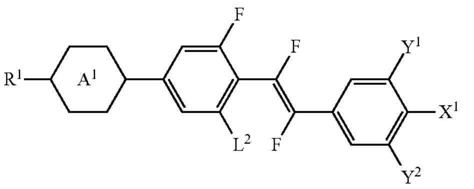

(1-2)

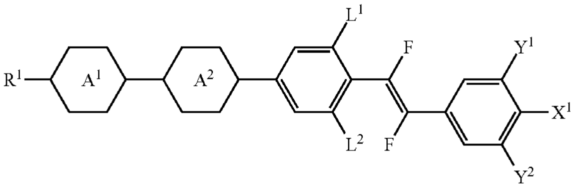

(1-3)

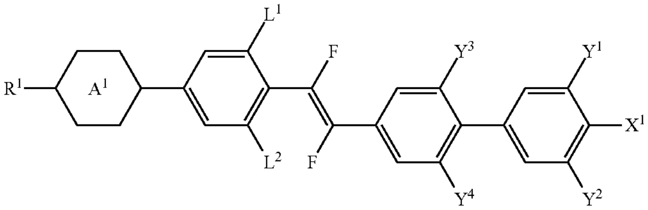

(1-4)

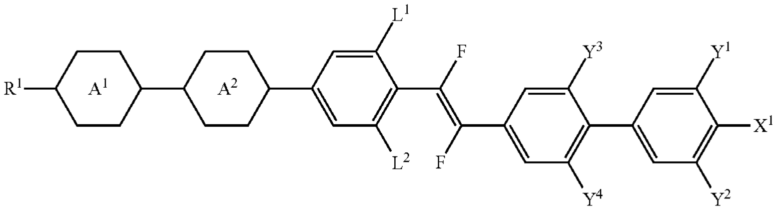

compound (1) has a good compatibility with other compounds and a large dielectric anisotropy. When lateral group $Y^1$ is fluorine and $Y^2$ is hydrogen, compound (1) has a good compatibility with other compounds. When both $Y^1$ and $Y^2$ are fluorine, compound (1) has a large dielectric anisotropy. When both $Y^1$ and $Y^2$ are hydrogen, compound (1) has a high clearing point, a large refractive index anisotropy and a small viscosity.

wherein, in the formulas, $R^1$ is alkyl having 1 to 12 carbons or alkenyl having 2 to 12 carbons; ring $A^1$ and ring $A^2$ are independently 1,4-cyclohexylene, 1,3-dioxane-2,5-diyl, tetrahydropyran-2,5-diyl, pyrimidine-2,5-diyl, pyridine-2,5-diyl, 1,4-phenylene, or 1,4-phenylene in which arbitrary hydrogen is replaced by halogen; $L^1$, $L^2$, $Y^1$, $Y^2$, $Y^3$ and $Y^4$ are independently hydrogen, fluorine or chlorine; and $X^1$ is fluorine, chlorine, $—CF_3$ or $—OCF_3$.

(1-5)
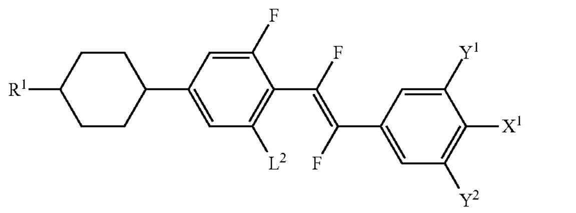
(1-6)
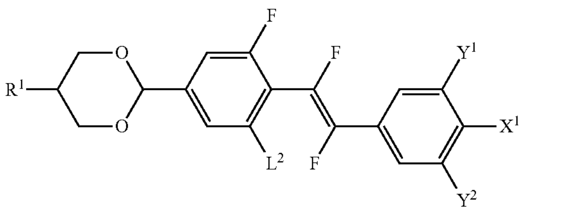
(1-7)
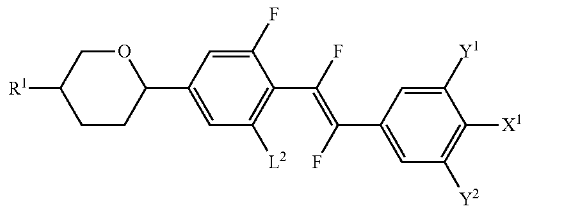
(1-8)
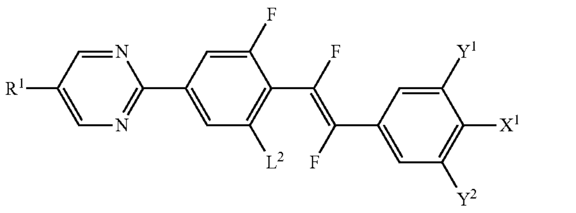
(1-9)
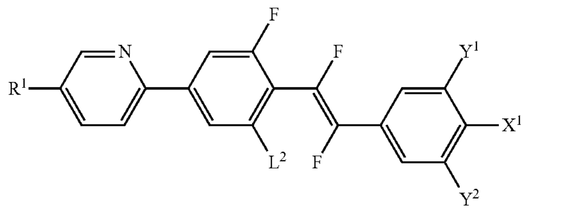
(1-10)
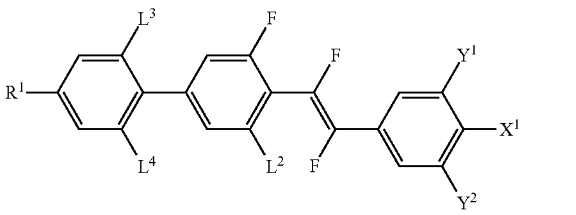
(1-11)
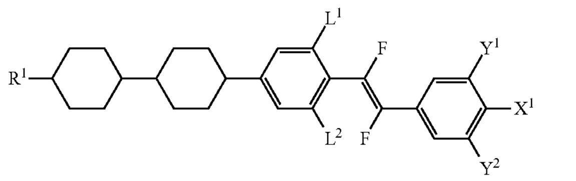
(1-12)
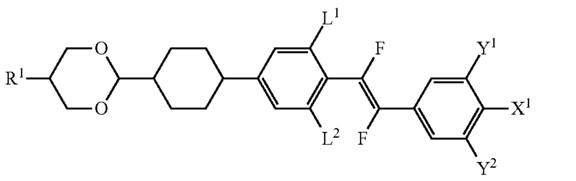
(1-13)
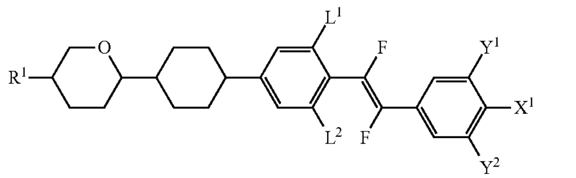
(1-14)
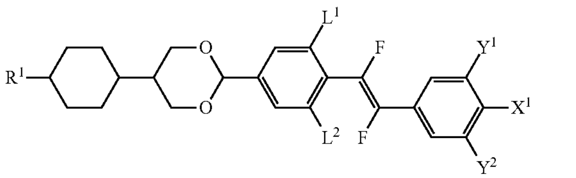
(1-15)
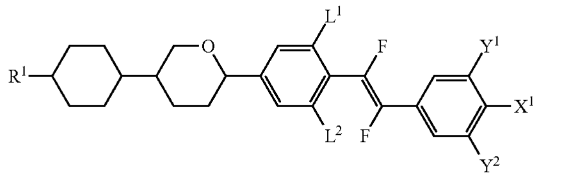
(1-16)
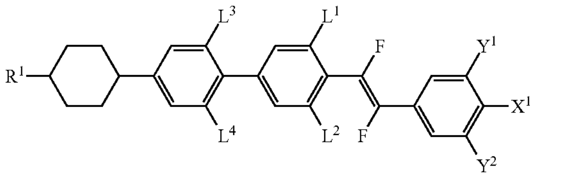
(1-17)
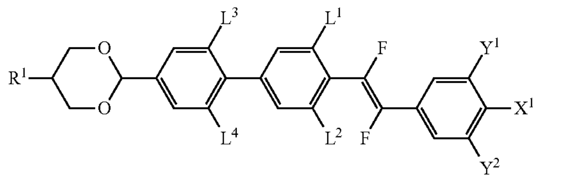
(1-18)
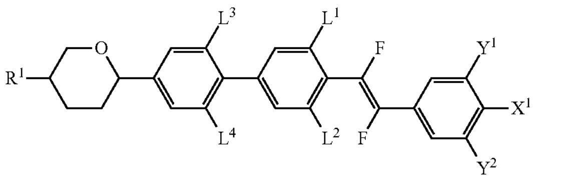

-continued
(1-19)
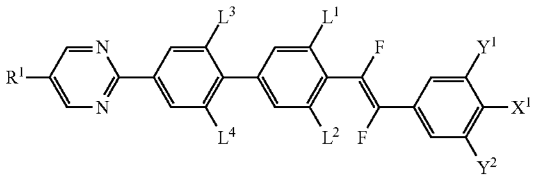
(1-20)
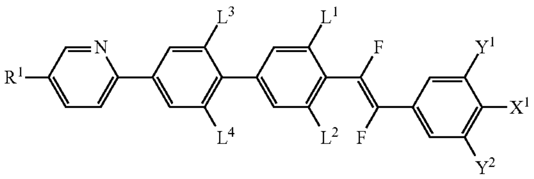
(1-21)
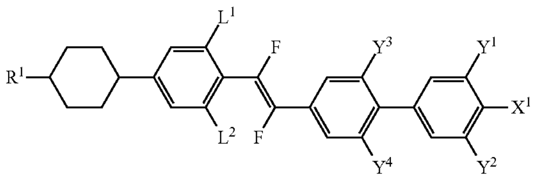
(1-22)
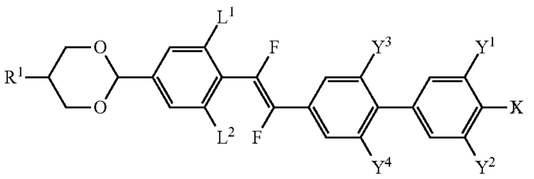
(1-23)
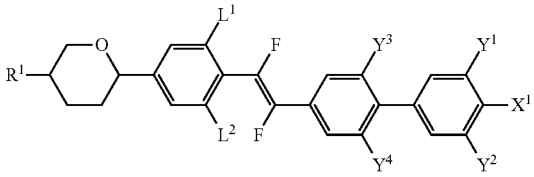
(1-24)
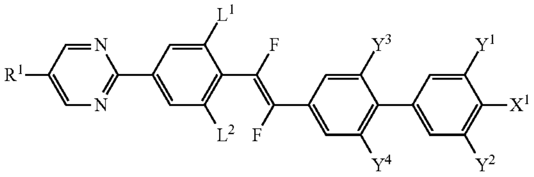
(1-25)
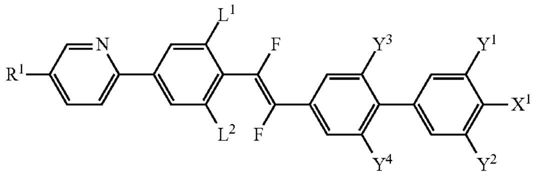
(1-26)
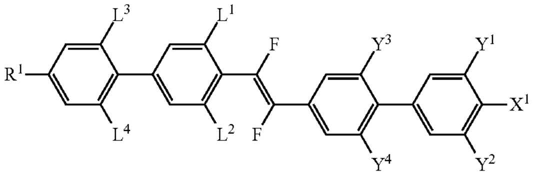
(1-27)
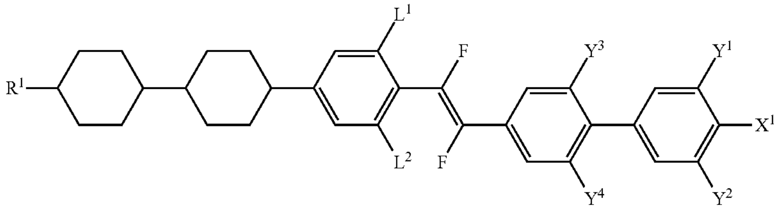
(1-28)
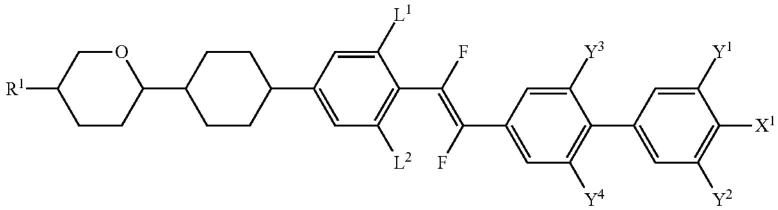
(1-29)
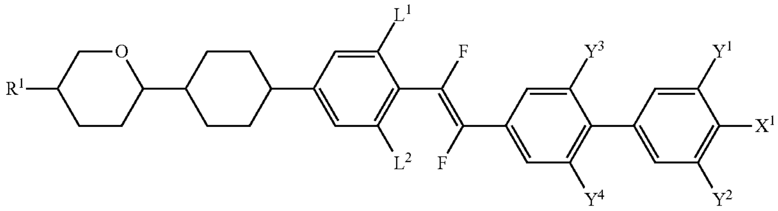

-continued
(1-30)
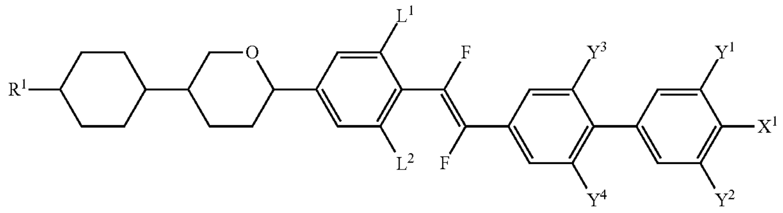
(1-31)
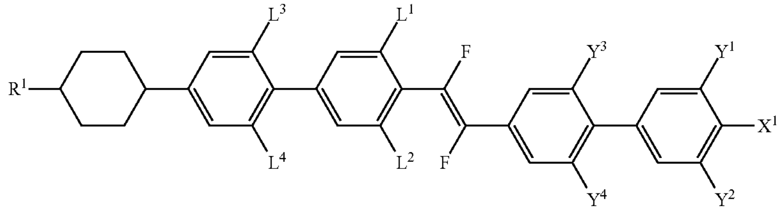
(1-32)
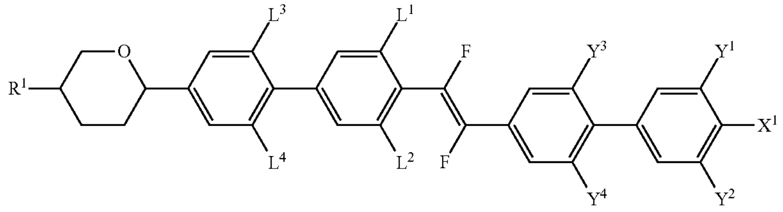
(1-33)
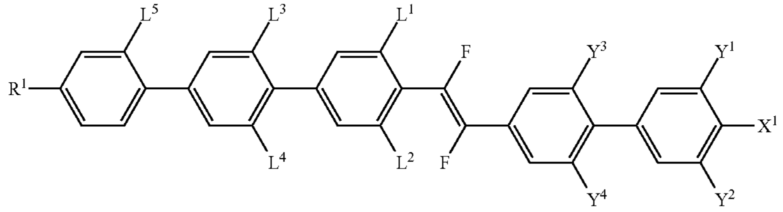
wherein, in the formulas, $R^1$ is alkyl having 1 to 12 carbons; $L^1$, $L^2$, $L^3$, $L^4$, $L^5$, $Y^1$, $Y^2$, $Y^3$ and $Y^4$ are independently hydrogen, chlorine or fluorine; and $X^1$ is fluorine, chlorine, —$CF_3$ or —$OCF_3$.
(1-34)
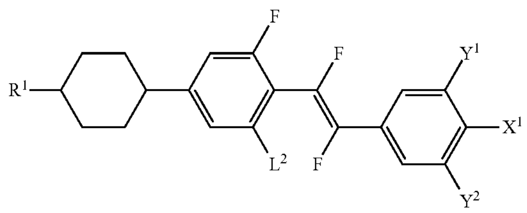
(1-35)
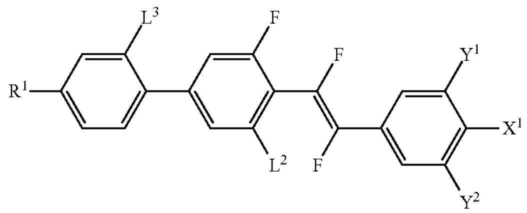
-continued
(1-36)
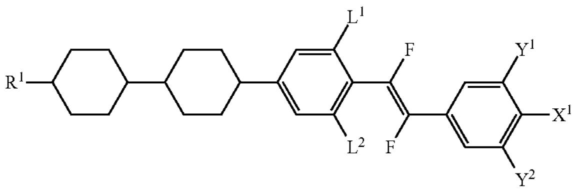
(1-37)
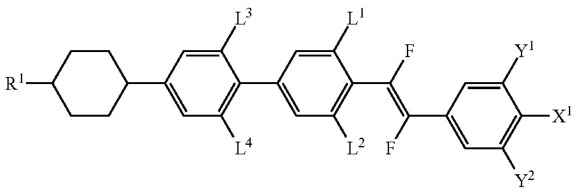
(1-38)
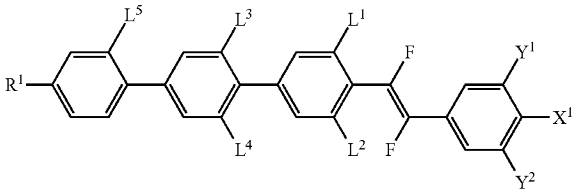

wherein, in the formulas, $R^1$ is alkyl having 1 to 12 carbons; $L^1$, $L^2$, $L^3$, $L^4$, $L^5$, $Y^1$ and $Y^2$ are independently hydrogen or fluorine; $X^1$ is fluorine, $—CF_3$ or $—OCF_3$.

1-4. Synthesis of Compound (1)

Next, synthesis of compound (1) will be explained. Compound (1) can be prepared by suitably combining techniques in synthetic organic chemistry. Methods for introducing a targeted terminal group, ring and bonding group into a starting material are described in Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.) or the like.

1-4-1. Method for Forming Bonding Groups $Z^1$ and $Z^2$

One example of methods for forming bonding groups $Z^1$ and $Z^2$ in compound (1) is as described in the scheme below. In the scheme, $MSG^1$ or $MSG^2$ is a monovalent organic group having at least one ring. A plurality of $MSG^1$ (or $MSG^2$) used in the scheme may be identical or different. Compound (1A) to compound (1D) correspond to compound (1).

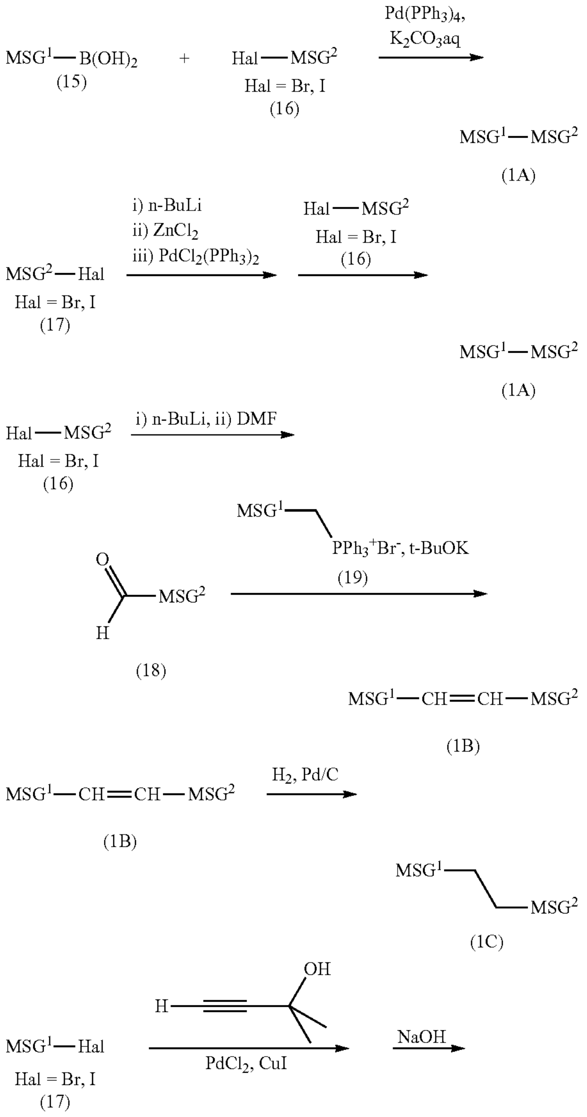

-continued

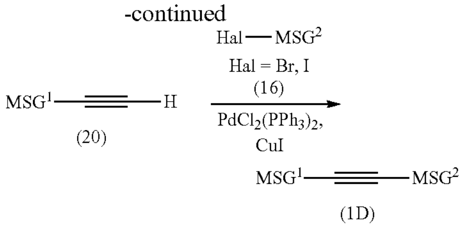

Next, methods for forming various types of bonds of bonding groups $Z^1$ and $Z^2$ in compound (1) will be explained in section (I) to section (IV) as described below.

(I) Formation of a Single Bond

Compound (1A) is prepared by allowing aryl boronic acid (15) to react, in the presence of an aqueous solution of carbonate and a catalyst such as tetrakis(triphenylphosphine) palladium, with compound (16) prepared according to a known method. Compound (1A) is also prepared by allowing compound (17) prepared according to a known method to react with n-butyllithium and subsequently with zinc chloride, and further with compound (16) in the presence of a catalyst such as dichlorobis(triphenylphosphine)palladium.

(II) Formation of $—CH{=}CH—$

Aldehyde (18) is obtained by treating compound (16) with n-butyllithium and then allowing the treated compound (16) to react with formamide such as N,N-dimethylformamide (DMF). Compound (1B) is prepared by allowing aldehyde (18) to react with phosphorus ylide generated by treating phosphonium salt (19) prepared according to a known method with a base such as potassium tert-butoxide. Because a cis isomer is formed depending on reaction conditions, the cis isomer is isomerized to a trans isomer according to a known method, when necessary.

(III) Formation of $—(CH_2)_2—$

Compound (1C) is prepared by hydrogenating compound (1B) in the presence of a catalyst such as palladium on carbon.

(IV) Formation of $—C{\equiv}C—$

Compound (20) is obtained by allowing compound (17) to react with 2-methyl-3-butyn-2-ol in the presence of a catalyst including dichloropalladium and copper halide, and then performing deprotection under basic conditions. Compound (1D) is prepared by allowing compound (20) to react with compound (16) in the presence of a catalyst including dichlorobistriphenylphosphine palladium and copper halide.

1-4-2. Method for Preparing Ring $A^1$ and Ring $B^1$

Starting materials are commercially available or synthetic processes are well known for rings such as 1,4-cyclohexylene, 1,3-dioxane-2,5-diyl, tetrahydropyran-2,5-diyl, pyrimidine-2,5-diyl, pyridine-2,5-diyl, 1,4-phenylene, 3-fluoro-1,4-phenylene, 3,5-difluoro-1,4-phenylene, 3-chloro-1,4-phenylene and 3-chloro-5-fluoro-1,4-phenylene.

1-4-3. Method for Preparing Compound (1)

A plurality of methods for preparing the compound represented by formula (1) are known. An example thereof is described herein. When $L^1$ is fluorine in formula (1), synthesis can be made according to the method described below. Fluoroiodobenzene derivative (22) is obtained by allowing n-BuLi or sec-BuLi to act on fluorobenzene derivative (21), and then allowing the resultant product to react with iodine. Derivative (22) is converted into trifluoroethylene derivative (23) by allowing derivative (22) to react, in the presence of a catalyst such as tetrakistriphenylphosphine palladium, with an organozinc reagent prepared from iodotrifluoroethylene and zinc powder. Compound (1-39) can be prepared by allowing n-BuLi to act on brominated product (24) prepared by a publicly known method and then allowing the resultant product to react with trifluoroethylene derivative (23).

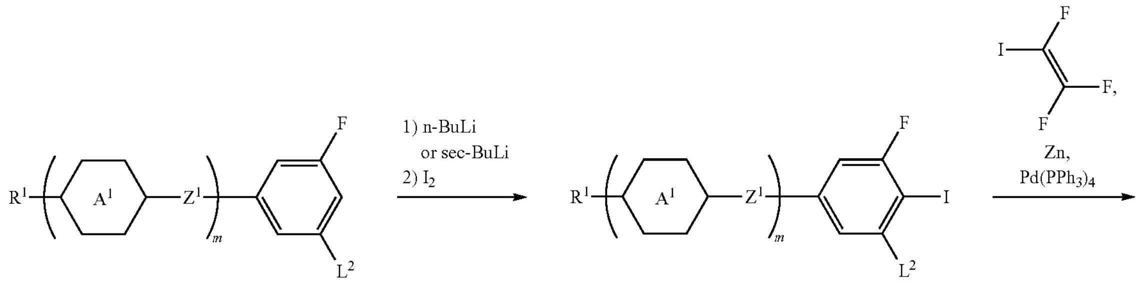

(21) (22)

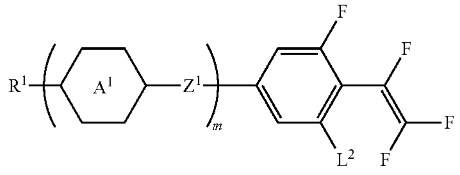

(23)

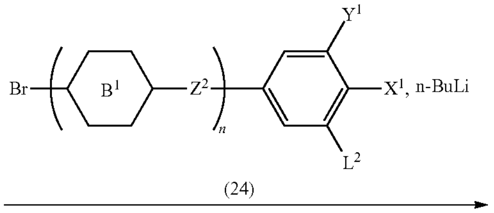

(24)

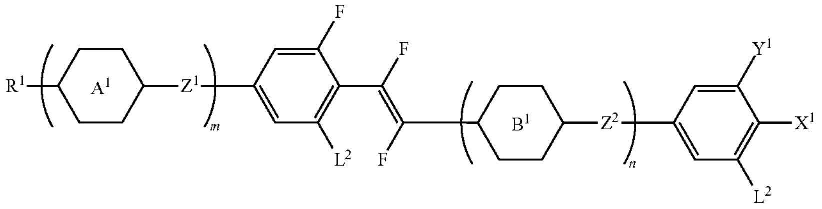

(1-39)

In the formulas, ring $A^1$, ring $B^1$, $Z^1$, $Z^2$, $L^2$, $Y^1$, $Y^2$, $R^1$, $X^1$, m and n are defined in the same way as described in item 1.

Compound (1) in which both $L^1$ and $L^2$ are hydrogen can be prepared by the method described below. Iodinated product (25) prepared by a publicly known method is converted into trifluoroethylene derivative (26) by allowing iodinated product (25) to react, in the presence of a catalyst such as tetrakistriphenylphosphine palladium, with an organozinc reagent prepared from iodotrifluoroethylene and zinc powder. Compound (1-40) can be prepared by allowing n-BuLi to act on brominated product (24) and then allowing the resultant product to react with trifluoroethylene derivative (26).

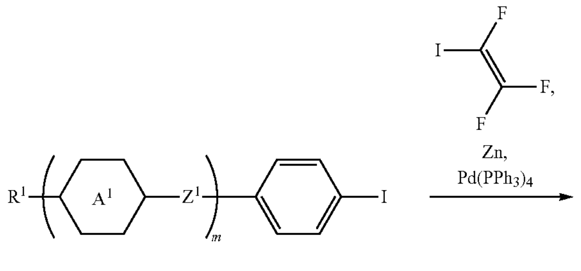

(25)

-continued

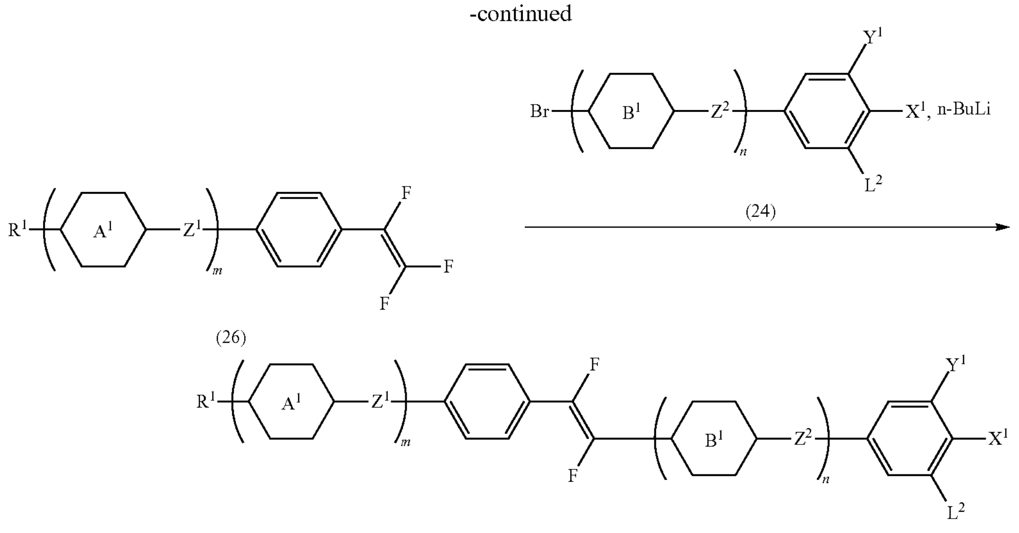

(1-40)

In the formulas, ring $A^1$, ring $B^1$, $Z^1$, $Z^2$, $Y^1$, $Y^2$, $R^1$, $X^1$, m and n are defined in the same way as described in item 1.

Compound (1) in which both $L^1$ and $L^2$ are hydrogen can also be prepared by the method described below. Brominated product (27) prepared by a publicly known method is converted into trifluoroethylene derivative (26) by allowing n-BuLi to act on brominated product (27) and then allowing the resultant product to react with tetrafluoroethylene. Compound (1-40) can be prepared in a similar manner as described above.

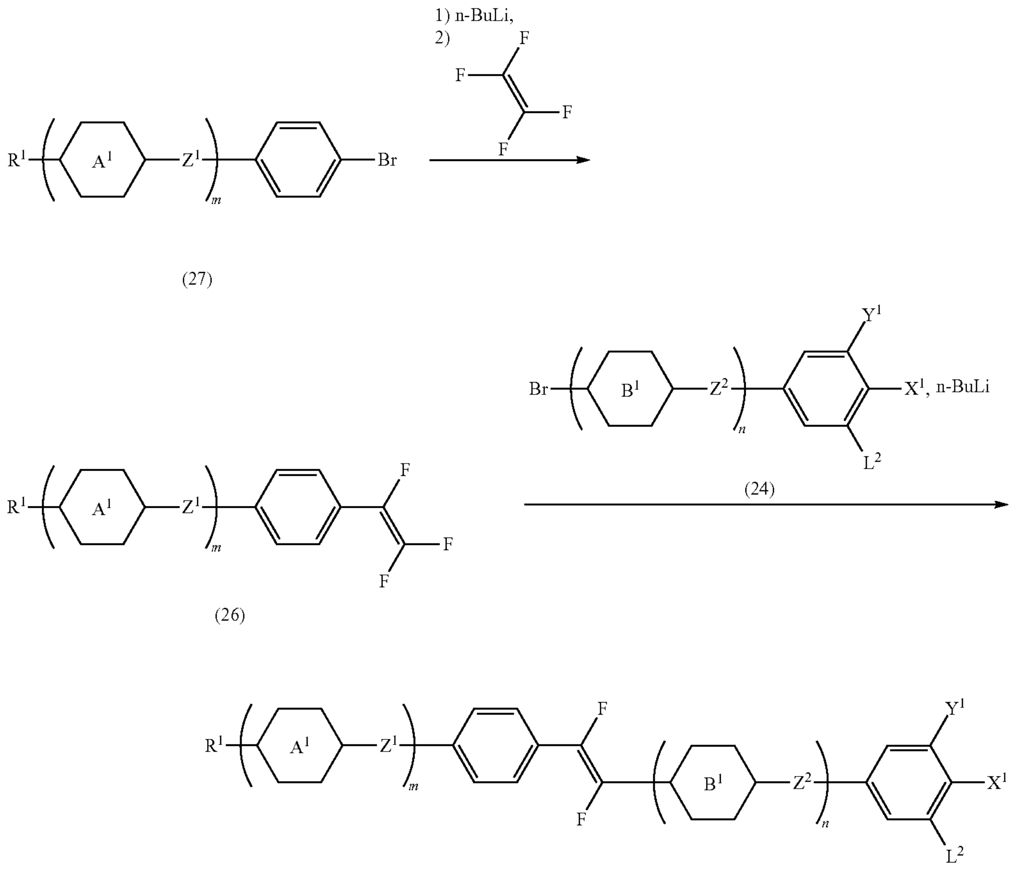

(1-40)

In the formulas, ring $A^1$, ring $B^1$, $Z^1$, $Z^2$, $R^1$, $X^1$, m and n are defined in the same way as described in item 1.

2. Composition of the Invention

A second embodiment of the invention concerns a composition containing compound (1), preferably, a liquid crystal composition that can be used for a liquid crystal display device. The composition includes at least two components. Primarily, the composition needs to contain compound (1) as component A. The composition may contain, as other components, a liquid crystal compound that is not described as component A in the specification, or a compound selected from components B, C, D and E as described below. The content of component A is preferably in the range of about 0.1 to about 99% by weight for developing excellent characteristics.

Component B is at least one compound selected from the group including compounds (2), (3) and (4). Component C is at least one compound selected from the group including compound (5). Component D is at least one compound selected from the group including compounds (6), (7), (8), (9) and (10).

Component E is at least one compound selected from the group including compounds (11), (12) and (13). The threshold voltage, the temperature range of the liquid crystal phase, the refractive index anisotropy, the dielectric anisotropy, the viscosity and so forth of the composition can be adjusted by mixing component E.

The compound as the component of the liquid crystal composition may be a compound rich in an isotropic element in place of a naturally occurring element. For example, even an analog in which hydrogen is replaced by deuterium has no significant difference in physical characteristics.

Among types of component B, preferred compound (2) includes compound (2-1) to compound (2-16), preferred compound (3) includes compound (3-1) to compound (3-112), and preferred compound (4) includes compound (4-1) to compound (4-52).

(2-1)

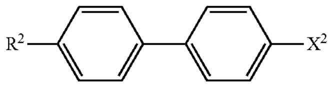

(2-2)

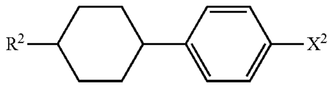

(2-3)

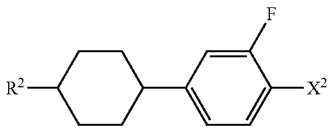

(2-4)

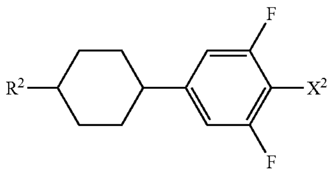

-continued (2-5)

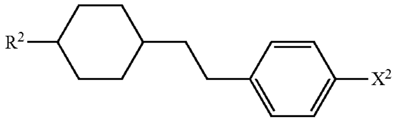

(2-6)

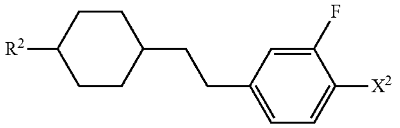

(2-7)

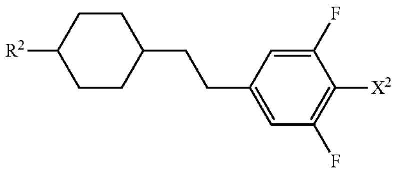

(2-8)

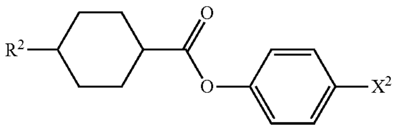

(2-9)

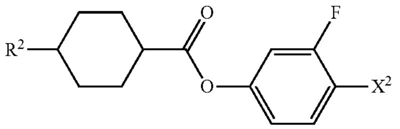

(2-10)

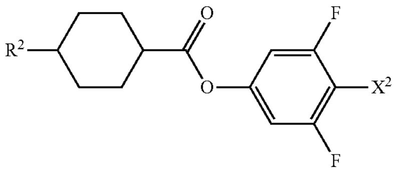

(2-11)

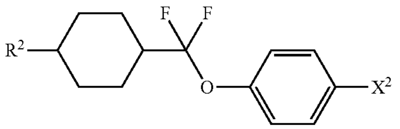

(2-12)

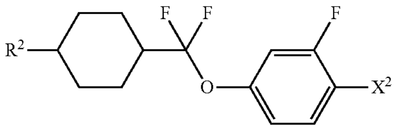

(2-13)

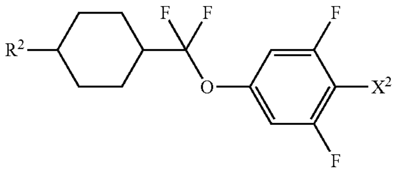

(2-14)

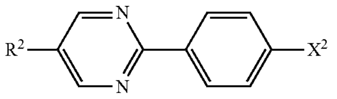

(2-15)

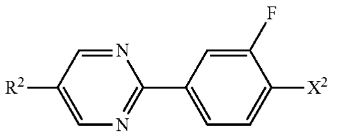

-continued
(2-16)
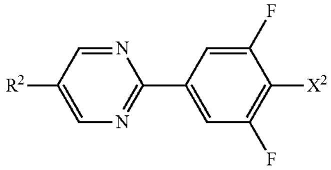
(3-1)
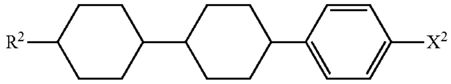
(3-2)
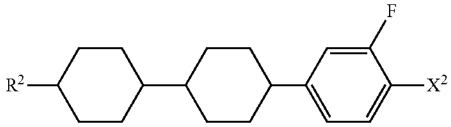
(3-3)
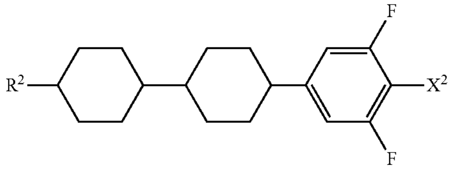
(3-4)
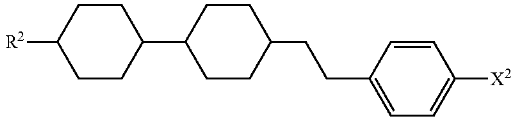
(3-5)
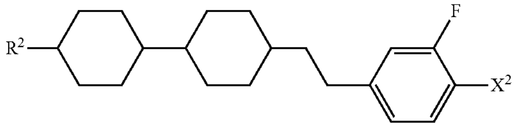
(3-6)
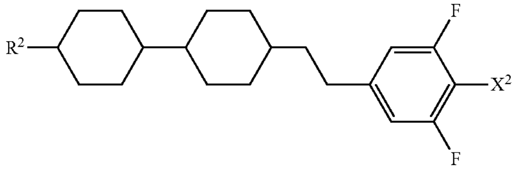
(3-7)
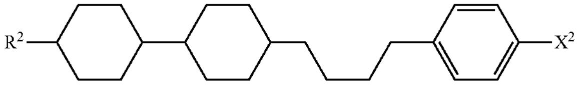
(3-8)
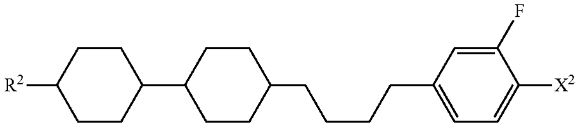
(3-9)
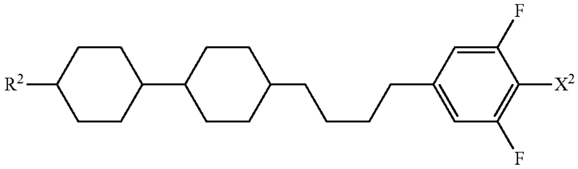
-continued
(3-10)
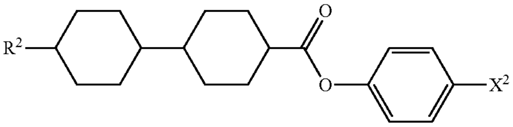
(3-11)
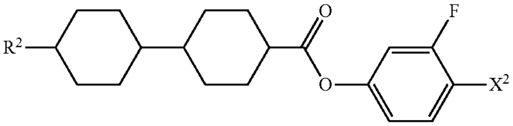
(3-12)
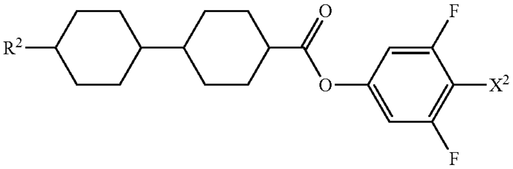
(3-13)
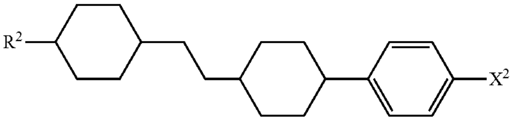
(3-14)
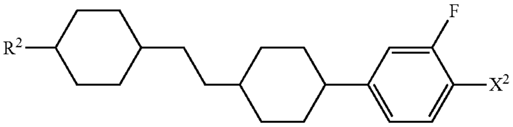
(3-15)
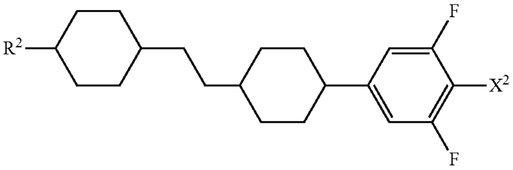
(3-16)
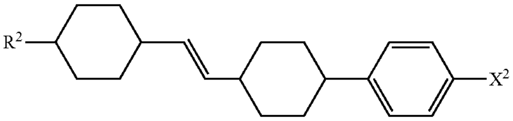
(3-17)
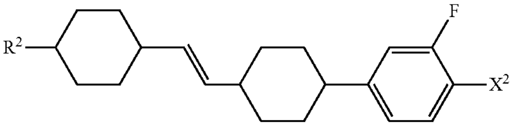
(3-18)
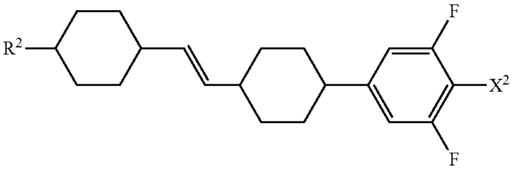

-continued
(3-19)
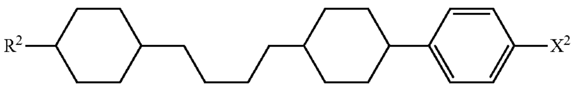
(3-20)
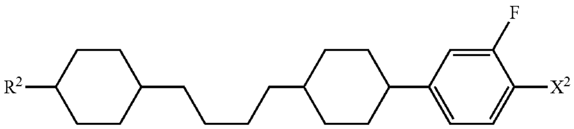
(3-21)
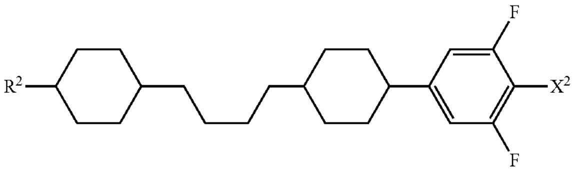
(3-22)
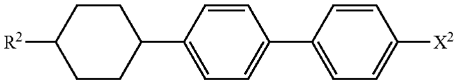
(3-23)
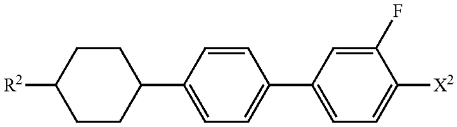
(3-24)
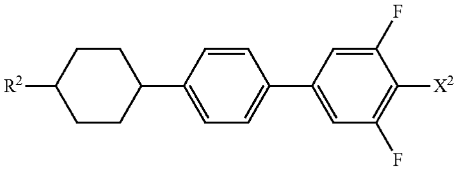
(3-25)
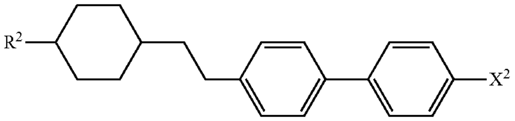
(3-26)
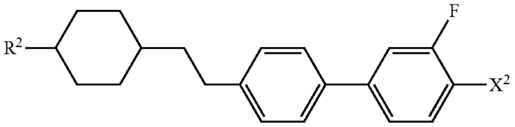
(3-27)
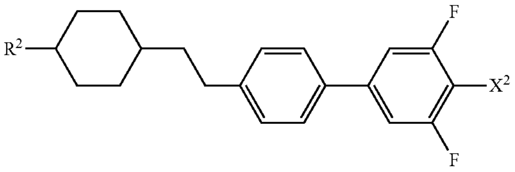
(3-28)
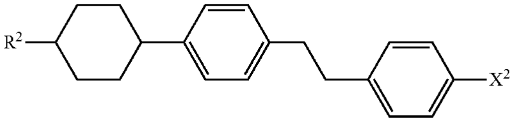
-continued
(3-29)
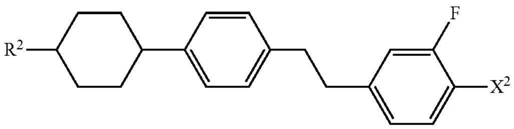
(3-30)
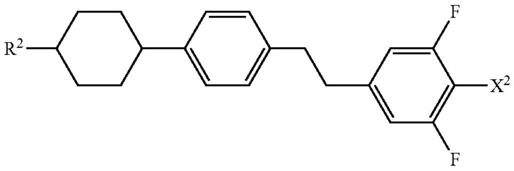
(3-31)
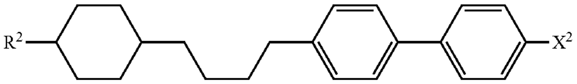
(3-32)
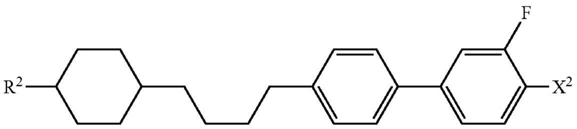
(3-33)
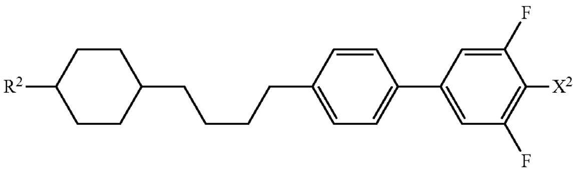
(3-34)
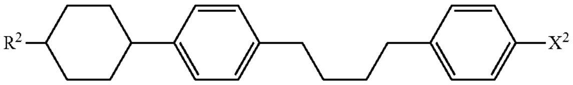
(3-35)
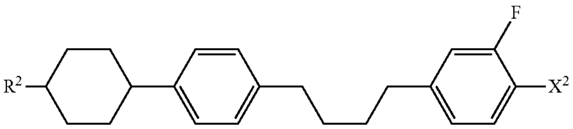
(3-36)
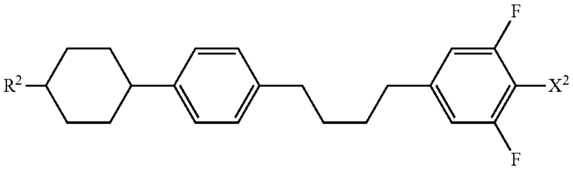
(3-37)
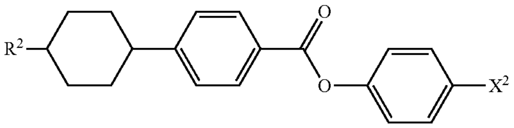
(3-38)
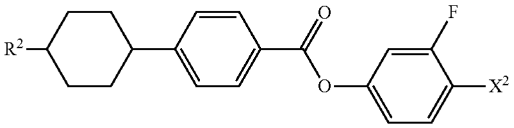

-continued
(3-39)
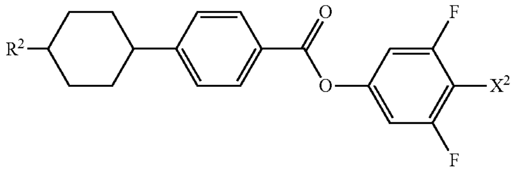
(3-40)
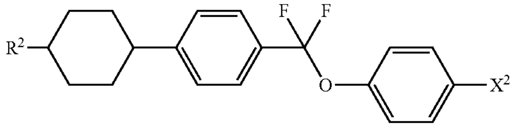
(3-41)
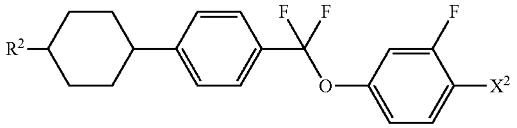
(3-42)
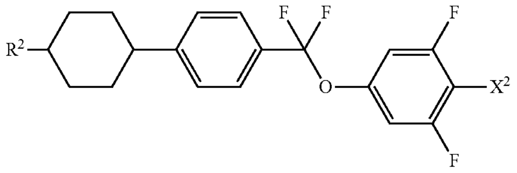
(3-43)
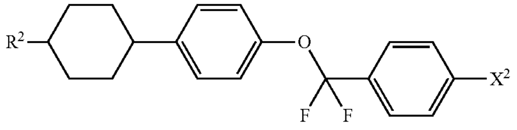
(3-44)
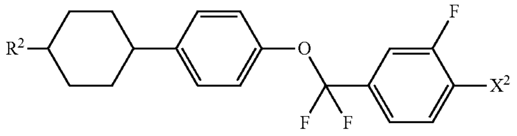
(3-45)
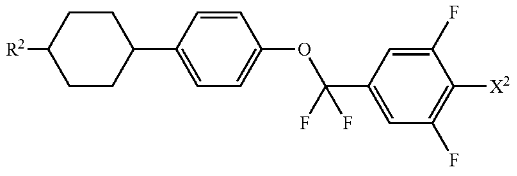
(3-46)
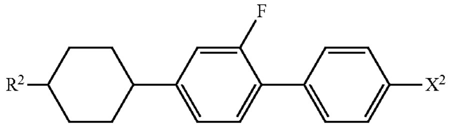
(3-47)
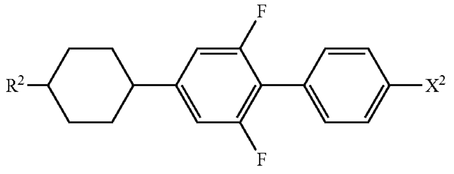
-continued
(3-48)
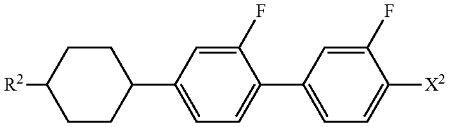
(3-49)
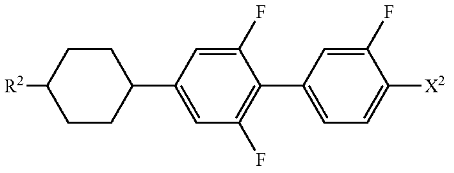
(3-50)
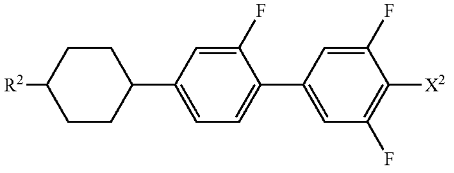
(3-51)
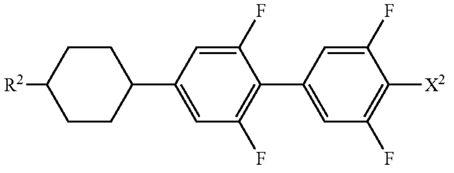
(3-52)
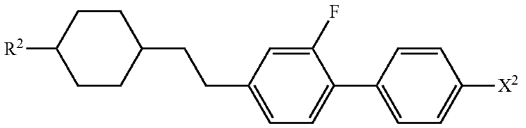
(3-53)
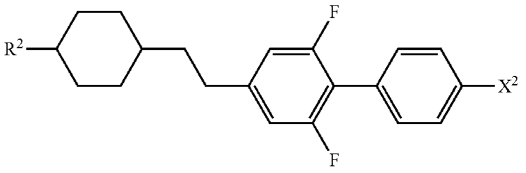
(3-54)
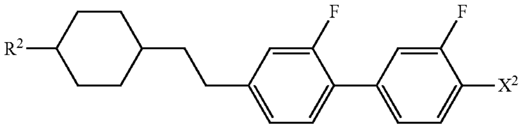
(3-55)
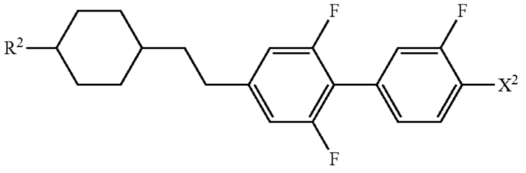
(3-56)
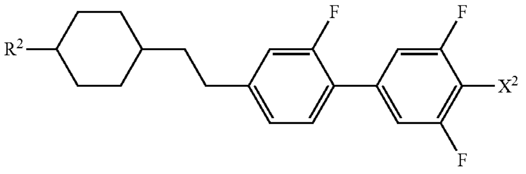

-continued
(3-57)
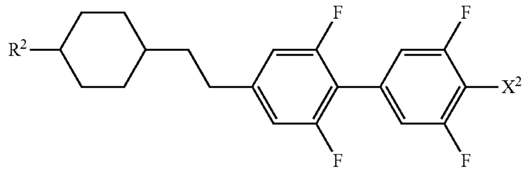
(3-58)
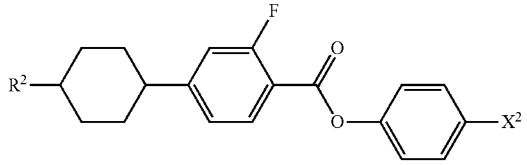
(3-59)
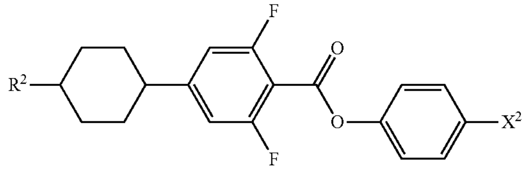
(3-60)
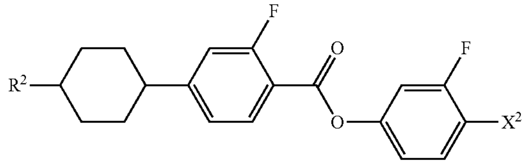
(3-61)
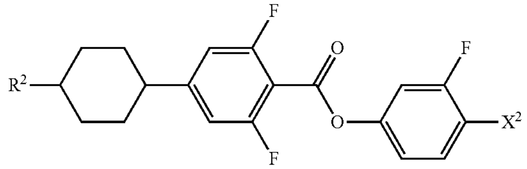
(3-62)
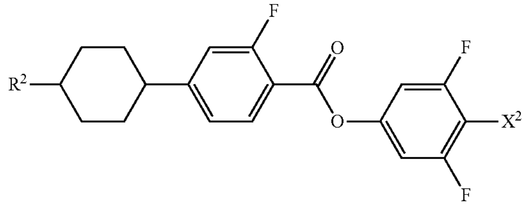
(3-63)
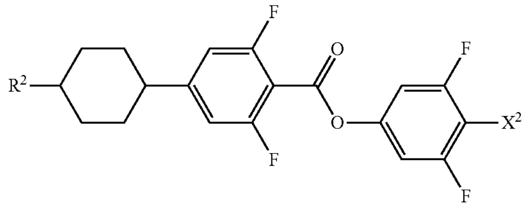
(3-64)
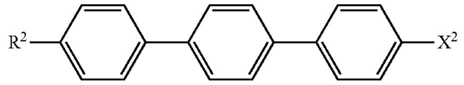
-continued
(3-65)
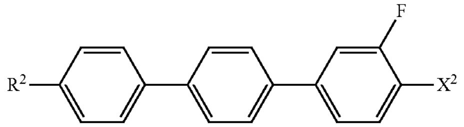
(3-66)
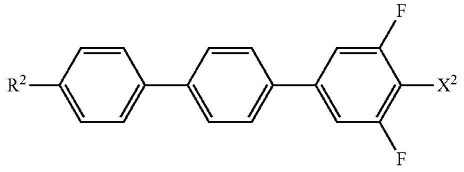
(3-67)
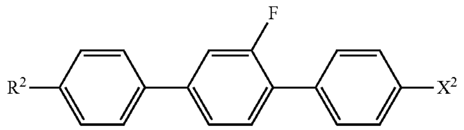
(3-68)
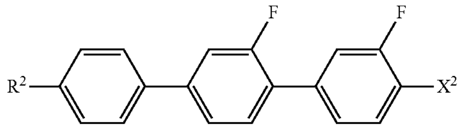
(3-69)
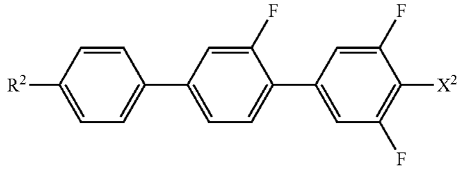
(3-70)
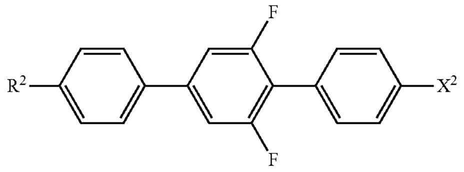
(3-71)
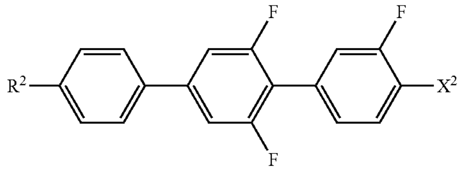
(3-72)
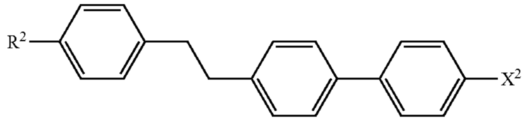
(3-73)
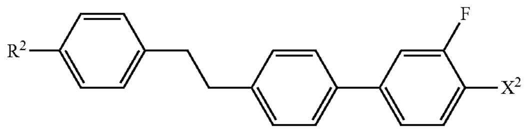

-continued
(3-74)
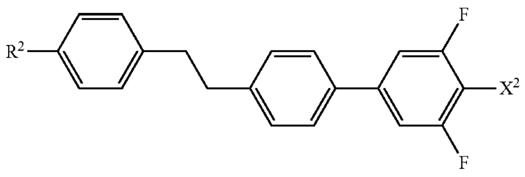
(3-75)
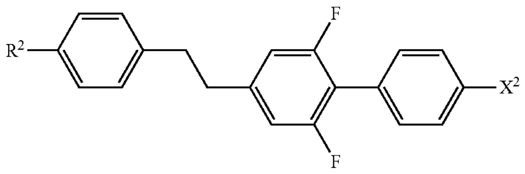
(3-76)
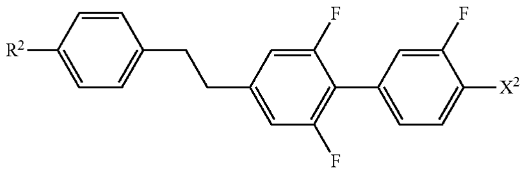
(3-77)
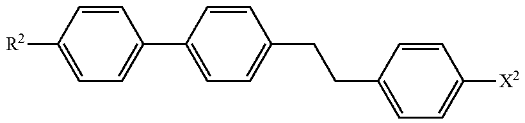
(3-78)
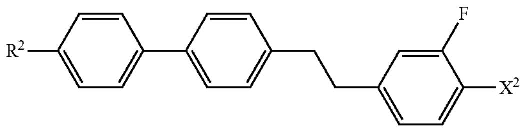
(3-79)
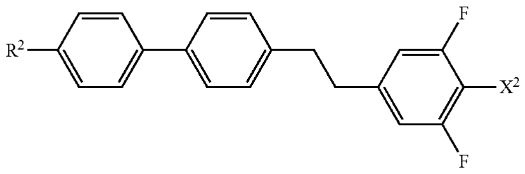
(3-80)
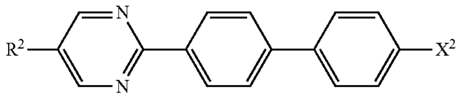
(3-81)
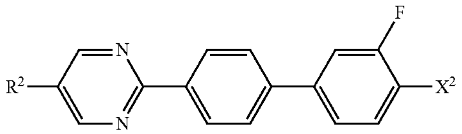
(3-82)
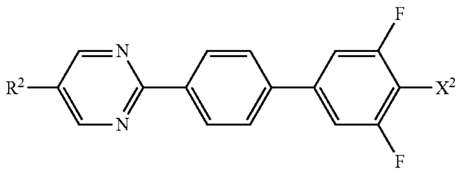
-continued
(3-83)
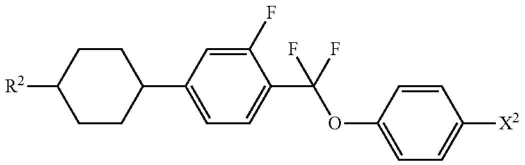
(3-84)
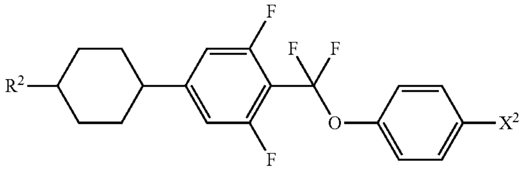
(3-85)
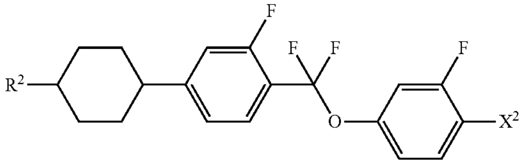
(3-86)
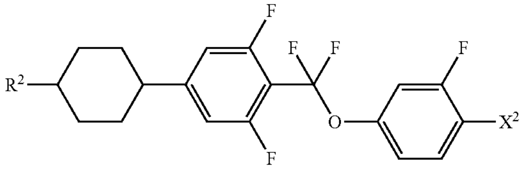
(3-87)
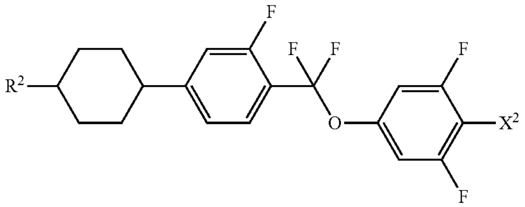
(3-88)
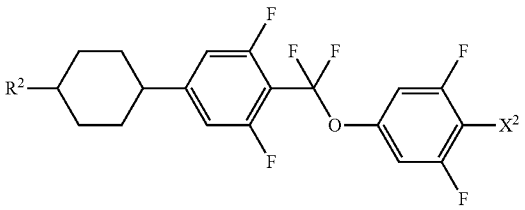
(3-89)
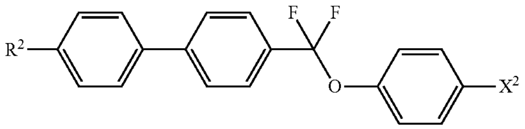
(3-90)
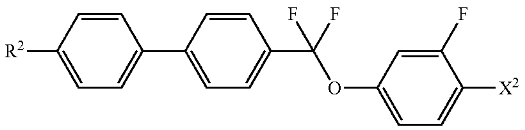

-continued
(3-91)
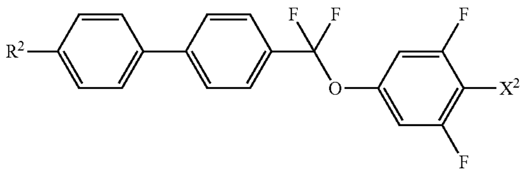
(3-92)
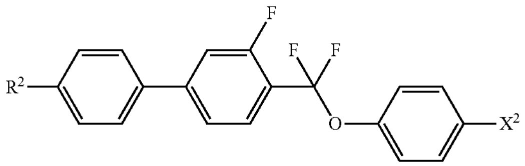
(3-93)
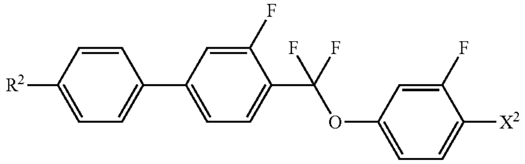
(3-94)
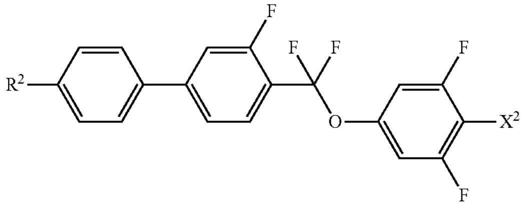
(3-95)
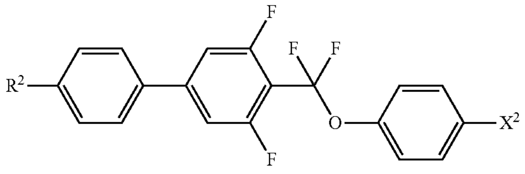
(3-96)
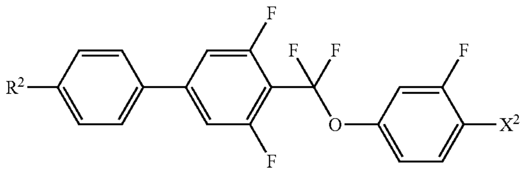
(3-97)
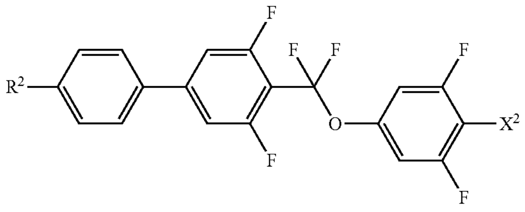
(3-98)
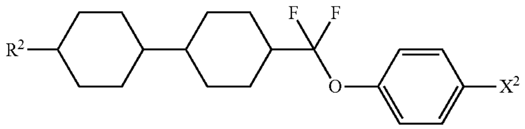
-continued
(3-99)
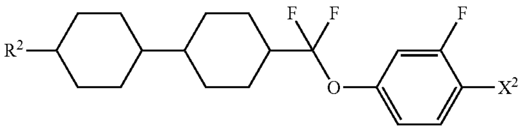
(3-100)
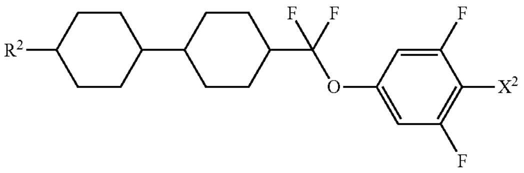
(3-101)
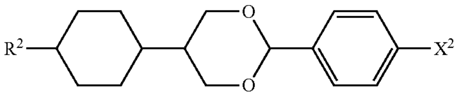
(3-102)
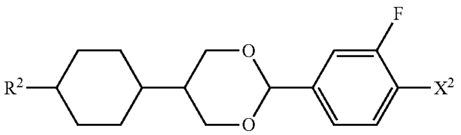
(3-103)
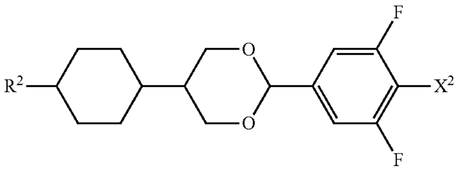
(3-104)
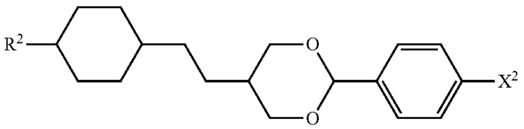
(3-105)
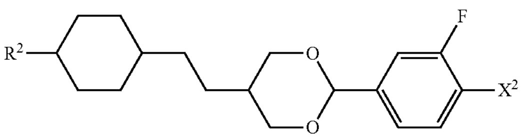
(3-106)
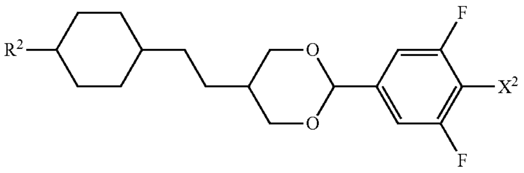
(3-107)
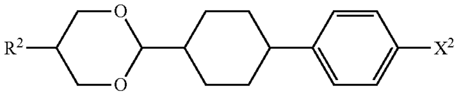
(3-108)
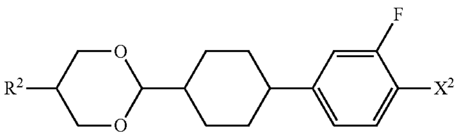

-continued
(3-109)
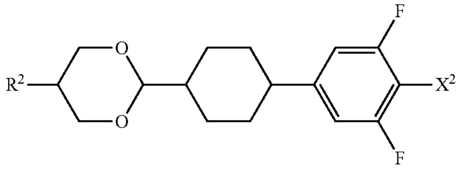
(3-110)
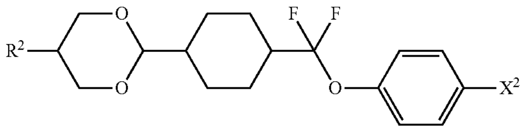
(3-111)
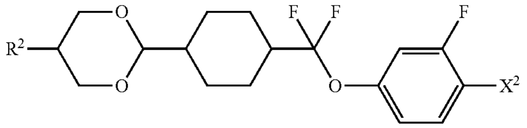
(3-112)
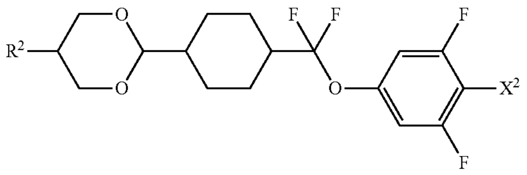
(4-1)
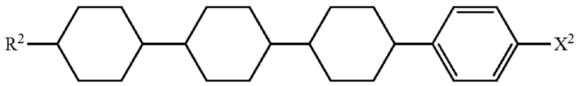
(4-2)
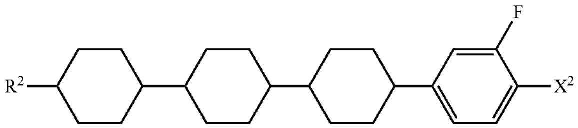
(4-3)
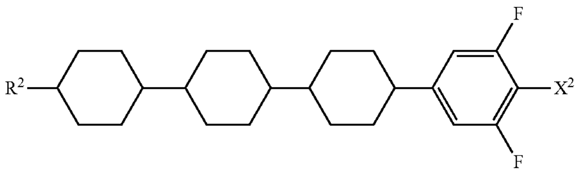
(4-4)
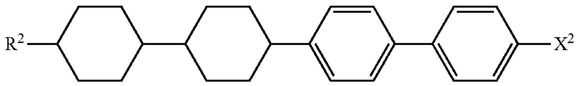
(4-5)
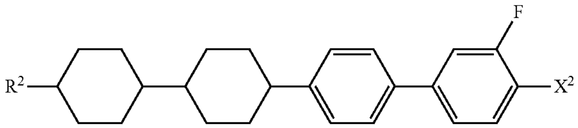
-continued
(4-6)
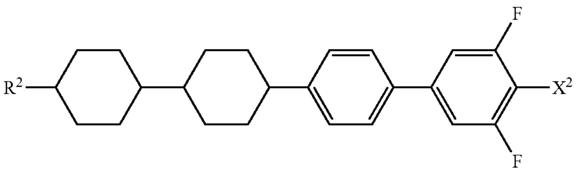
(4-7)
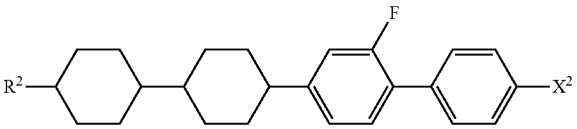
(4-8)
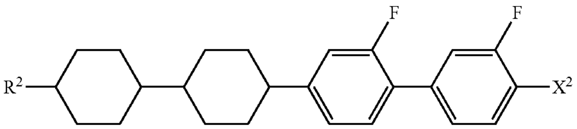
(4-9)
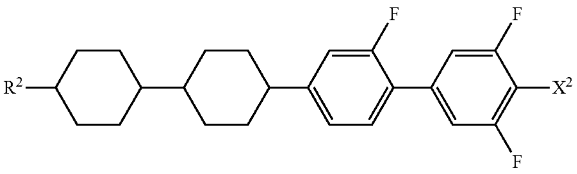
(4-10)
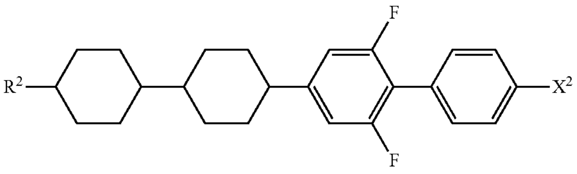
(4-11)
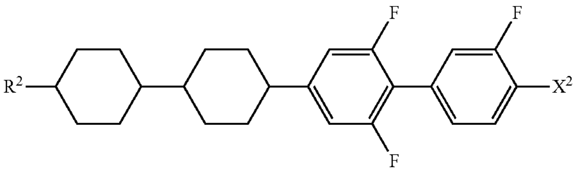
(4-12)
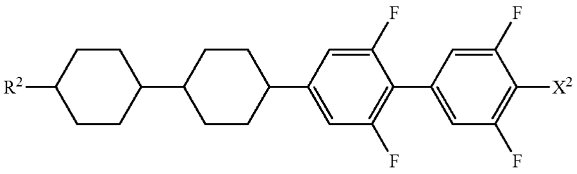
(4-13)
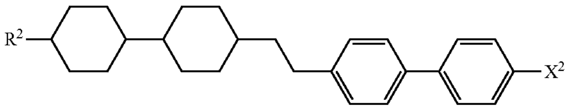
(4-14)
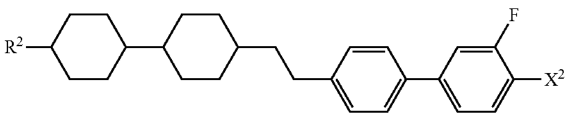

-continued
(4-15)
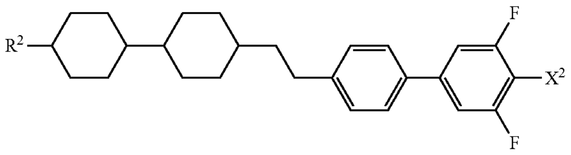
(4-16)
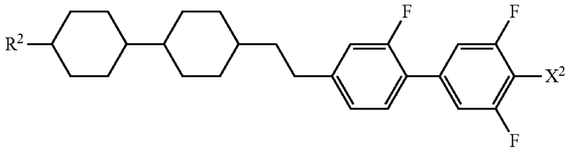
(4-17)
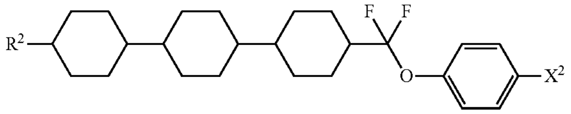
(4-18)
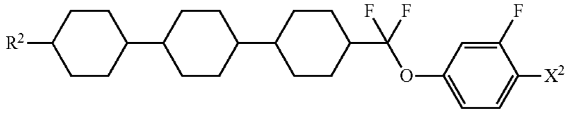
(4-19)
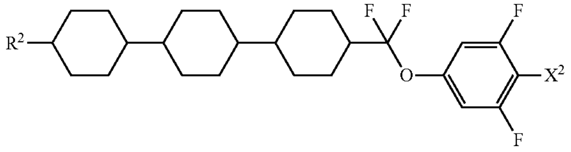
(4-20)
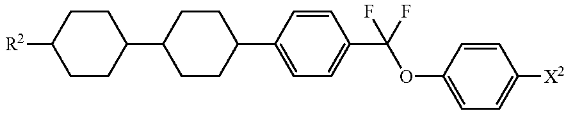
(4-21)
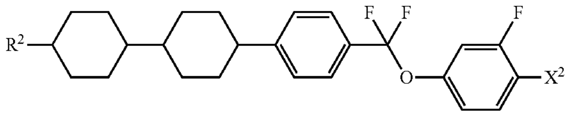
(4-22)
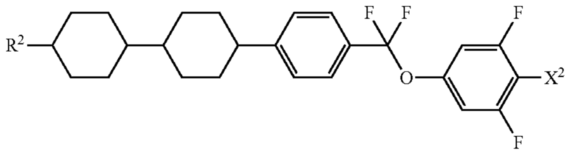
(4-23)
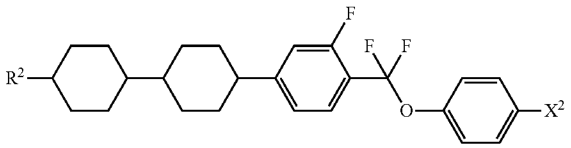
-continued
(4-24)
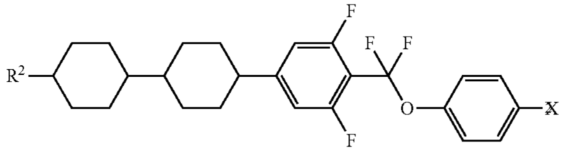
(4-25)
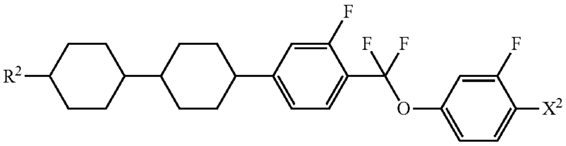
(4-26)
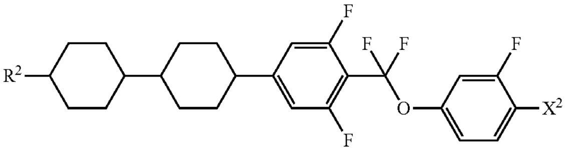
(4-27)
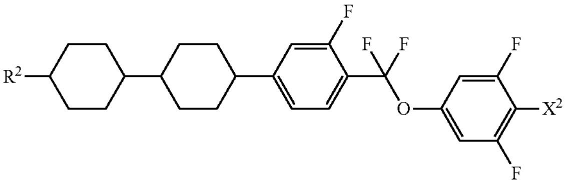
(4-28)
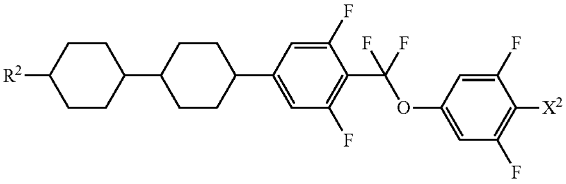
(4-29)
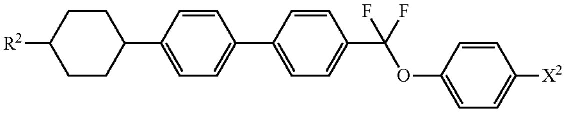
(4-30)
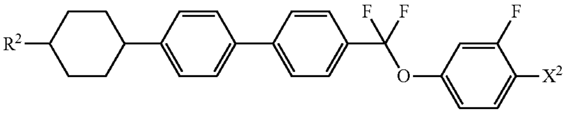
(4-31)
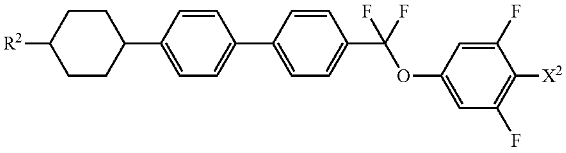
(4-32)
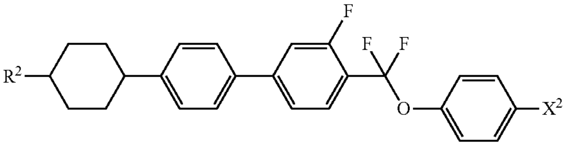

-continued
(4-33)
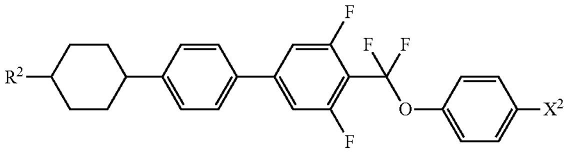
(4-34)
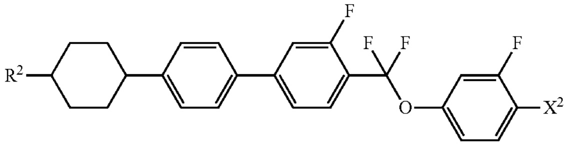
(4-35)
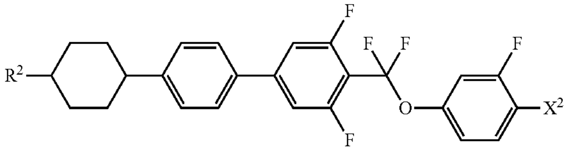
(4-36)
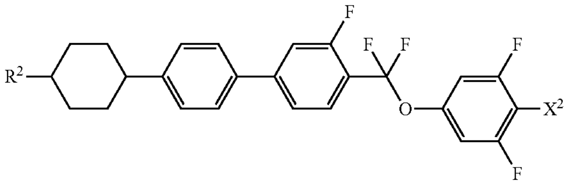
(4-37)
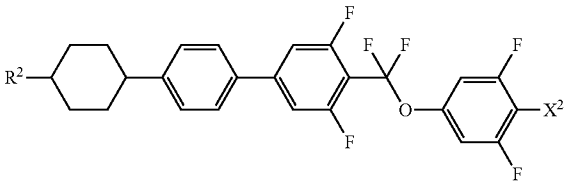
(4-38)
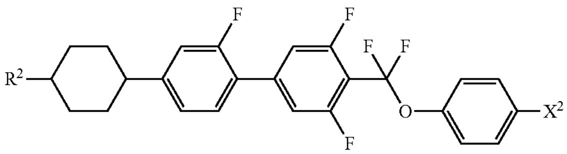
(4-39)
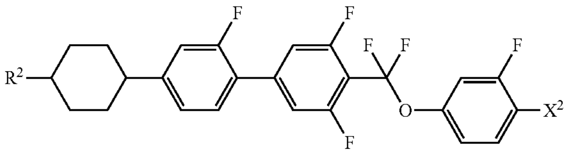
(4-40)
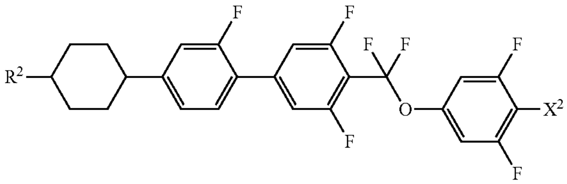
-continued
(4-41)
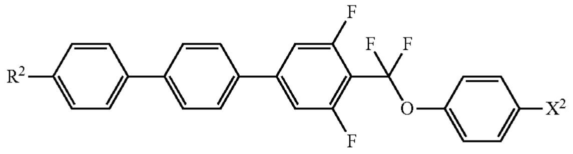
(4-42)
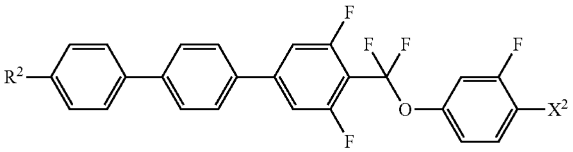
(4-43)
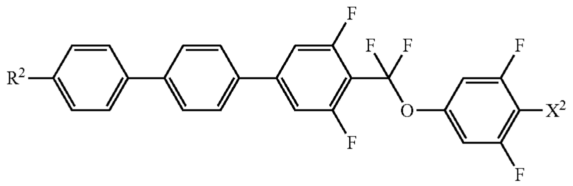
(4-44)
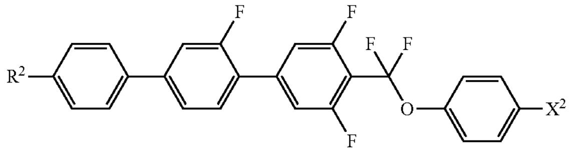
(4-45)
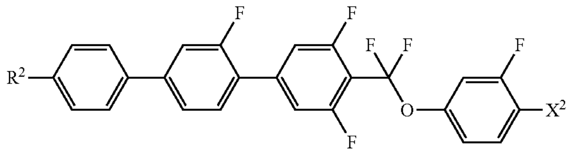
(4-46)
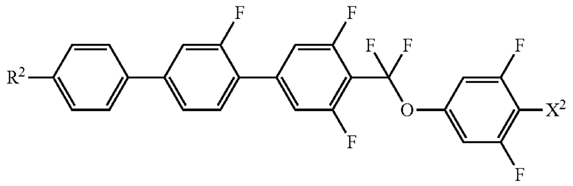
(4-47)
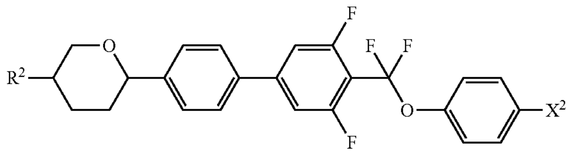
(4-48)
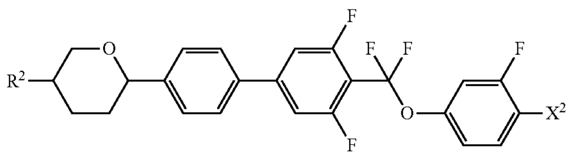

-continued (4-49)

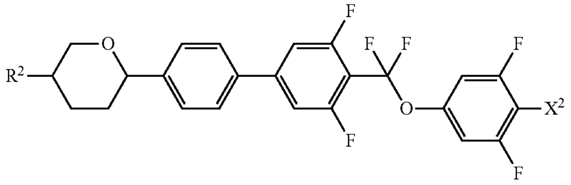

(4-50)

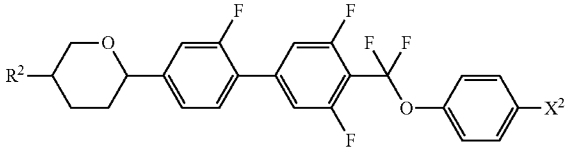

(4-51)

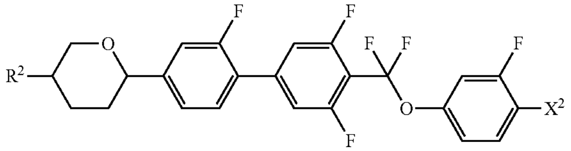

(4-52)

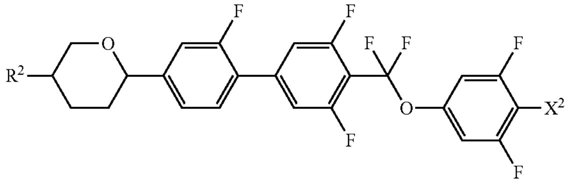

In the formulas, $R^2$ and $X^2$ are defined in the same way as described previously.

Component B has a positive dielectric anisotropy and an exceptional thermal stability and chemical stability, and therefore is used when a composition for TFT is prepared. In order to adjust the viscosity of the composition, the composition preferably further contains component E. The content of component B is suitably in the range of about 1 to about 99% by weight, preferably, about 10 to about 97% by weight, further preferably, about 40 to about 95% by weight, based on the total weight of the composition.

Preferred compound (5) includes compound (5-1) to compound (5-62).

(5-1)

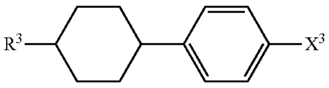

(5-2)

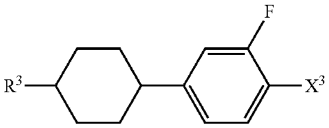

(5-3)

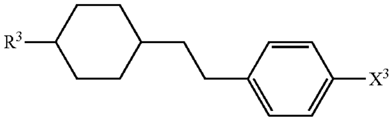

-continued (5-4)

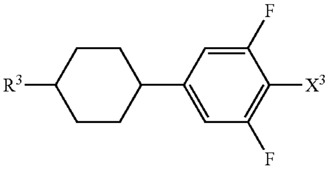

(5-5)

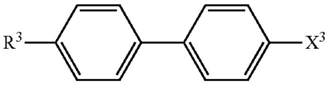

(5-6)

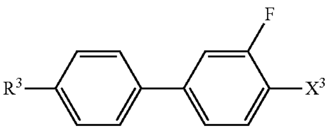

(5-7)

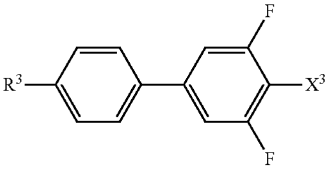

(5-8)

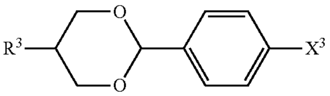

(5-9)

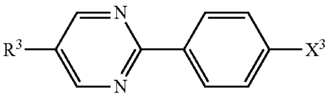

(5-10)

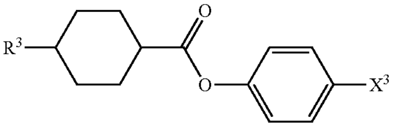

(5-11)

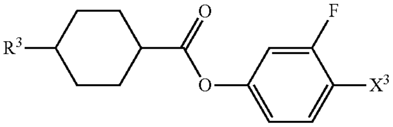

(5-12)

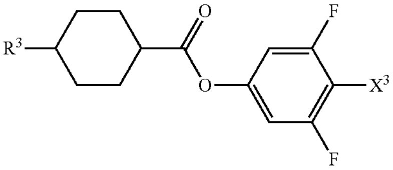

(5-13)

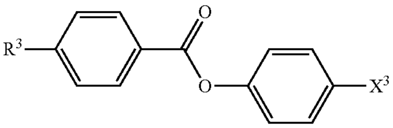

(5-14)

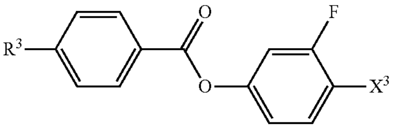

-continued
(5-15)
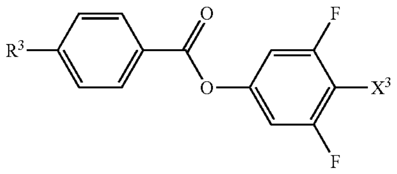
(5-16)
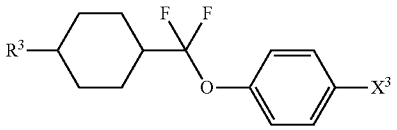
(5-17)
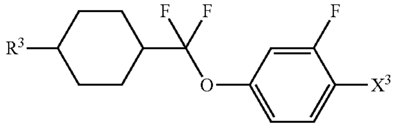
(5-18)
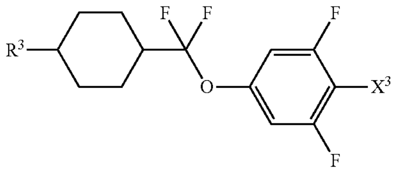
(5-19)
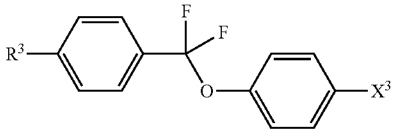
(5-20)
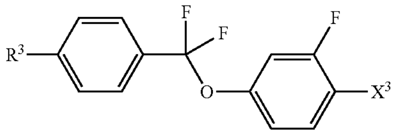
(5-21)
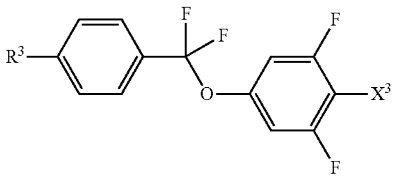
(5-22)
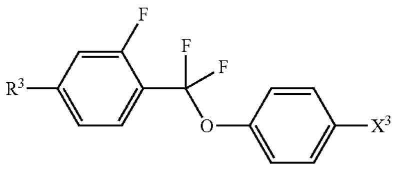
(5-23)
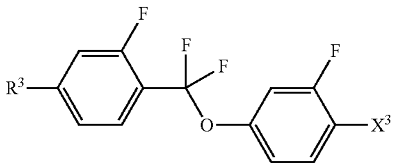
-continued
(5-24)
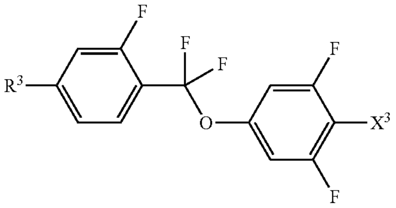
(5-25)
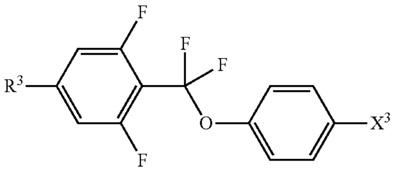
(5-26)
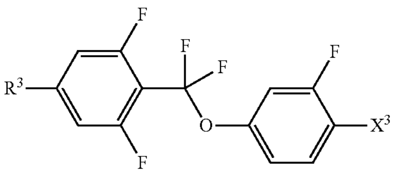
(5-27)
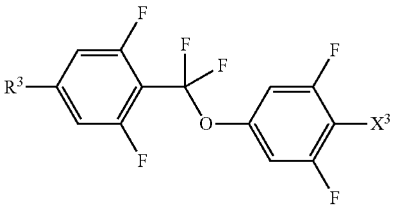
(5-28)
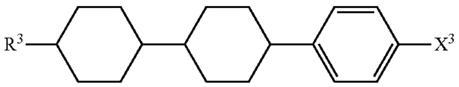
(5-29)
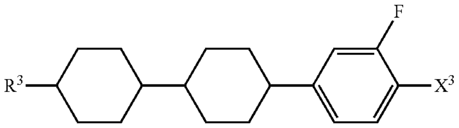
(5-30)
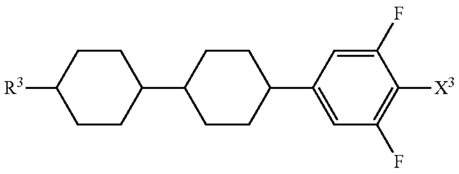
(5-31)
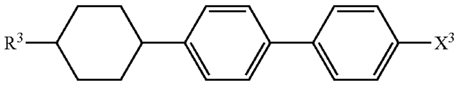
(5-32)
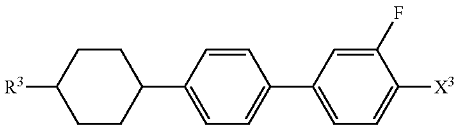
(5-33)
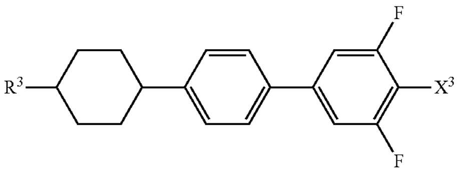

-continued
(5-34)
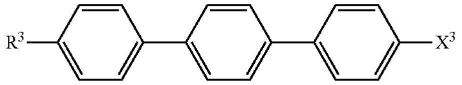
(5-35)
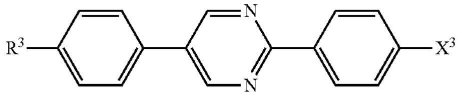
(5-36)
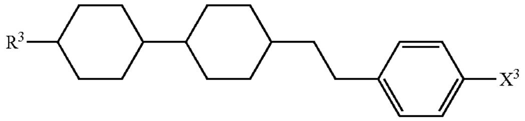
(5-37)
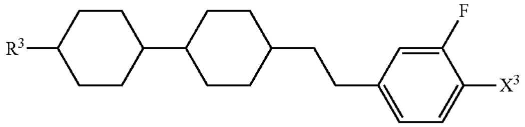
(5-38)
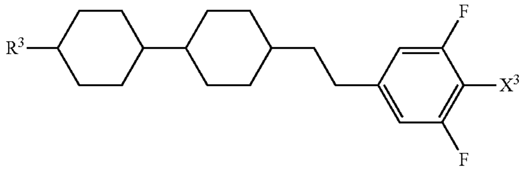
(5-39)
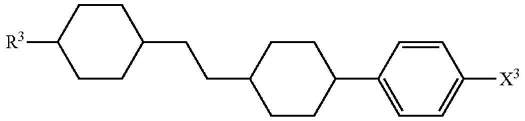
(5-40)
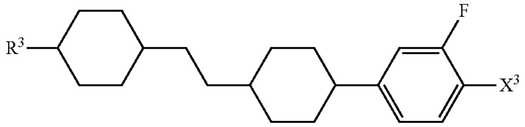
(5-41)
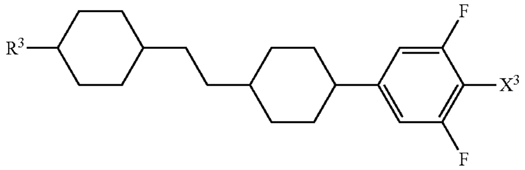
(5-42)
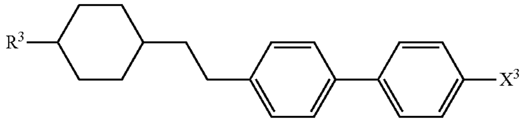
(5-43)
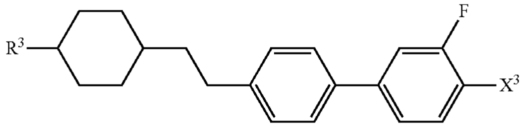
-continued
(5-44)
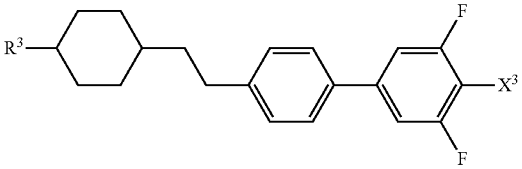
(5-45)
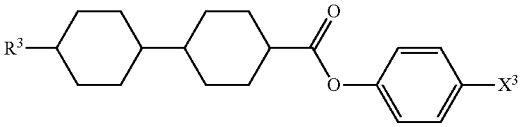
(5-46)
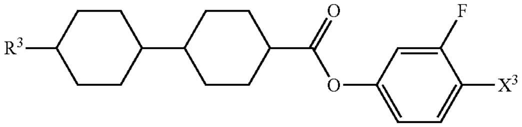
(5-47)
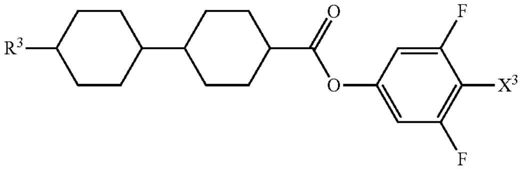
(5-48)
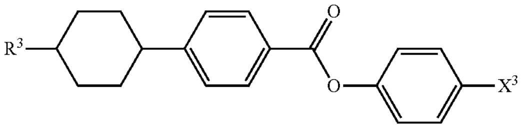
(5-49)
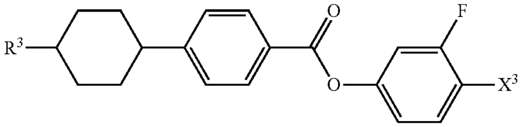
(5-50)
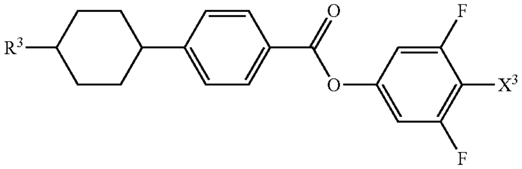
(5-51)
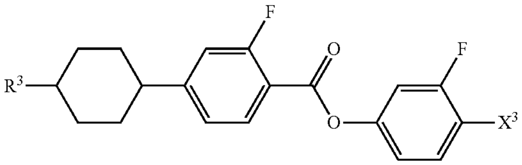
(5-52)
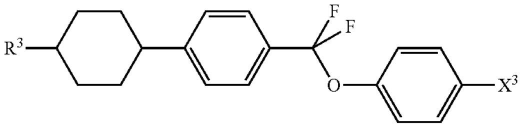

-continued (5-53)

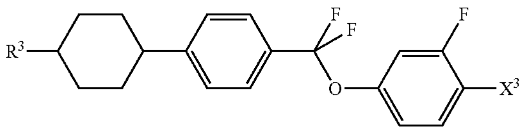

(5-54)

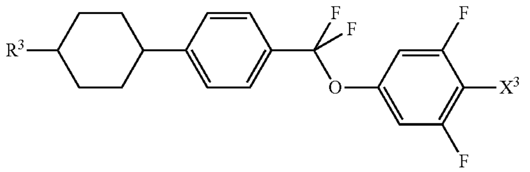

(5-55)

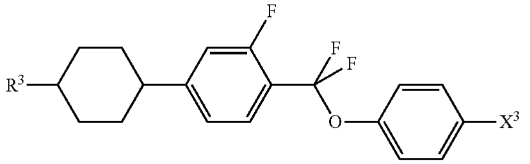

(5-56)

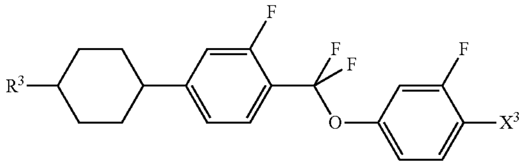

(5-57)

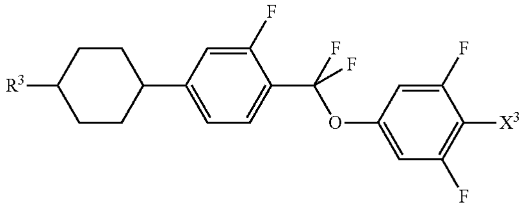

(5-58)

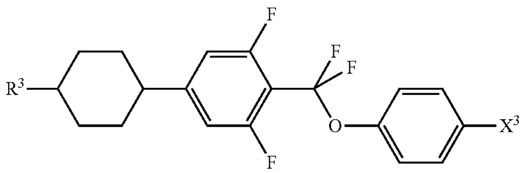

(5-59)

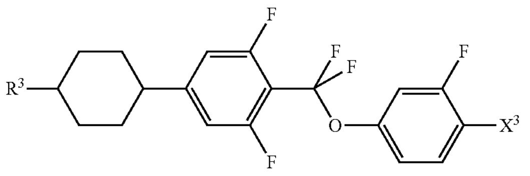

(5-60)

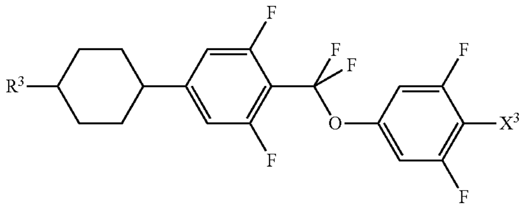

-continued (5-61)

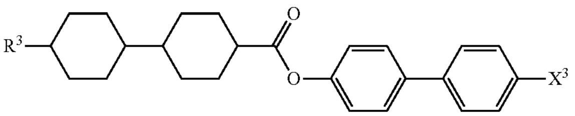

(5-62)

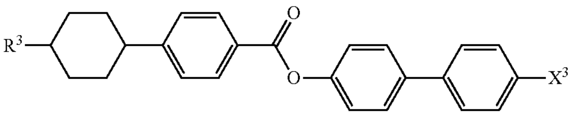

In the formulas, $R^3$ and $X^3$ are defined in the same way as described previously.

Compound (5), namely, component C has a very large positive dielectric anisotropy, and therefore is mainly used when a liquid crystal composition for STN or TN is prepared. Component C can decrease the threshold voltage of the composition. Component C can adjust the viscosity and the refractive index anisotropy, and extend the temperature range of the liquid crystal phase. Furthermore, the component C can also be used for improvement of steepness.

When the composition for STN or TN is prepared, the content of component C is in the range of about 0.1 to about 99.9% by weight, preferably, about 10 to about 97% by weight, further preferably, about 40 to about 95% by weight, based on the total weight of the composition. Moreover, the threshold voltage, the temperature range of the liquid crystal phase, the refractive index anisotropy, the dielectric anisotropy, the viscosity and so forth can be adjusted by further mixing the component described later.

Component D including at least one compound selected from the group including compound (6) to compound (10) is preferred when a composition having a negative dielectric anisotropy to be used in a VA device and so forth is prepared.

Preferred compound (6) to compound (10) include compound (6-1) to compound (6-5), compound (7-1) to compound (7-11), compound (8-1) and compound (10-1) to compound (10-11).

(6-1)

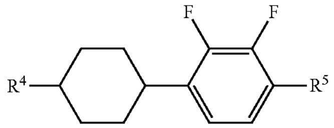

(6-2)

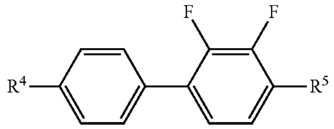

(6-3)

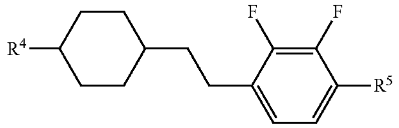

(6-4)

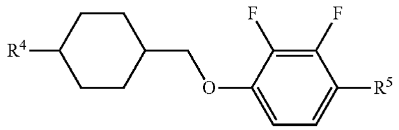

-continued
(6-5)
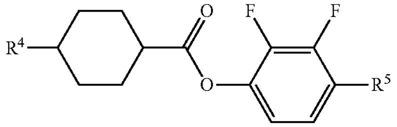
(7-1)
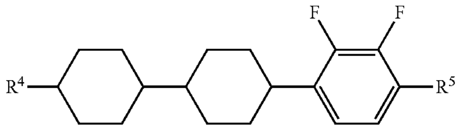
(7-2)
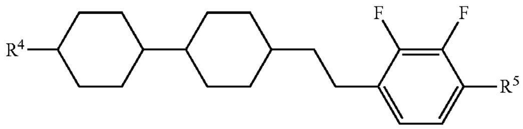
(7-3)
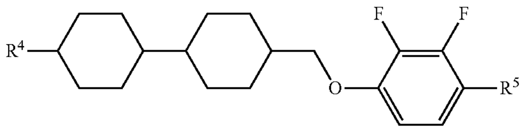
(7-4)
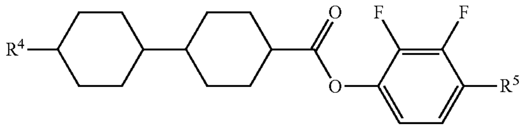
(7-5)
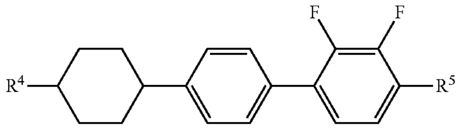
(7-6)
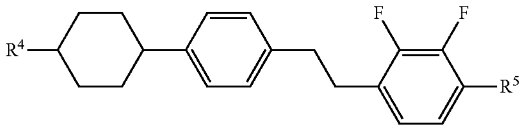
(7-7)
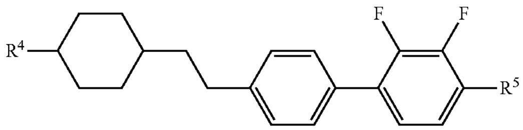
(7-8)
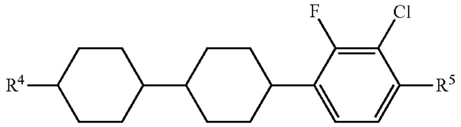
(7-9)
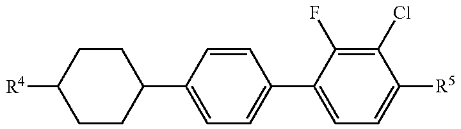
(7-10)
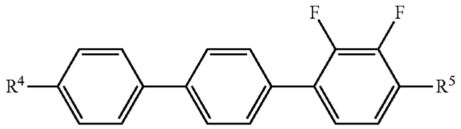
-continued
(7-11)
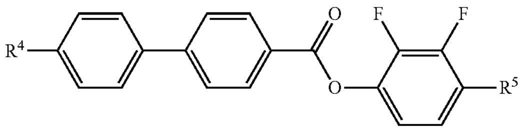
(8-1)
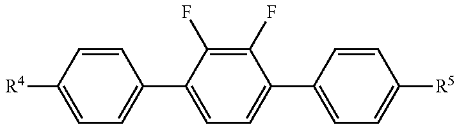
(10-1)
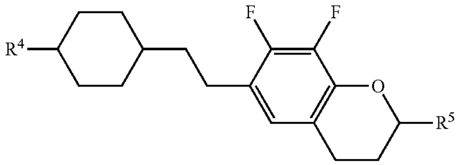
(10-2)
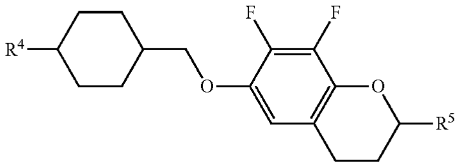
(10-3)
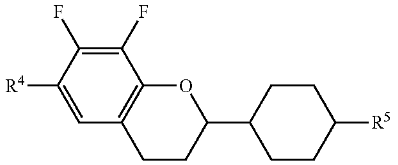
(10-4)
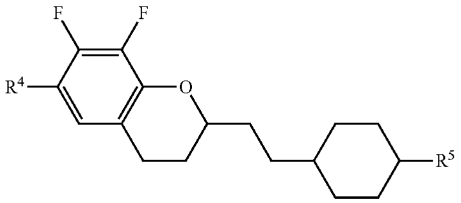
(10-5)
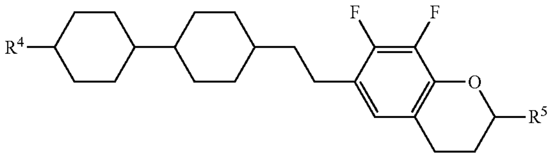
(10-6)
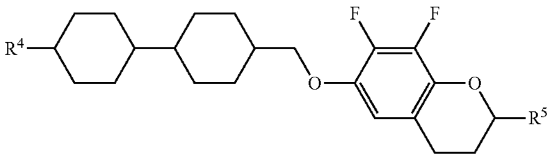
(10-7)
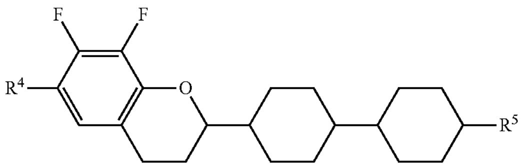

-continued (10-8)

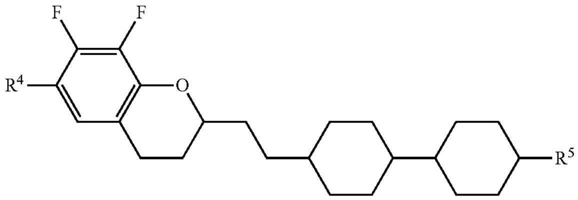

(10-9)

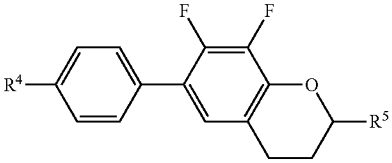

(10-10)

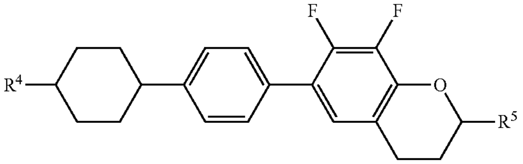

(10-11)

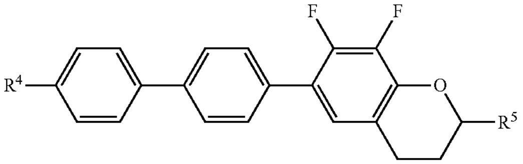

In the formulas, $R^4$ and $R^5$ are defined in the same way as described previously.

Component D is mainly used for the composition having the negative dielectric anisotropy for the VA device. When the content of component D is increased, the threshold voltage of the composition is decreased but the viscosity is increased. Accordingly, the content is preferably decreased as long as a desired value of the threshold voltage is satisfied. The content is preferably about 40% by weight or more for driving the device at a low voltage because an absolute value of the dielectric anisotropy is about 5.

Among types of component D, compound (6) is a two-ring compound, and therefore is effective mainly in adjusting the threshold voltage, the viscosity or the refractive index anisotropy. Moreover, compound (7) and compound (8) each are a three-ring compound, and therefore are effective in increasing the clearing point, extending a nematic range, decreasing the threshold voltage, increasing the refractive index anisotropy and so forth.

When the composition for the VA device is prepared, the content of component D is preferably about 40% by weight or more, further preferably, in the range of about 50 to about 95% by weight, based on the total weight of the composition. An elastic constant or a voltage-transmission curve can be controlled by mixing component D. When component D is mixed with the composition having the positive dielectric anisotropy, the content of component D is preferably about 30% by weight or less based on the total weight of the composition.

Preferred compound (11), compound (12) and compound (13) include compound (11-1) to compound (11-11), compound (12-1) to compound (12-18) and compound (13-1) to compound (13-6).

(11-1)

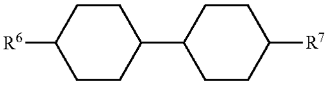

(11-2)

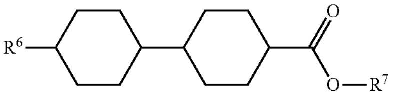

(11-3)

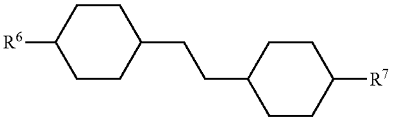

(11-4)

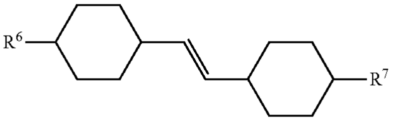

(11-5)

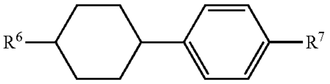

(11-6)

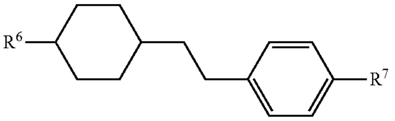

(11-7)

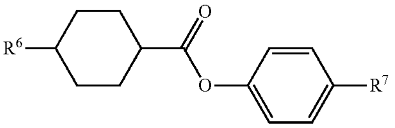

(11-8)

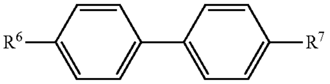

(11-9)

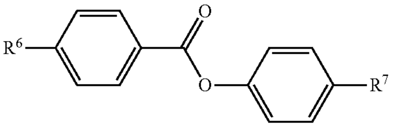

(11-10)

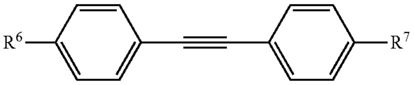

(11-11)

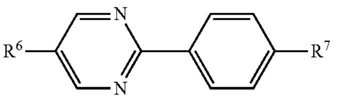

(12-1)

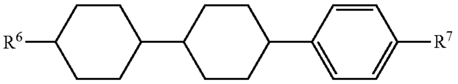

(12-2)

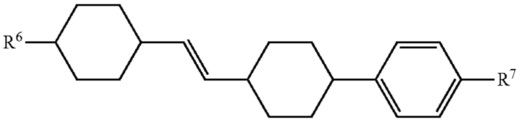

-continued
(12-3)
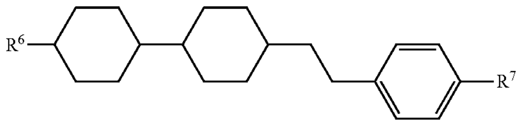
(12-4)
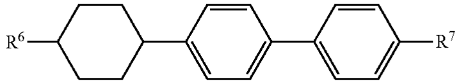
(12-5)
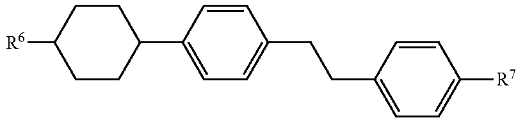
(12-6)
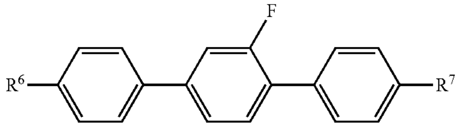
(12-7)
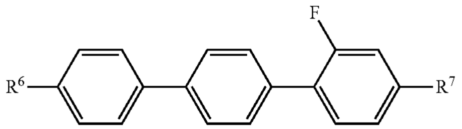
(12-8)
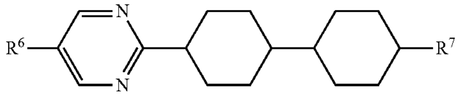
(12-9)
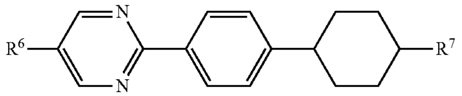
(12-10)
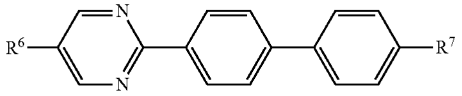
(12-11)
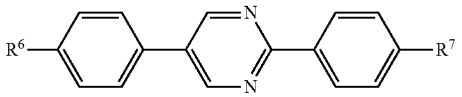
(12-12)
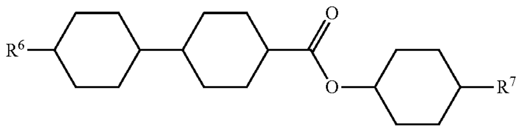
(12-13)
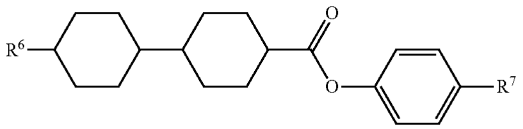
(12-14)
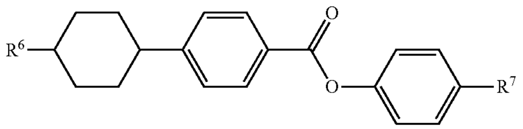
-continued
(12-15)
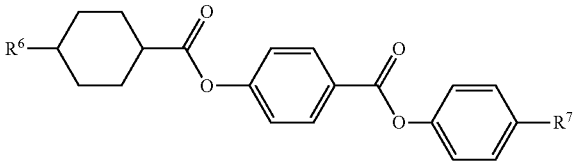
(12-16)
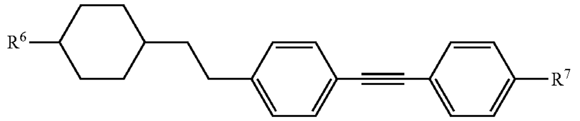
(12-17)
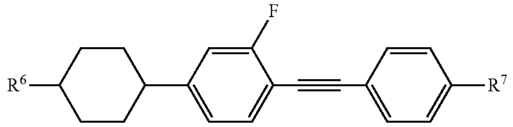
(12-18)
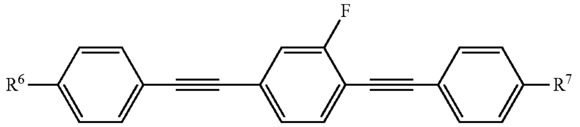
(13-1)
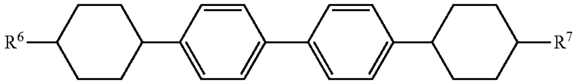
(13-2)
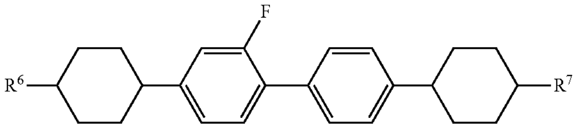
(13-3)
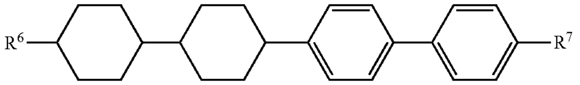
(13-4)
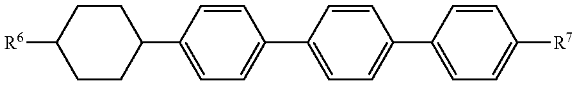
(13-5)
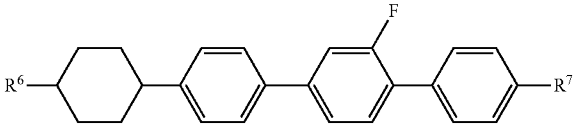
(13-6)
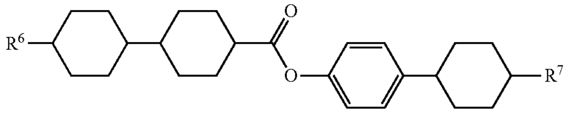
In the formulas, $R^6$ and $R^7$ are defined in the same way as described previously.
Compound (11) to compound (13), namely, component E have a small absolute value of the dielectric anisotropy and are close to neutrality. Compound (11) is effective mainly in adjusting the viscosity or the refractive index anisotropy, and compound (12) and compound (13) are effective in extending a range of the nematic phase to increase the clearing point and so forth, or adjusting the refractive index anisotropy.

When the content of component E is increased, the threshold voltage of the composition is increased and the viscosity is decreased. Accordingly, the content is desirably increased as long as a required value of the threshold voltage of the composition is satisfied. When the liquid crystal composition for TFT is prepared, the content of component E is preferably about 30% by weight or more, further preferably, about 50% by weight or more, based on the total weight of the composition. When the liquid crystal composition for STN or TN is prepared, the content of component E is preferably about 30% by weight or more, further preferably, about 40% by weight or more, based on the total weight of the composition.

The composition is generally prepared according to a publicly known method such as mutual dissolution of necessary components at a high temperature. An additive well-known to a person skilled in the art may be added depending on an intended use. For example, as described later, a composition containing an optically active compound or a composition for a guest host (GH) mode prepared by adding a dye can be prepared. The additive is ordinarily well known to a person skilled in the art, and is described in literatures and so forth in detail.

The composition may further contain one or more optically active compounds.

The optically active compound includes a publicly known chiral dopant. The chiral dopant is effective in inducing a helical structure in liquid crystals, adjusting a necessary twist angle and thus preventing a reverse twist. A preferred chiral dopant includes optically active compound (Op-1) to optically active compound (Op-13) described below.

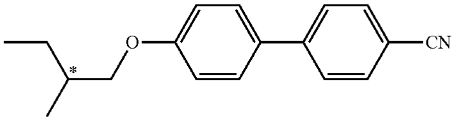
(Op-1)

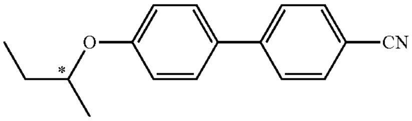
(Op-2)

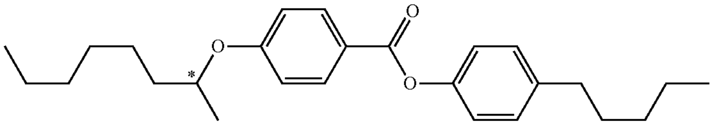
(Op-3)

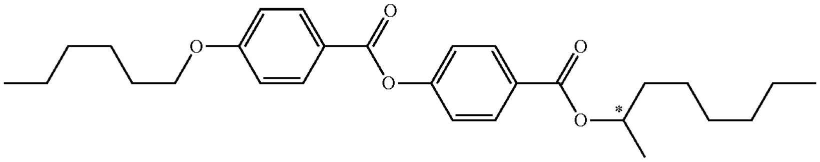
(Op-4)

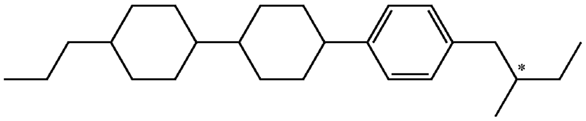
(Op-5)

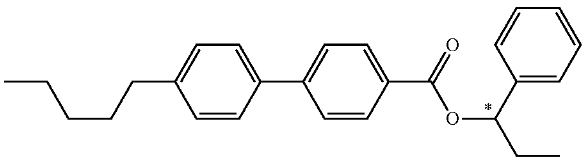
(Op-6)

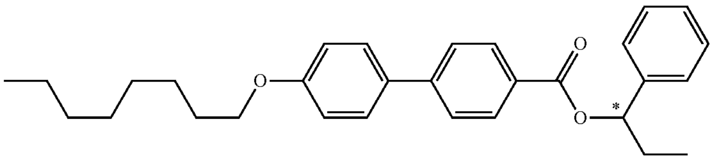
(Op-7)

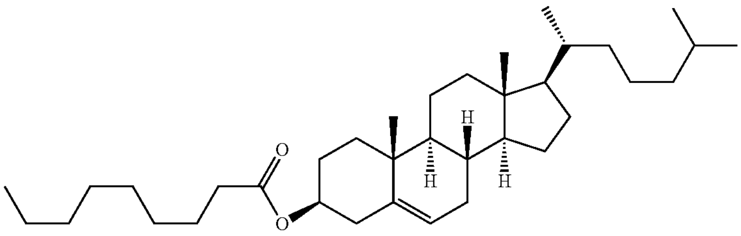
(Op-8)

-continued (Op-9)

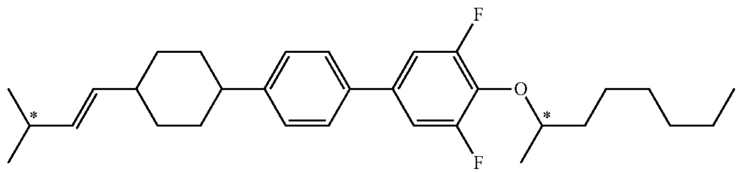

(Op-10)

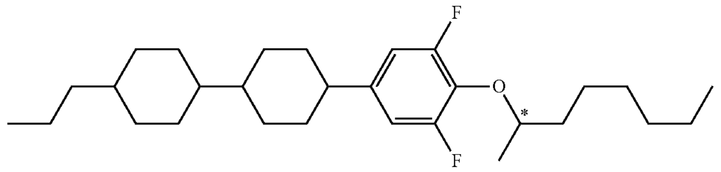

(Op-11)

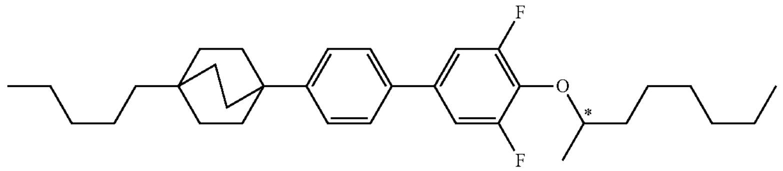

(Op-12)

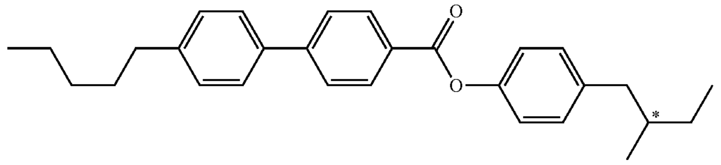

(Op-13)

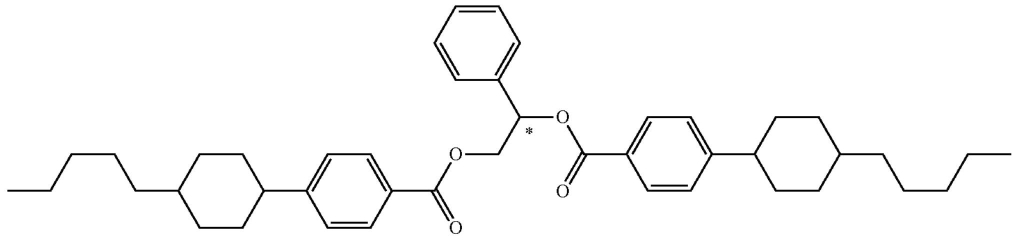

The optically active compound added to the composition adjusts a helical pitch. The helical pitch is preferably adjusted in the range of about 40 to about 200 micrometers in the composition for TFT and TN. The helical pitch is preferably adjusted in the range of about 6 to about 20 micrometers in the composition for STN. The helical pitch is preferably adjusted in the range of about 1.5 to about 4 micrometers in a composition for a bistable TN device. Two or more optically active compounds may be added for the purpose of adjusting temperature dependence of the pitch.

If a dichroic dye such as a merocyanine, stylyl, azo, azomethine, azoxy, quinophthalone, anthraquinone or tetrazine dye is added to the composition, the composition can also be used as the composition for the GH mode.

3. Device of the Invention

A third embodiment of the invention concerns a liquid crystal display device using the composition containing compound (1). An example of the device includes a device having an operating mode as described in the foregoing paragraph of background art. Other examples include an NCAP prepared by microencapsulating nematic liquid crystals, or a polymer dispersed liquid crystal display device (PDLCD) prepared by forming a three-dimensional network polymer in liquid crystals, such as a polymer network liquid crystal display device (PNLCD). A device having a comparatively simple structure is shown in Examples.

EXAMPLES

In the following, the invention will be explained in more detail by way of Examples, but the invention is not limited by the Examples described below. In addition, unless otherwise noted, "%" is expressed in terms of "% by weight."

Because a compound obtained was identified using a nuclear magnetic resonance spectrum obtained according to $^1$H-NMR analysis, a gas chromatogram obtained according to gas chromatography (GC) analysis and so forth, analytical methods will be first explained.

$^1$H-NMR Analysis: As a measuring apparatus, DRX-500 (made by Bruker BioSpin Corporation) was used. A sample prepared in Examples and so forth was dissolved in a deuterated solvent such as $CDCl_3$ in which the sample was soluble, and measurement was carried out under the conditions of room temperature, 500 MHz and 24 times of accumulation. In explaining the nuclear magnetic resonance spectra obtained, s, d, t, q and m stand for a singlet, a doublet, a triplet, a quartet and a multiplet, respectively. Moreover, tetramethylsilane (TMS) was used as an internal standard of chemical shifts (δ).

GC Analysis: As a measuring apparatus, GC-14B Gas Chromatograph made by Shimadzu Corporation was used. As a column, capillary column CBP1-M25-025 (length 25 m, bore 0.22 mm, film thickness 0.25 μm; dimethylpolysiloxane as a stationary liquid phase; non-polar) made by Shimadzu Corporation was used. Helium was used as a carrier gas, and a flow rate was adjusted at 1 milliliter per minute. Temperature in a sample injector was set at 300° C. and temperature of a detector (FID) was set at 300° C.

A sample was dissolved in toluene to prepare a 1% solution, and 1 microliter of the solution was injected into the sample injector.

As a recorder, C-R6A Chromatopac made by Shimadzu Corporation or the equivalent thereof was used. The resulting gas chromatogram shows a retention time of a peak and a value of a peak area corresponding to each of component compounds.

As a solvent for diluting the sample, chloroform or hexane, for example, may also be used. Moreover, as the column, capillary column DB-1 (length 30 m, bore 0.32 mm, film thickness 0.25 μm) made by Agilent Technologies, Inc., HP-1 (length 30 m, bore 0.32 mm, film thickness 0.25 μm) made by Agilent Technologies, Inc., Rtx-1 (length 30 m, bore 0.32 mm, film thickness 0.25 μm) made by Restek Corporation, BP-1 (length 30 m, bore 0.32 mm, film thickness 0.25 μm) made by SGE International Pty. Ltd., and so forth may also be used.

A ratio of the peak areas in the gas chromatogram corresponds to a ratio of the component compounds. In general, weight percent of each of the component compounds in an analytical sample is not completely identical with a percentage of each of the peak areas in the analytical sample. When the columns described above are used in the invention, however, the weight percent of each of the component compounds in the analytical sample corresponds substantially to the percentage of each of the peak areas in the analytical sample because each of correction coefficients is essentially 1 (one). The reason is that no significant difference exists among the correction coefficients of the component compounds.

Samples for Measurement

A sample for measuring physical properties of a compound is used in two kinds of cases: using the compound itself as the sample, and using a mixture of the compound with mother liquid crystals as the sample.

In the case where the sample prepared by mixing the compound with the mother liquid crystals was used, measurement was carried out according to the methods described below. First, the sample was prepared by mixing 15% of the compound obtained and 85% of the mother liquid crystals. Then, extrapolated values were calculated from measured values of the sample obtained, according to an extrapolation method based on the formula shown below. The extrapolated values were described as values of physical properties of the compound.

(Extrapolated value)={100×(measured value of a sample)−(% of mother liquid crystals)×(measured value of mother liquid crystals)}/(% of a compound).

When a smectic phase or crystals precipitated at 25° C. even at the ratio of the compound to the mother liquid crystals, a ratio of the compound to the mother liquid crystals was changed in the order of (10%:90%), (5%:95%) and (1%:99%). The physical properties of the sample were measured at a composition in which the smectic phase or crystals did not precipitate at 25° C. The extrapolated values were determined according to the equation described above, and described as the values of physical properties of the compound.

As the mother liquid crystals used for measurement, a variety of types exist. For example, mother liquid crystals (A) can be used. A composition (%) of mother liquid crystals (A) is as described below.

Mother Liquid Crystals (A):

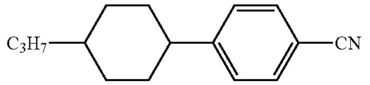

24%

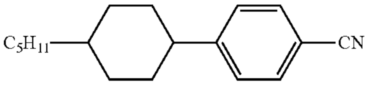

36%

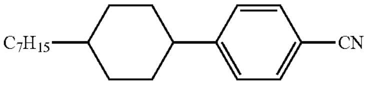

25%

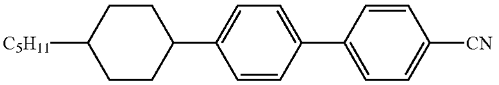

15%

Measuring Methods

The physical properties of the compound were measured according to the methods described below. Most of the methods are applied as described in EIAJ ED-2521A of the Standard of Electronic Industries Association of Japan, or as modified thereon. Moreover, no TFT was attached to a TN device used for measurement.

Among the values of physical properties, in the case where the compound itself was used as the sample, measured values were described as data. In the case where the mixture of the compound with the mother liquid crystals was used as the sample, values calculated from the measured values, according to the extrapolation method were described as data. For measuring a phase structure and a phase transition temperature, the compound was used as the sample as is. For measuring other physical properties, the mixture of the compound with mother liquid crystals (A) was used as the sample.

Phase Structure and Phase Transition Temperature (° C.): Measurement was carried out according to the methods (1) and (2) described below.

(1) A sample was placed on a hot plate of a melting point apparatus equipped with a polarizing microscope (FP-52 Hot Stage made by Mettler Toledo International Inc.), and a state of a phase and a change thereof were observed by means of the polarizing microscope while the sample was heated at a rate of 3° C. per minute, and a type of a liquid crystal phase was specified.

(2) Temperature was increased and decreased at a rate of 3° C. per minute using a differential scanning calorimeter DSC-7 System or Diamond DSC System made by PerkinElmer, Inc. A starting point (on set) of an endothermic peak or exothermic peak caused by a change in phase of a sample was determined according to extrapolation, and thus a phase transition temperature was finally determined.

Hereinafter, the crystals were expressed as C, and when the crystals were further distinguishable, each of the crystals was expressed as $C_1$ or $C_2$. The smectic phase or nematic phase was expressed as S or N. A liquid (isotropic) was expressed as I. When smectic A phase, smectic B phase, smectic C phase or smectic F phase was distinguishable among the smectic phases, the phases were expressed as $S_A$, $S_B$, $S_C$ or $S_F$, respectively. As an expression of the phase transition temperature, for example, "C 50.0 N 100.0 I" means that a phase transition temperature from the crystals to the nematic phase (CN) is 50.0° C., and a phase transition temperature from the nematic phase to the liquid (NI) is 100.0° C. A same rule applied to other expressions.

Maximum Temperature of a Nematic Phase ($T_{NI}$ or NI; ° C.): A sample was placed on a hot plate of a melting point apparatus equipped with a polarizing microscope (FP-52 Hot Stage made by Mettler Toledo International Inc.), and was observed by means of the polarizing microscope while the sample was heated at a rate of 1° C. per minute. Temperature when a part of the sample began to change from the nematic phase to the isotropic liquid was described as a maximum temperature. Hereinafter, a higher limit of a temperature range of the nematic phase may simply be abbreviated as "maximum temperature."

Compatibility at a Low Temperature: Samples in which the compound and the mother liquid crystals were mixed for the compound to be 20%, 15%, 10%, 5%, 3% and 1% were prepared, and put in glass vials. After the glass vials were kept in freezers at −10° C. or −20° C. for a predetermined period of time, whether or not the crystals or smectic phase precipitated was observed.

Viscosity (bulk viscosity; measured at 20° C.; mPa·s): Measurement was carried out using a cone-plate (E type) viscometer.

Refractive Index Anisotropy (Δn; measured at 25° C.): Measurement was carried out by means of an Abbe refractometer with a polarizing plate mounted on an ocular, using light at a wavelength of 589 nanometers. A surface of a main prism was rubbed in one direction, and then a sample was added dropwise onto the main prism. A refractive index (n||) was measured when the direction of polarized light was parallel to the direction of rubbing. A refractive index (n⊥) was measured when the direction of polarized light was perpendicular to the direction of rubbing. A value of refractive index anisotropy (Δn) was calculated from an equation: Δn=n||−n⊥.

Dielectric Anisotropy (Δ∈; measured at 25° C.): A sample was put in a TN device in which a distance (gap) between two glass substrates was about 9 micrometers and a twist angle was 80 degrees. A voltage of 20 V was applied to the cell, and a dielectric constant (∈||) in the major axis direction of liquid crystal molecules was measured. A voltage of 0.5 V was applied to the cell, and a dielectric constant (∈⊥) in the minor axis direction of the liquid crystal molecules was measured. A value of dielectric anisotropy was calculated from an equation: Δ∈=∈||−∈⊥.

Example 1

Synthesis of (E)-4-[1,2-difluoro-2-(3,4,5-trifluorophenyl)vinyl]-3-fluoro-4'-propyl biphenyl (1-1-1)

(1-1-1)

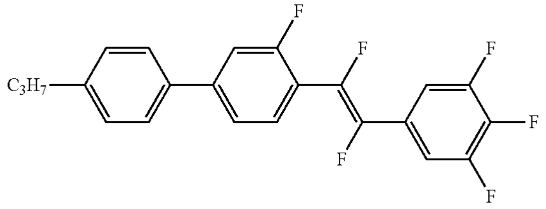

C 66.2 $S_A$ 95.2 N 116 I

-continued

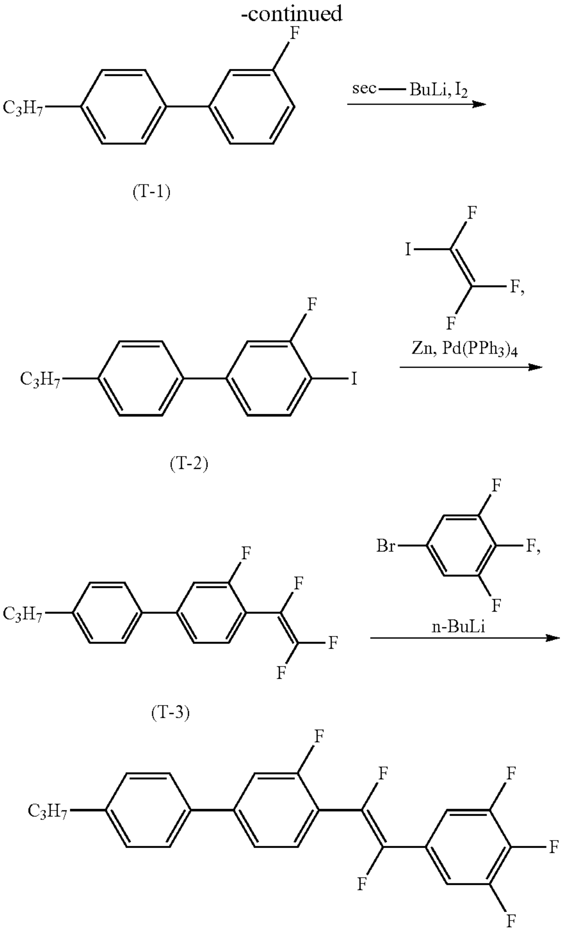

(T-1)

(T-2)

(T-3)

(No. 1-1-1)

Synthesis of Compound (T-2)

To a reaction vessel under a nitrogen atmosphere, 3-fluoro-4'-propylbiphenyl (T-1) (23.1 g) and THF (250 ml) were added, and cooling was carried out to −74° C. Thereto, a sec-butyllithium (1.06 M), cyclohexane, n-hexane solution (122 ml) was added dropwise in a temperature range of −74° C. to −70° C., and stirring was carried out for another 2 hours. Subsequently, a THF (200 ml) solution of iodine (35.6 g) was added dropwise in a temperature range of −75° C. to −70° C., and stirring was carried out for 6 hours while returning to room temperature. The resultant reaction mixture was poured into ice water (500 ml), and mixing was carried out. Toluene (400 ml) was added to separate layers into an organic layer and an aqueous layer, and an extraction operation was performed. The resultant organic layer was sequentially washed with an aqueous solution of sodium thiosulfate and water, and drying over anhydrous magnesium sulfate was carried out. The resultant solution was concentrated under reduced pressure, and a residue was purified by means of column chromatography (silica gel; heptane), and further purified by recrystallization from Solmix A-11, and thus 3-fluoro-4-iodo-4'-propylbiphenyl (T-2) (25.4 g) was obtained. The yield based on compound (T-1) was 69%.

Synthesis of Compound (T-3)

To a reaction vessel under a nitrogen atmosphere, zinc powder (3.85 g) and DMF (20 ml) were added, and cooling was carried out to 0° C. Thereto, a DMF (10 ml) solution of iodotrifluoroethylene (9.17 g) was added dropwise in a temperature range of 0° C. to 10° C., and stirring was carried out for 4 hours while returning to room temperature. Then, compound (T-2) (10.0 g) and tetrakistriphenylphosphine palladium (0.679 g) were added and stirring was carried out at 100° C. for 2 hours. The reaction mixture was cooled to room temperature, and then poured into ice water (50 ml), and mixing was carried out. Toluene (100 ml) was added to separate layers into an organic layer and an aqueous layer, and an extraction operation was performed. The resultant organic layer was washed with water, and drying over anhydrous magnesium sulfate was carried out. The resultant solution was concentrated under reduced pressure, and a residue was purified by means of column chromatography (silica gel; heptane), and thus 3-fluoro-4'-propyl-4-(1,2,2-trifluorovinyl) biphenyl (T-3) (7.47 g) was obtained. The yield based on compound (T-2) was 86%.

Synthesis of Compound (1-1-1)

To a reaction vessel under a nitrogen atmosphere, 1-bromo-3,4,5-trifluorobenzene (10.7 g) and diethyl ether (150 ml) were added, and cooling was carried out to −50° C. Thereto, a n-butyllithium (1.57 M) n-hexane solution (30.7 ml) was added dropwise in a temperature range of −50° C. to −45° C., and stirring was carried out for another 1 hour. Then, after cooling to −74° C., a diethyl ether (20.0 ml) solution of compound (T-3) (7.47 g) was added dropwise in a temperature range of −74° C. to −70° C., and stirring was carried out for 4 hours while returning to room temperature. The resultant reaction mixture was poured into ice water (200 ml), and mixing was carried out. Toluene (200 ml) was added to separate layers into an organic layer and an aqueous layer, and an extraction operation was performed. The resultant organic layer was sequentially washed with a 1 N hydrochloric acid solution, a saturated aqueous solution of sodium hydrogencarbonate and water, and drying over anhydrous magnesium sulfate was carried out. The resultant solution was concentrated under reduced pressure, and a residue was purified by fractionation by means of column chromatography (silica gel; heptane), and further purified by recrystallization from a heptane/Solmix A-11 mixed solvent, and thus (E)-4-[1,2-difluoro-2-(3,4,5-trifluorophenyl)vinyl]-3-fluoro-4'-propylbiphenyl (1-1-1) (3.75 g) was obtained. The yield based on compound (T-3) was 36%.

Chemical shifts according to $^1$H-NMR analysis were as described below, and the compound obtained could be identified to be (E)-4-[1,2-difluoro-2-(3,4,5-trifluorophenyl)vinyl]-3-fluoro-4'-propylbiphenyl.

Chemical shifts δ (ppm; $CDCl_3$); 7.58 (dd, J=7.80 Hz, J=7.65 Hz, 1H), 7.53 (d, J=8.15 Hz, 2H), 7.50-7.37 (m, 4H), 7.29 (d, J=8.10 Hz, 2H), 2.65 (t, J=7.85 Hz, 2H), 1.75-1.64 (m, 2H), 0.98 (t, 7.45 Hz, 3H).

A phase transition temperature of compound (1-1-1) obtained was as described below.

Phase transition temperature: C 66.2 $S_A$ 95.2 N 116 I.

Example 2

Physical Properties of Compound (1-1-1)

The physical properties of mother liquid crystals (A) described previously were as described below.

Maximum temperature ($T_{NI}$)=71.7° C.; refractive index anisotropy (Δn)=0.137; dielectric anisotropy (Δ∈)=11.0.

Composition B including 85% of mother liquid crystals (A) and 15% of (E)-4-[1,2-difluoro-2-(3,4,5-trifluorophenyl)vinyl]-3-fluoro-4'-propylbiphenyl (1-1-1) obtained in Example 1 was prepared. Physical properties of composition B obtained were measured and values of physical properties of compound (1-1-1) were calculated by extrapolating the measured values. The results were as described below.

Maximum temperature ($T_{NI}$)=90.4° C.; refractive index anisotropy (Δn)=0.250; dielectric anisotropy (Δ∈)=21.0; viscosity (η)=49.5 mPa·s.

The findings show that compound (1-1-1) has a good compatibility with other compounds, a large refractive index anisotropy, a large dielectric anisotropy and a small viscosity

Example 3

Synthesis of (E)-4-[1,2-difluoro-2-(3,4,5-trifluorophenyl)vinyl]-3,5-difluoro-4'-propyl biphenyl (1-1-11)

(1-1-11)

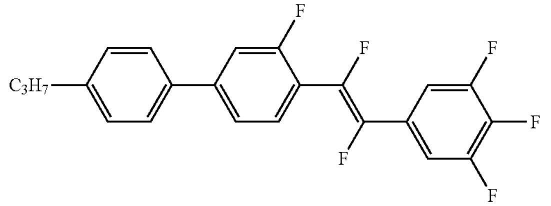

C 69.71

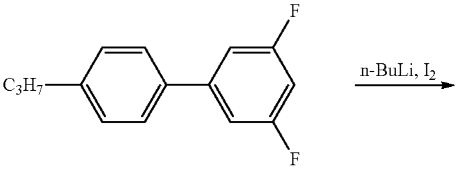

(T-4)

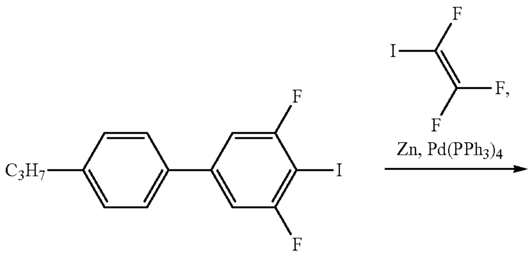

(T-5)

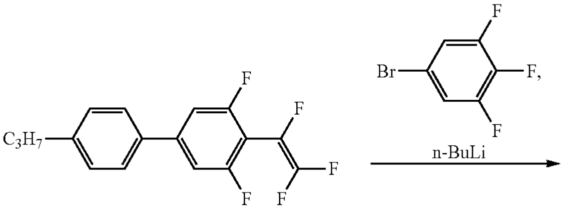

(T-6)

-continued

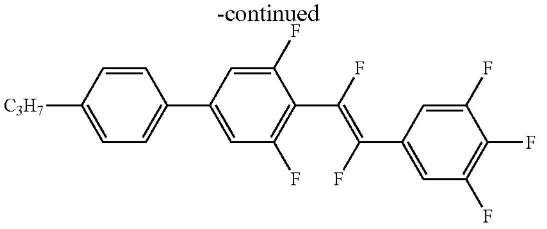

(No. 1-1-11)

Synthesis of Compound (T-5)

To a reaction vessel under a nitrogen atmosphere, 3,5-difluoro-4'-propylbiphenyl (T-4) (18.0 g) and THF (200 ml) were added, and cooling was carried out to −74° C. Thereto, a n-butyllithium (1.57 M) n-hexane solution (56.4 ml) was added dropwise in a temperature range of −74° C. to −70° C., and stirring was carried out for another 1 hour. Subsequently, a THF (150 ml) solution of iodine (24.6 g) was added dropwise in a temperature range of −75° C. to −70° C., and stirring was carried out for 6 hours while returning to room temperature. The resultant reaction mixture was poured into ice water (400 ml), and mixing was carried out. Toluene (300 ml) was added to separate layers into an organic layer and an aqueous layer, and an extraction operation was performed. The resultant organic layer was sequentially washed with an aqueous solution of sodium thiosulfate and water, and drying over anhydrous magnesium sulfate was carried out. The resultant solution was concentrated under reduced pressure, and a residue was purified by means of column chromatography (silica gel; heptane), and further purified by recrystallization from Solmix A-11, and thus 3,5-difluoro-4-iodo-4'-propylbiphenyl (T-5) (21.4 g) was obtained. The yield based on compound (T-4) was 77%.

Synthesis of Compound (T-6)

As a raw material, compound (T-5) (10.0 g) was used. Then, 3,5-difluoro-4'-propyl-4-(1,2,2-trifluorovinyl)biphenyl (T-6) (6.69 g) was obtained in a manner similar to synthesis of compound (T-3) in Example 1. The yield based on compound (T-5) was 77%.

Synthesis of Compound (1-1-11)

As a raw material, compound (T-6) was used. Then, (E)-4-[1,2-difluoro-2-(3,4,5-trifluorophenyl)vinyl]-3,5-difluoro-4'-propylbiphenyl (1-1-11) (3.71 g) was obtained in a manner similar to synthesis of compound (No. 1-1-1) in Example 1. The yield based on compound (T-6) was 41%.

Chemical shifts according to $^1$H-NMR analysis were as described below, and the compound obtained could be identified to be (E)-4-[1,2-difluoro-2-(3,4,5-trifluorophenyl)vinyl]-3,5-difluoro-4'-propylbiphenyl.

Chemical shifts δ (ppm; $CDCl_3$): 7.51 (d, J=8.10 Hz, 2H), 7.45 (dd, J=8.45 Hz, J=6.70 Hz, 2H), 7.30 (d, J=8.10 Hz, 2H), 7.23 (d, J=9.10 Hz, 2H), 2.65 (t, J=7.80 Hz, 2H), 1.74-1.64 (m, 2H), 0.98 (t, 7.45 Hz, 3H).

A phase transition temperature of compound (1-1-11) obtained was as described below.

Phase transition temperature: C 69.7 I.

Example 4

Physical Properties of Compound (1-1-11)

Composition C including 85% of mother liquid crystals (A) and 15% of (E)-4-[1,2-difluoro-2-(3,4,5-trifluorophenyl)vinyl]-3,5-difluoro-4'-propylbiphenyl (No. 1-1-11) obtained in Example 3 was prepared. Physical properties of composition C obtained were measured and values of physical properties of compound (1-1-11) were calculated by extrapolating the measured values. The results were as described below.

Maximum temperature ($T_{NI}$)=49.7° C.; refractive index anisotropy (Δn)=0.210; dielectric anisotropy ($\Delta\epsilon$)=28.3; viscosity (η)=63.2 mPa·s.

The findings show that compound (1-1-11) has a good compatibility with other compounds, a large refractive index anisotropy and a large dielectric anisotropy.

Example 5

Synthesis of (E)-1-[1,2-difluoro-2-(3,4,5-trifluorophenyl)vinyl]-2-fluoro-4-(4-propyl cyclohexyl) benzene (1-1-21)

(1-1-21)

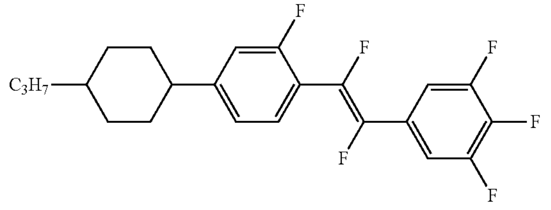

C 63.5 N 111 I

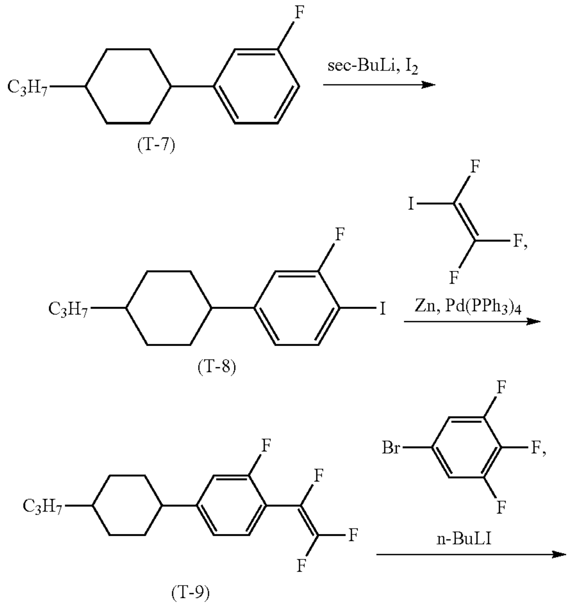

(T-7)

(T-8)

(T-9)

-continued

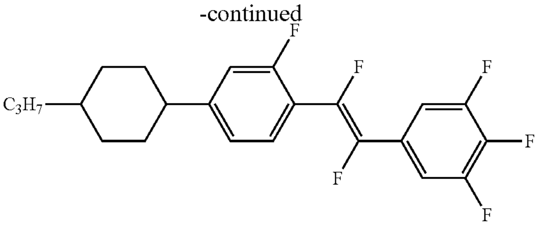

(No.1-1-21)

Synthesis of Compound (T-8)

As a raw material, 1-fluoro-3-(4-propylcyclohexyl)benzene (T-7) (30.0 g) was used. Then, 1-fluoro-2-iodo-5-(4-propylcyclohexyl)benzene (T-8) (36.3 g) was obtained in a manner similar to synthesis of compound (T-2) in Example 1. The yield based on compound (T-7) was 77%.

Synthesis of Compound (T-9)

As a raw material, compound (T-8) (6.00 g) was used. Then, 2-fluoro-4-(4-propylcyclohexyl)-1-(1,2,2-trifluorovinyl)benzene (T-9) (5.05 g) was obtained in a manner similar to synthesis of compound (T-3) in Example 1. The yield based on compound (T-8) was 97%.

Synthesis of Compound (1-1-21)

As a raw material, compound (T-9) (2.50 g) was used. Then, (E)-1-[1,2-difluoro-2-(3,4,5-trifluorophenyl)vinyl]-2-fluoro-4-(4-propylcyclohexyl)benzene (No. 1-1-21) (1.51 g) was obtained in a manner similar to synthesis of compound (1-1-1) in Example 1. The yield based on compound (T-9) was 44%.

Chemical shifts according to $^1$H-NMR analysis were as described below, and the compound obtained could be identified to be (E)-1-[1,2-difluoro-2-(3,4,5-trifluorophenyl)vinyl]-2-fluoro-4-(4-propylcyclohexyl)benzene.

Chemical shifts δ (ppm; $CDCl_3$); 7.47-7.37 (m, 3H), 7.09 (d, J=8.10 Hz, 1H), 7.02 (d, J=11.7 Hz, 1H), 2.51 (tt, J=9.10 Hz, J=3.15 Hz, 1H), 1.95-1.85 (m, 4H), 1.50-1.39 (m, 2H), 1.39-1.26 (m, 3H), 1.26-1.19 (m, 2H), 1.11-1.00 (m, 2H), 0.91 (t, J=7.40 Hz, 3H).

A phase transition temperature of compound (1-1-21) obtained was as described below.

Phase transition temperature: C 63.5 N 111 I.

Example 6

Physical Properties of Compound (1-1-21)

Composition D including 85% of mother liquid crystals (A) and 15% of (E)-1-[1,2-difluoro-2-(3,4,5-trifluorophenyl)vinyl]-2-fluoro-4-(4-propylcyclohexyl)benzene (1-1-21) obtained in Example 5 was prepared. Physical properties of composition D obtained were measured and values of physical properties of compound (1-1-21) were calculated by extrapolating the measured values. The results were as described below.

Maximum temperature ($T_{NI}$)=89.7° C.; refractive index anisotropy (Δn)=0.177; dielectric anisotropy (Δ∈)=19.4; viscosity (η)=41.4 mPa·s.

The findings show that compound (1-1-21) has a good compatibility with other compounds, a large dielectric anisotropy and a small viscosity.

Example 7

Synthesis of (E)-1-(1,2-difluoro-2-[3-fluoro-4-(trifluoromethyl)phenyl]vinyl)-2-fluoro-4-(4-propylcyclohexyl)benzene (1-1-25)

(1-1-25)

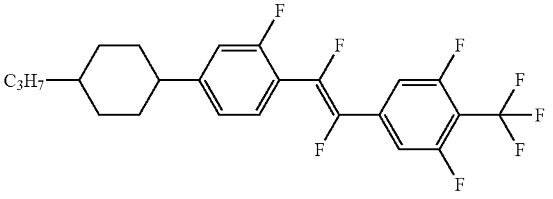

C 104 N 125 I

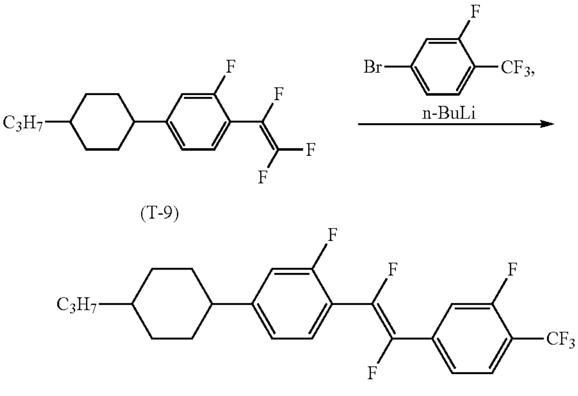

(T-9)

(No. 1-1-25)

Synthesis of Compound (1-1-25)

To a reaction vessel under a nitrogen atmosphere, 4-bromo-2-fluoro-1-(trifluoromethyl)benzene (2.28 g) and diethyl ether (70 ml) were added, and cooling was carried out to −70° C. Thereto, a n-butyllithium (1.57 M) n-hexane solution (7.10 ml) was added dropwise in a temperature range of −70° C. to −65° C., and stirring was carried out for another 1 hour. Subsequently, a diethyl ether (10 ml) solution of compound (T-9) (2.68 g) was added dropwise in a temperature range of −70° C. to −65° C., and stirring was carried out for 4 hours while returning to room temperature. The resultant reaction mixture was poured into ice water (100 ml), and mixing was carried out. Toluene (100 ml) was added to separate layers into an organic layer and an aqueous layer, and an extraction operation was performed. The resultant organic layer was sequentially washed with a 1 N hydrochloric acid solution, a saturated aqueous solution of sodium hydrogencarbonate and water, and drying over anhydrous magnesium sulfate was carried out. The resultant solution was concentrated under reduced pressure, and a residue was purified by fractionation by means of column chromatography (silica gel; heptane), and further purified by recrystallization from a heptane/Solmix A-11 mixed solvent, and thus (E)-1-(1,2-difluoro-2-[3-fluoro-4-(trifluoromethyl)phenyl]vinyl)-2-fluoro-4-(4-propylcyclohexyl)benzene (1-1-25) (2.24 g) was obtained. The yield based on compound (T-9) was 57%.

Chemical shifts according to $^1$H-NMR analysis were as described below, and the compound obtained could be identified to be (E)-1-(1,2-difluoro-2-[3-fluoro-4-(trifluoromethyl)phenyl]vinyl)-2-fluoro-4-(4-propylcyclohexyl)benzene.

Chemical shifts δ (ppm; $CDCl_3$); 7.72-7.57 (m, 3H), 7.46 (dd, J=7.65 Hz, J=7.65 Hz, 1H), 7.10 (d, J=8.05 Hz, 1H), 7.04 (d, J=11.7 Hz, 1H), 2.52 (tt, J=9.15 Hz, J=3.15 Hz, 1H), 1.96-1.85 (m, 4H), 1.50-1.38 (m, 2H), 1.38-1.26 (m, 3H), 1.26-1.19 (m, 2H), 1.12-1.01 (m, 2H), 0.91 (t, J=7.30 Hz, 3H).

A phase transition temperature of compound (1-1-25) obtained was as described below.

Phase transition temperature: C 104 N 125 I.

Example 8

Physical Properties of Compound (1-1-25)

Composition E including 85% of mother liquid crystals (A) and 15% of (E)-1-(1,2-difluoro-2-[3-fluoro-4-(trifluoromethyl)phenyl]vinyl)-2-fluoro-4-(4-propylcyclohexyl)benzene (1-1-25) obtained in Example 7 was prepared. Physical properties of composition E obtained were measured and values of physical properties of compound (1-1-25) were calculated by extrapolating the measured values. The results were as described below.

Maximum temperature ($T_{NI}$)=95° C.; refractive index anisotropy (Δn)=0.190; dielectric anisotropy (Δε)=22.1; viscosity (η)=52.9 mPa·s.

The findings show that compound (1-1-25) has a good compatibility with other compounds, a large dielectric anisotropy and a small viscosity.

Example 9

Synthesis of (E)-4-[1,2-difluoro-2-(3,4,5-trifluorophenyl)vinyl]-3-fluoro-4'-(4-propyl cyclohexyl) biphenyl (1-2-16)

(1-2-16)

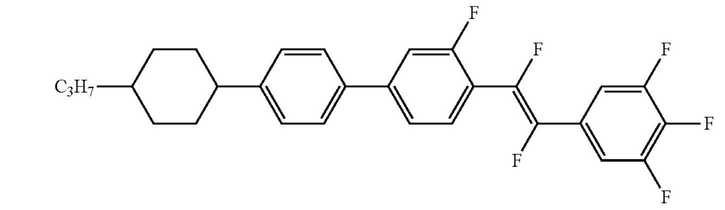

C 88.8 $S_A$ 138 N 286 I

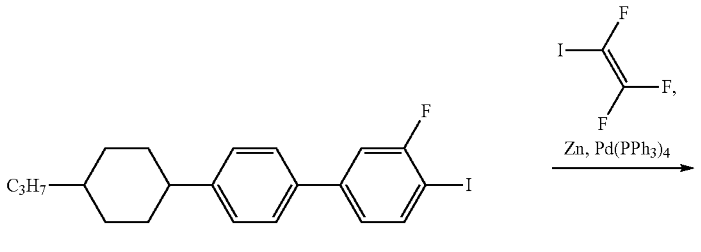

(T-10)

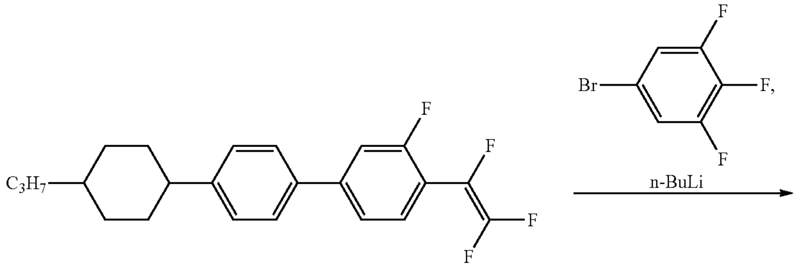

(T-11)

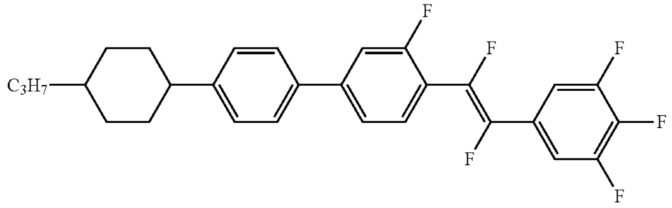

(No. 1-2-16)

Synthesis of Compound (T-11)

As a raw material, 3-fluoro-4-iodo-4'-(4-propylcyclohexyl)biphenyl (T-10) (5.00 g) was used. Then, 3-fluoro-4'-(4-propylcyclohexyl)-4-(1,2,2-trifluorovinyl)biphenyl (T-11) (3.79 g) was obtained in a manner similar to synthesis of compound (T-3) in Example 1. The yield based on compound (T-10) was 85%.

Synthesis of Compound (1-2-16)

As a raw material, compound (T-11) (3.79 g) was used. Then, (E)-4-[1,2-difluoro-2-(3,4,5-trifluorophenyl)vinyl]-3-fluoro-4'-(4-propylcyclohexyl)biphenyl (No. 1-2-16) (1.18 g) was obtained in a manner similar to synthesis of compound (1-1-1) in Example 1. The yield based on compound (T-11) was 24%.

Chemical shifts according to $^{1}H$-NMR analysis were as described below, and the compound obtained could be identified to be (E)-4-[1,2-difluoro-2-(3,4,5-trifluorophenyl)vinyl]-3-fluoro-4'-(4-propylcyclohexyl)biphenyl.

Chemical shifts δ (ppm; $CDCl_3$); 7.61-7.52 (m, 3H), 7.49-7.37 (m, 4H), 7.32 (d, J=9.00 Hz, 2H), 2.53 (tt, J=12.2 Hz, J=3.15 Hz, 1H), 1.97-1.85 (m, 4H), 1.55-1.43 (m, 2H), 1.41-1.27 (m, 3H), 1.27-1.19 (m, 2H), 1.14-1.02 (m, 2H), 0.91 (t, J=7.40 Hz, 3H).

A phase transition temperature of compound (1-2-16) obtained was as described below.

Phase transition temperature: C 88.8 $S_A$ 138 N 286 I.

Example 10

Physical Properties of Compound (1-2-16)

Composition F including 85% of mother liquid crystals (A) and 15% of (E)-4-[1,2-difluoro-2-(3,4,5-trifluorophenyl)vinyl]-3-fluoro-4'-(4-propylcyclohexyl)biphenyl (1-2-16) obtained in Example 9 was prepared. Physical properties of composition F obtained were measured and values of physical properties of compound (1-2-16) were calculated by extrapolating the measured values. The results were as described below.

Maximum temperature ($T_{NI}$)=200° C.; refractive index anisotropy (Δn)=0.270; dielectric anisotropy (Δ∈)=17.2; viscosity (η)=80.9 mPa·s.

The findings show that compound (1-2-16) has a good compatibility with other compounds, a very high clearing point, a large dielectric anisotropy and a large refractive index anisotropy.

Example 11

Synthesis of (E)-4-[1,2-difluoro-2-(3-fluoro-4'-propylbiphenyl-4-yl)vinyl]-2,3',4',5'-tetrafluorobiphenyl (1-3-1)

(1-3-1)

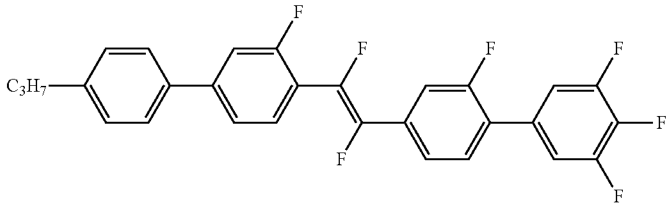

C 151 $S_A$ 182 N 276 I

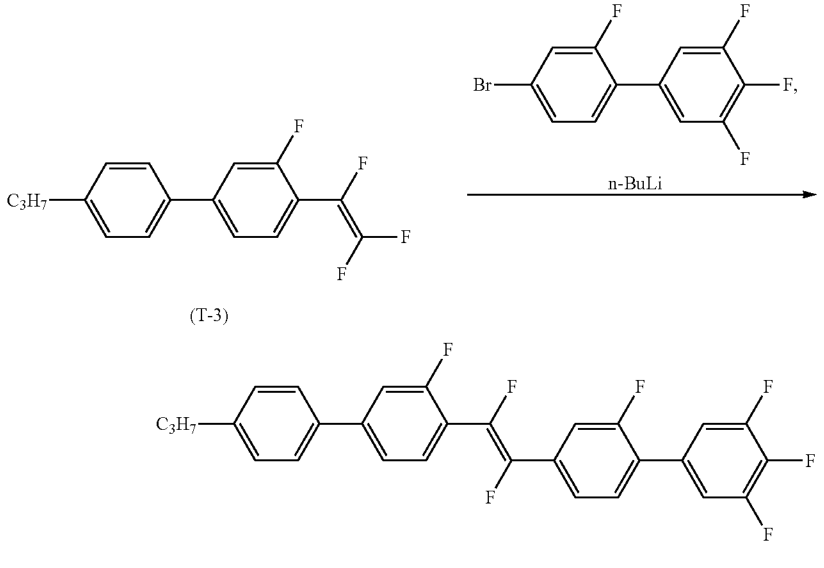

(T-3)

(No. 1-3-1)

Synthesis of Compound (1-3-1)

To a reaction vessel under a nitrogen atmosphere, 4-bromo-2,3',4',5'-tetrafluorobiphenyl (4.84 g) and diethyl ether (130 ml) were added, and cooling was carried out to −50° C. Thereto, a n-butyllithium (1.57 M) n-hexane solution (8.90 ml) was added dropwise in a temperature range of −50° C. to −45° C., and stirring was carried out for another 2 hours. Subsequently, a diethyl ether (20 ml) solution of compound (T-3) (3.11 g) was added dropwise in a temperature range of −70° C. to −65° C., and stirring was carried out for 1 hour while returning to room temperature. The resultant reaction mixture was poured into ice water (150 ml), and mixing was carried out. Toluene (150 ml) was added to separate layers into an organic layer and an aqueous layer, and an extraction operation was performed. The resultant organic layer was sequentially washed with a 1 N hydrochloric acid solution, a saturated aqueous solution of sodium hydrogencarbonate and water, and drying over anhydrous magnesium sulfate was carried out. The resultant solution was concentrated under reduced pressure, and a residue was purified by fractionation by means of column chromatography (silica gel; heptane), and further purified by recrystallization from a toluene/Solmix A-11 mixed solvent, and thus (E)-4-[1,2-difluoro-2-(3-fluoro-4'-propylbiphenyl-4-yl)vinyl]-2,3',4',5'-tetrafluorobiphenyl (1-3-1) (2.76 g) was obtained. The yield based on compound (T-3) was 52%.

Chemical shifts according to $^{1}$H-NMR analysis were as described below, and the compound obtained could be identified to be (E)-4-[1,2-difluoro-2-(3-fluoro-4'-propylbiphenyl-4-yl)vinyl]-2,3',4',5'-tetrafluorobiphenyl.

Chemical shifts δ (ppm; $CDCl_3$); 7.68-7.57 (m, 3H), 7.54 (dd, J=8.10 Hz, 2H), 7.51-7.45 (m, 2H), 7.41 (d, J=11.9 Hz, 1H), 7.30 (d, J=8.10 Hz, 2H), 7.27-7.22 (m, 2H), 2.65 (t, J=7.85 Hz, 2H), 1.75-1.65 (m, 2H), 0.98 (t, 7.40 Hz, 3H).

A phase transition temperature of compound (1-3-1) obtained was as described below.

Phase transition temperature: C 151 $S_A$ 182 N 276 I.

Example 12

Physical Properties of Compound (1-3-1)

Composition G including 97% of mother liquid crystals (A) and 3% of (E)-4-[1,2-difluoro-2-(3-fluoro-4'-propylbiphenyl-4-yl)vinyl]-2,3',4',5'-tetrafluorobiphenyl (1-3-1) obtained in Example 11 was prepared. Physical properties of composition G obtained were measured and values of physical properties of compound (1-3-1) were calculated by extrapolating the measured values. The results were as described below.

Maximum temperature ($T_{NI}$)=182° C.; refractive index anisotropy (Δn)=0.370; dielectric anisotropy (Δ∈)=28.5; viscosity (η)=93.9 mPa·s.

The findings show that compound (1-3-1) has a very large refractive index anisotropy, a high clearing point and a large dielectric anisotropy.

Example 13

On the basis of synthetic methods as described in Examples 1, 3, 5, 7, 9 and 11, and also described herein, compound (1-1-1) to compound (1-1-40), compound (1-2-1) to compound (1-2-40), compound (1-3-1) to compound (1-3-14) and compound (1-4-1) to compound (1-4-6) could be prepared. Data appended are described using values determined in accordance with the techniques described previously. Maximum temperature ($T_{NI}$), dielectric anisotropy (Δ∈), refractive index anisotropy (Δn) and viscosity (η) are described using values of physical properties calculated, according to the extrapolation method, from measured values of physical properties of a sample obtained by mixing the compound with mother liquid crystals (A) as described in Examples 2, 4, 6, 8, 10 and 12.

| No. | |
|---|---|
| 1-1-1 | 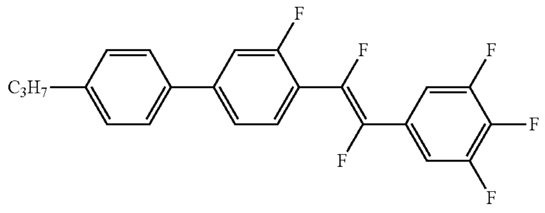 $T_{NI}$ = 90.4° C., Δ n = 0.250, Δ ε = 21.0 η = 49.5 mPa · s |
| 1-1-2 | 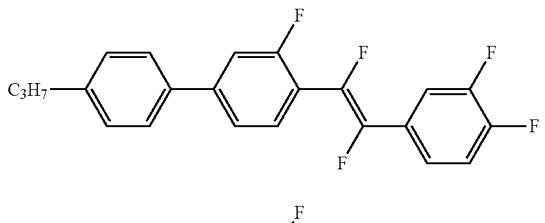 |
| 1-1-3 | 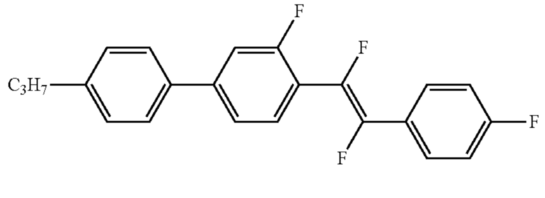 |

-continued
| No. | |
|---|---|
| 1-1-4 | 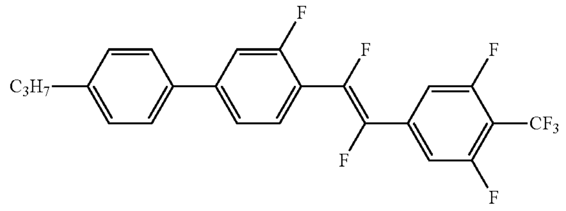 |
| 1-1-5 | 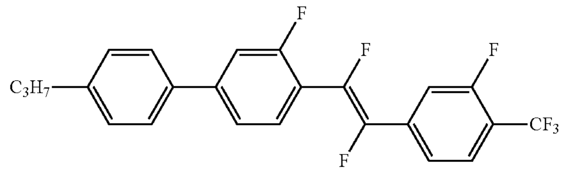 |
| 1-1-6 | 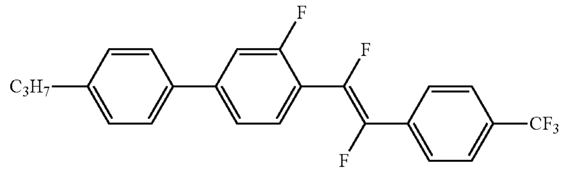 |
| 1-1-7 | 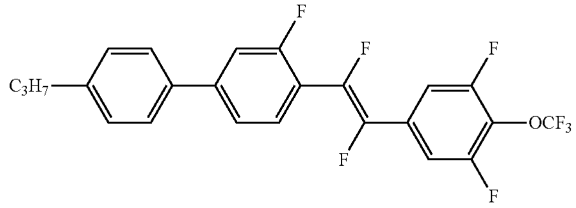 |
| 1-1-8 | 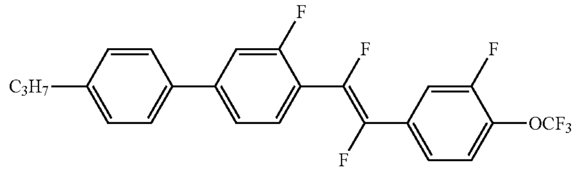 |
| 1-1-9 | 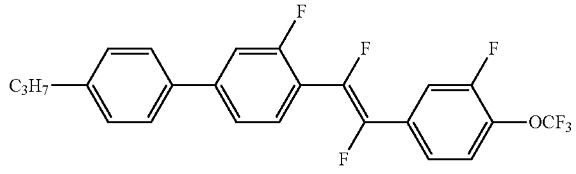 |
| 1-1-10 | 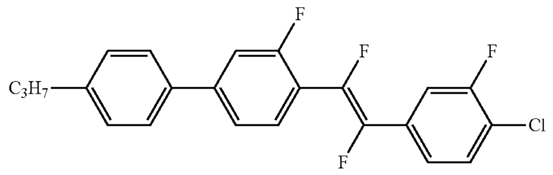 |

-continued
| No. | |
|---|---|
| 1-1-11 | 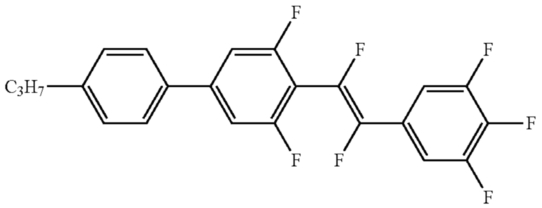<br>$T_{NI}$ = 49.7° C., Δ n = 0.210, Δ ε = 28.3<br>η = 63.2 mPa · s |
| 1-1-12 | 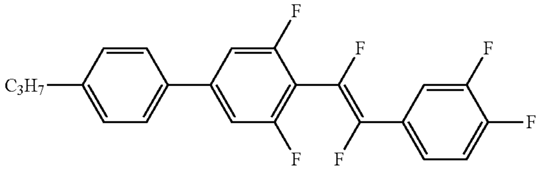 |
| 1-1-13 | 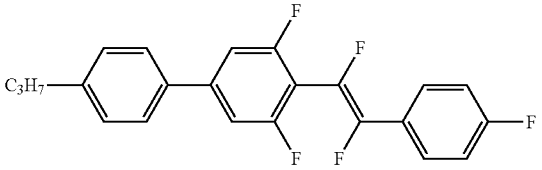 |
| 1-1-14 | 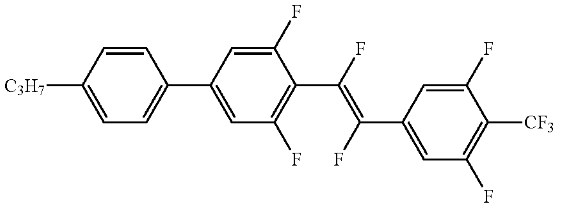 |
| 1-1-15 | 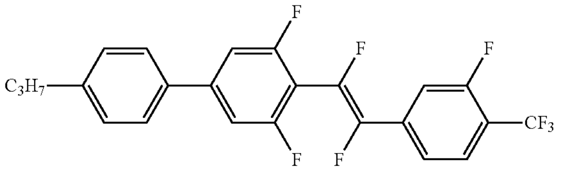 |
| 1-1-16 | 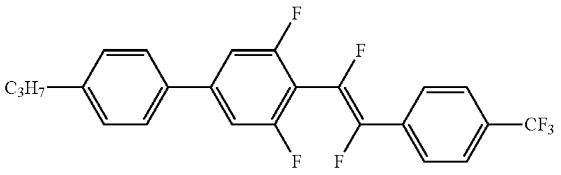 |
| 1-1-17 | 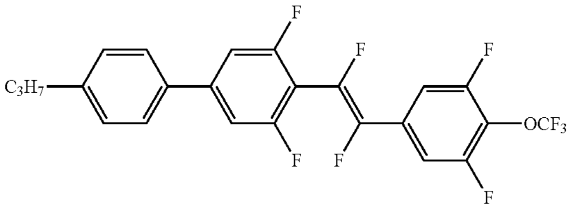 |

-continued
| No. | |
|---|---|
| 1-1-18 | 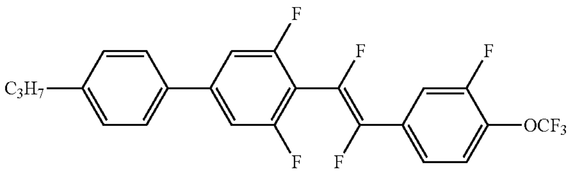 |
| 1-1-19 | 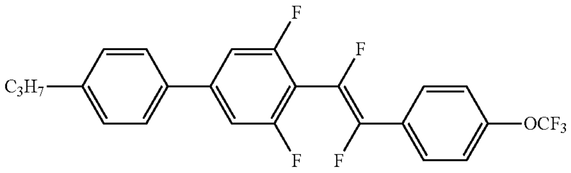 |
| 1-1-20 | 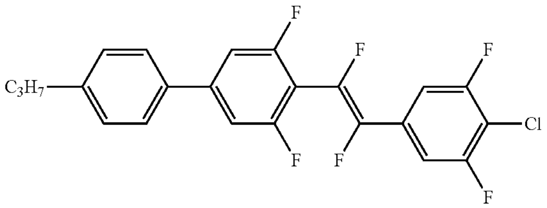 |
| 1-1-21 | 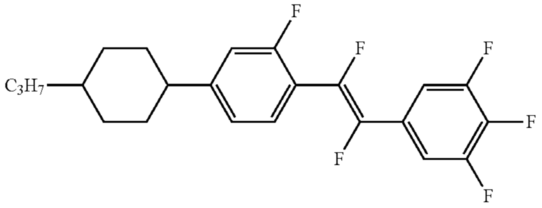<br>$T_{NI}$ =89.7° C., Δ n = 0.177, Δ ε = 19.4<br>η = 41.4 mPa · s |
| 1-1-22 | 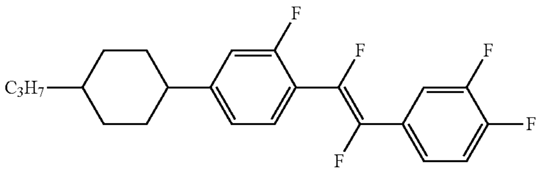 |
| 1-1-23 | 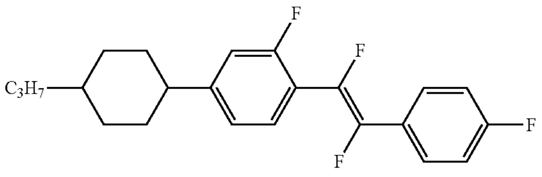 |
| 1-1-24 | 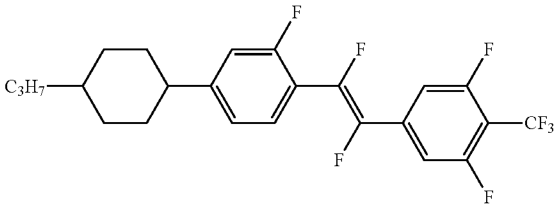 |

-continued
| No. | |
|---|---|
| 1-1-25 | 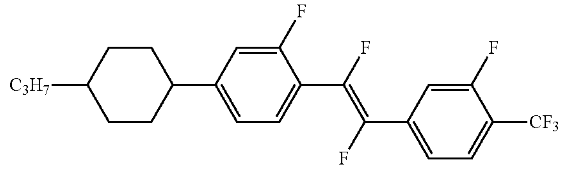<br>$T_{NI}$ =95.0° C., Δ n = 0.190, Δ ε = 22.1<br>η = 52.9 mPa · s |
| 1-1-26 | 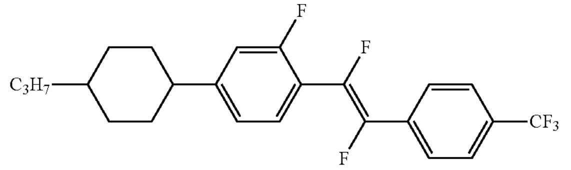 |
| 1-1-27 | 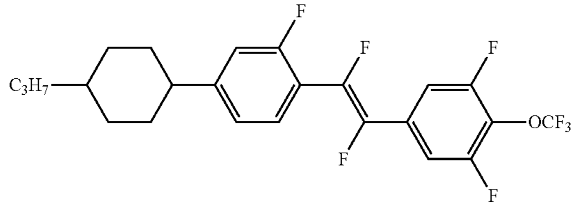 |
| 1-1-28 | 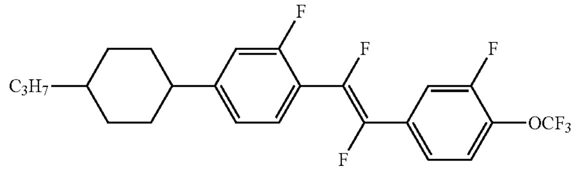 |
| 1-1-29 | 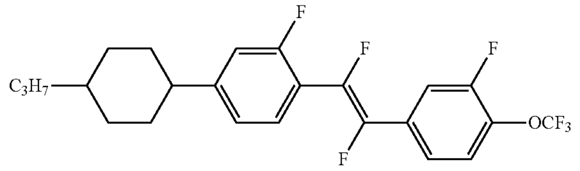 |
| 1-1-30 | 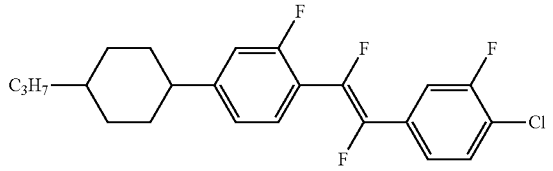 |
| 1-1-31 | 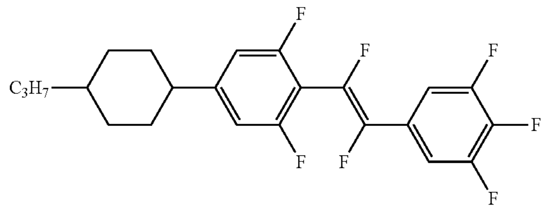 |
| 1-1-32 | 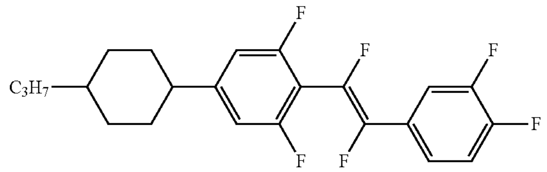 |

-continued
| No. | |
|---|---|
| 1-1-33 | 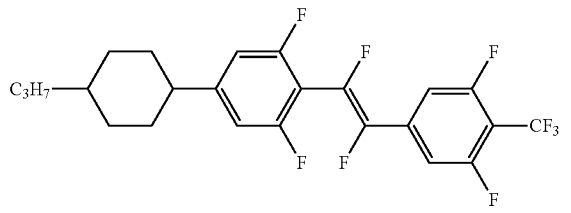 |
| 1-1-34 | 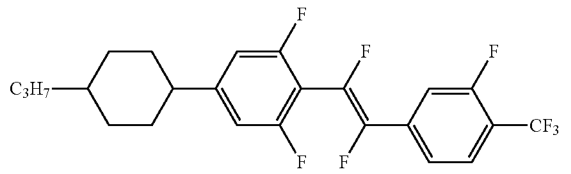 |
| 1-1-35 | 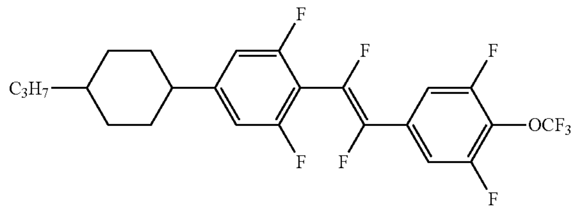 |
| 1-1-36 | 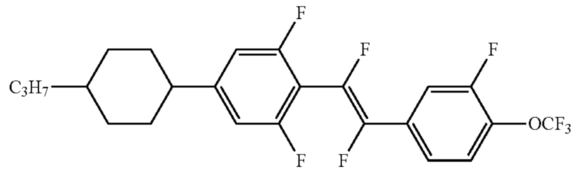 |
| 1-1-37 | 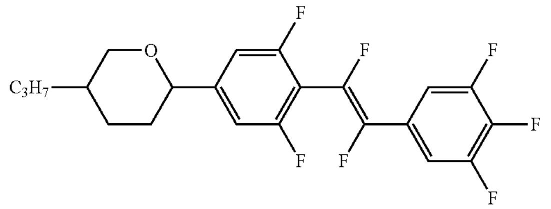 |
| 1-1-38 | 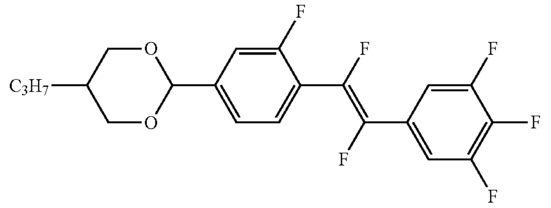 |
| 1-1-39 | 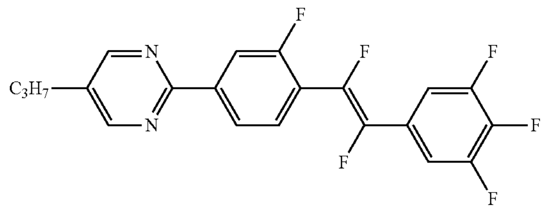 |

-continued
| No. | |
|---|---|
| 1-1-40 | 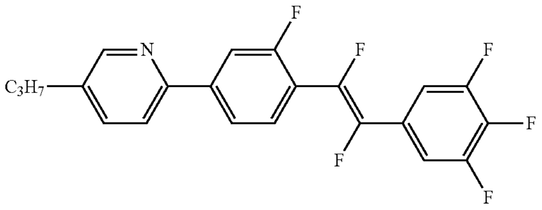 |
| 1-2-1 | 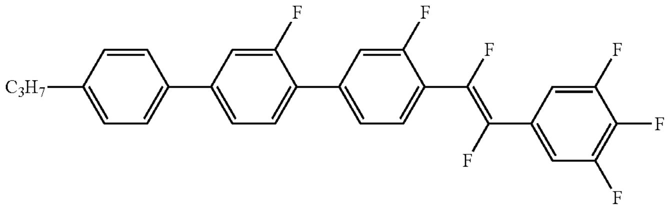 |
| 1-2-2 | 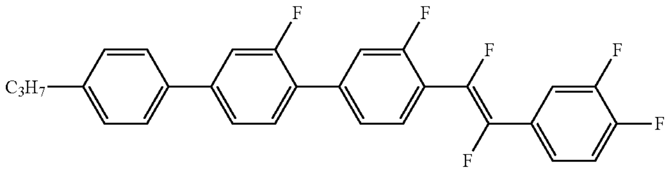 |
| 1-2-3 | 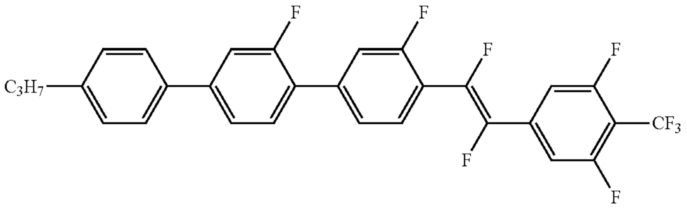 |
| 1-2-4 | 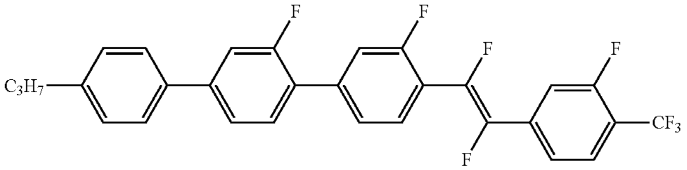 |
| 1-2-5 | 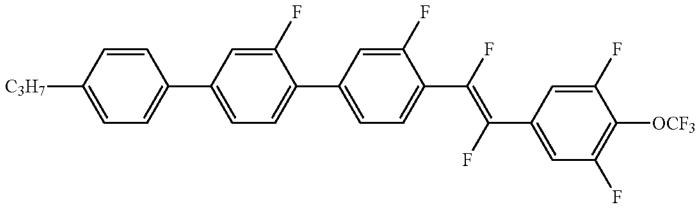 |
| 1-2-6 | 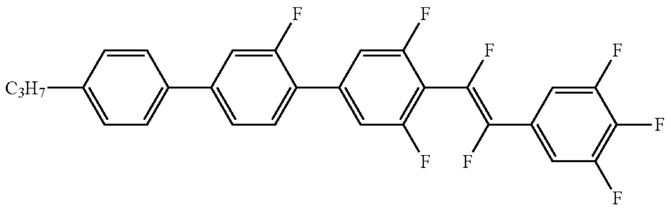 |

-continued
| No. | |
|---|---|
| 1-2-7 | 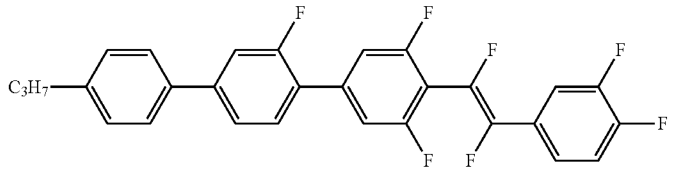 |
| 1-2-8 | 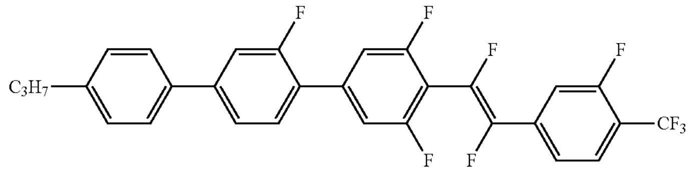 |
| 1-2-9 | 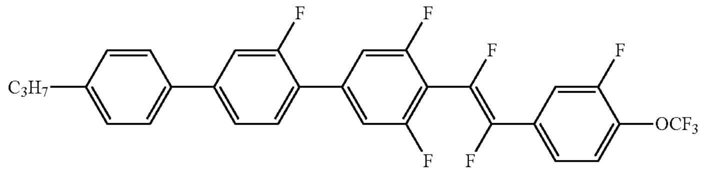 |
| 1-2-10 | 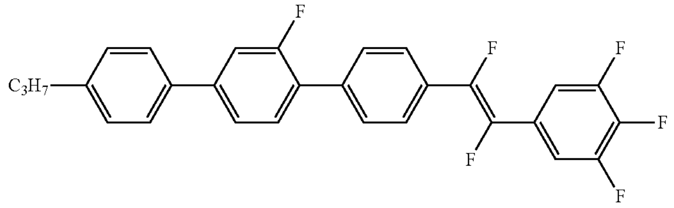 |
| 1-2-11 | 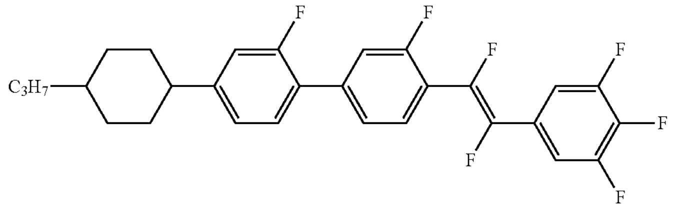 |
| 1-2-12 | 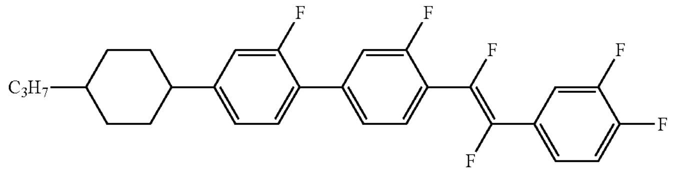 |
| 1-2-13 | 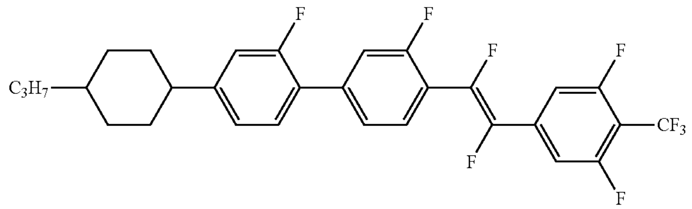 |
| 1-2-14 | 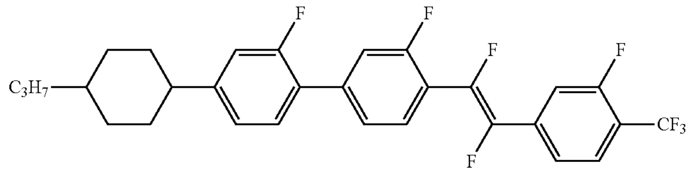 |

-continued
| No. | |
|---|---|
| 1-2-15 | 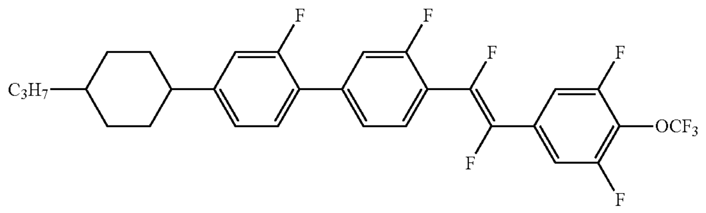 |
| 1-2-16 | 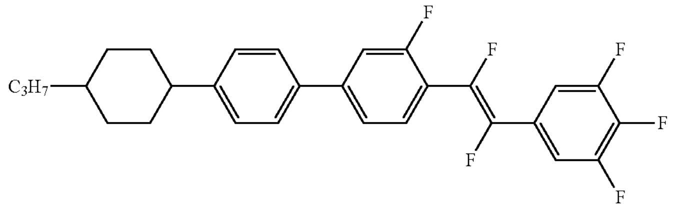 |
| | $T_{NI}$ = 200° C., Δ n = 0.270, Δ ε = 17.2<br>η = 80.9 mPa · s |
| 1-2-17 | 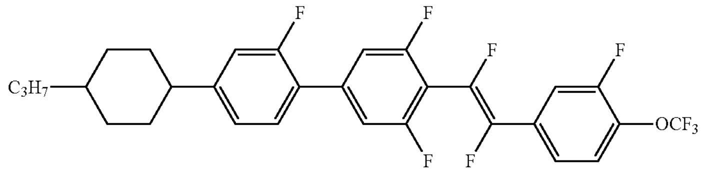 |
| 1-2-18 | 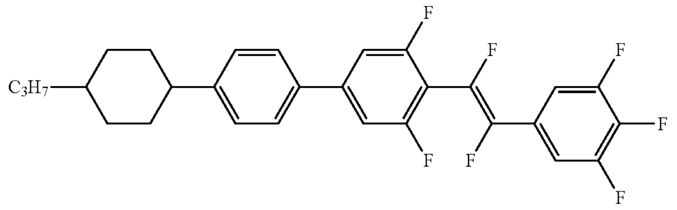 |
| 1-2-19 | 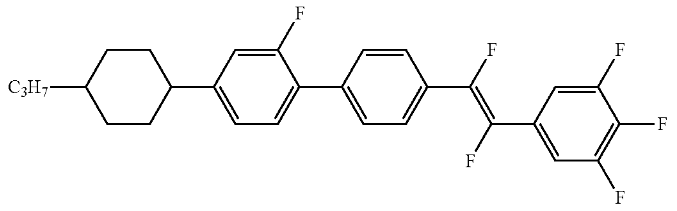 |
| 1-2-20 | 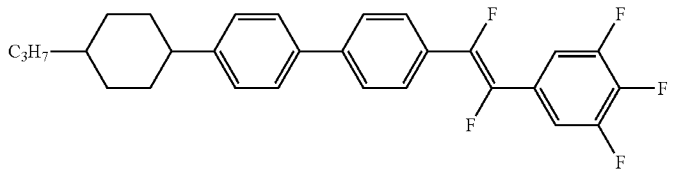 |
| 1-2-21 | 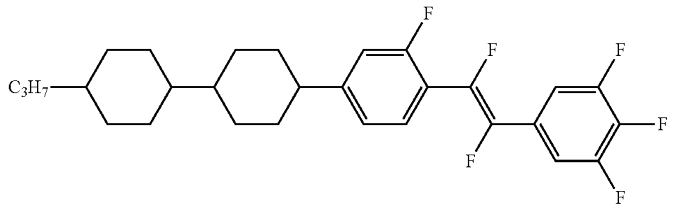 |

-continued
| No. | |
|---|---|
| 1-2-22 | 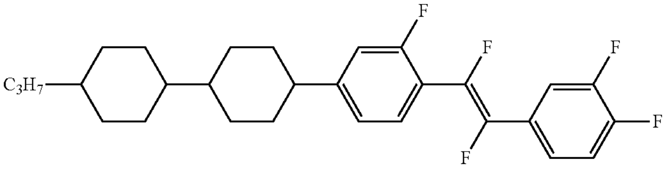 |
| 1-2-23 | 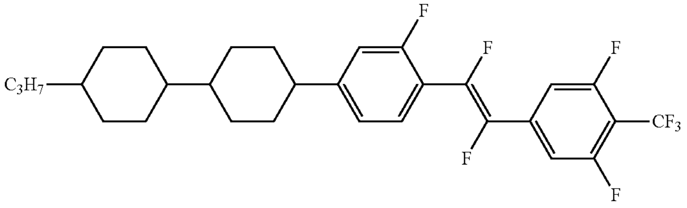 |
| 1-2-24 | 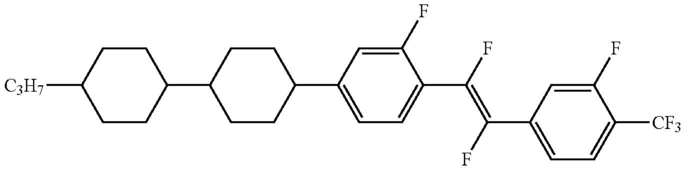 |
| 1-2-25 | 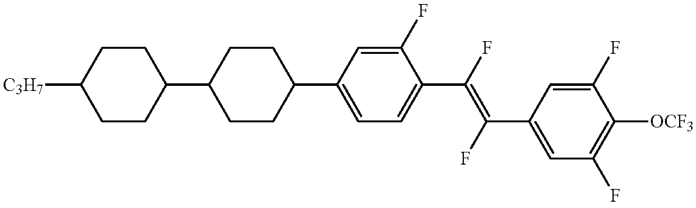 |
| 1-2-26 | 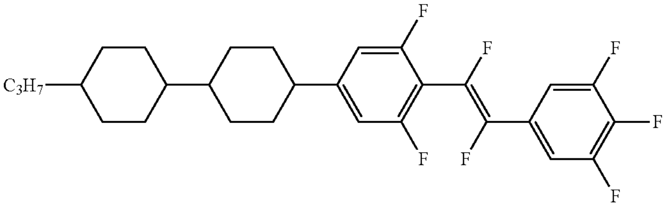 |
| 1-2-27 | 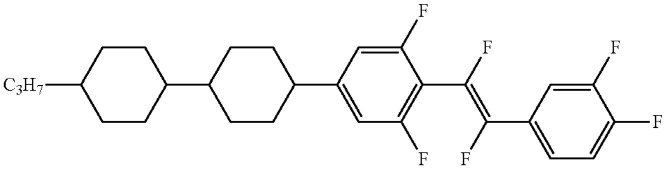 |
| 1-2-28 | 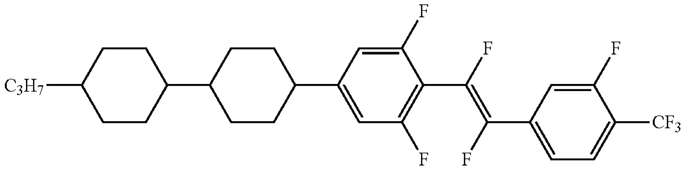 |
| 1-2-29 | 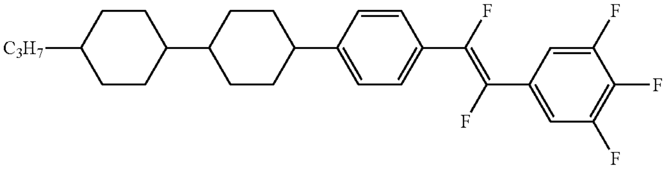 |

-continued
| No. | |
|---|---|
| 1-2-30 | 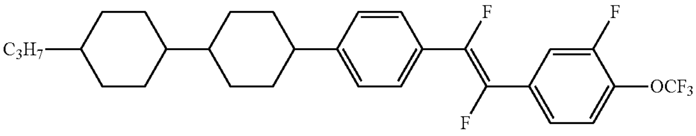 |
| 1-2-31 | 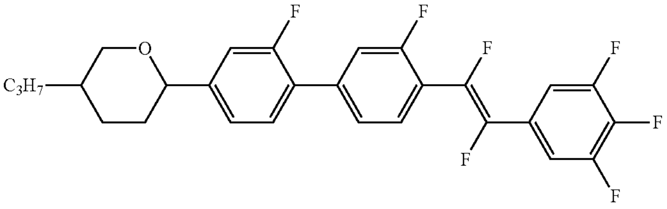 |
| 1-2-32 | 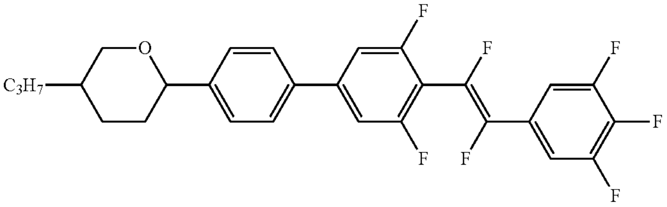 |
| 1-2-33 | 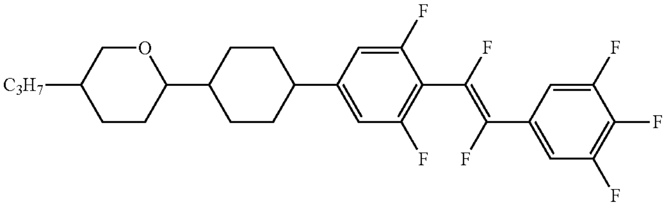 |
| 1-2-34 | 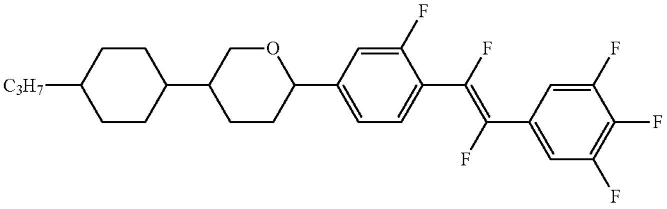 |
| 1-2-35 | 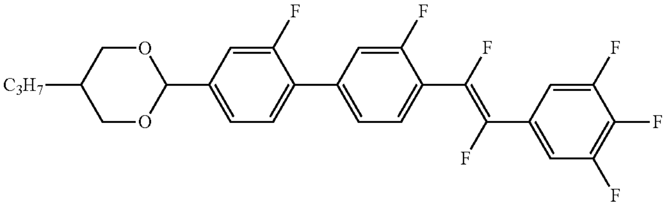 |
| 1-2-36 | 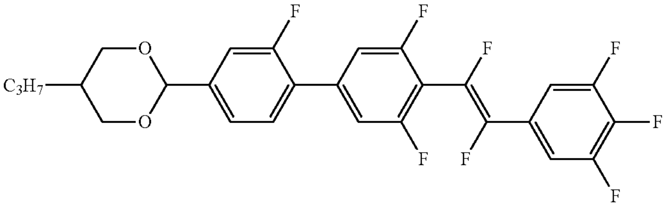 |

-continued
| No. | |
|---|---|
| 1-2-37 | 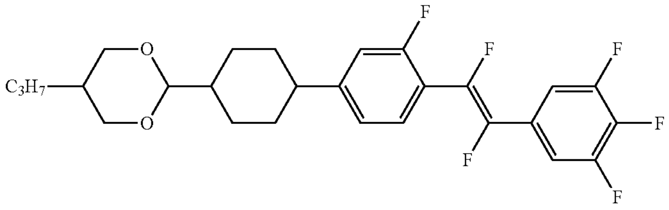 |
| 1-2-38 | 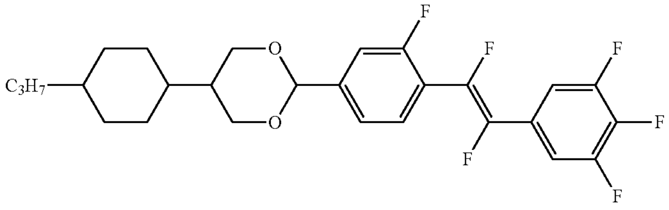 |
| 1-2-39 | 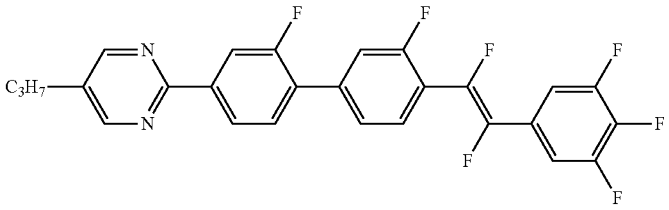 |
| 1-2-40 | 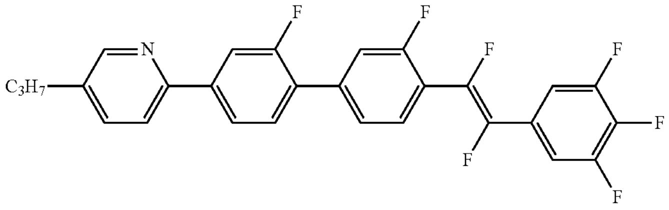 |
| 1-3-1 | 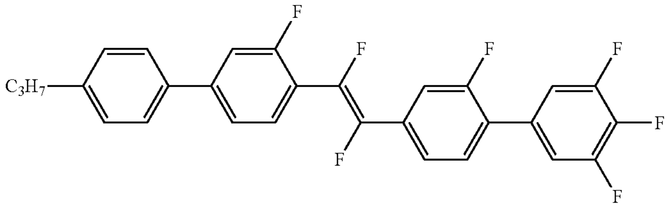<br>$T_{NI}$ = 182° C., Δ n = 0.370, Δ ε = 28.5<br>η = 93.9 mPa · s |
| 1-3-2 | 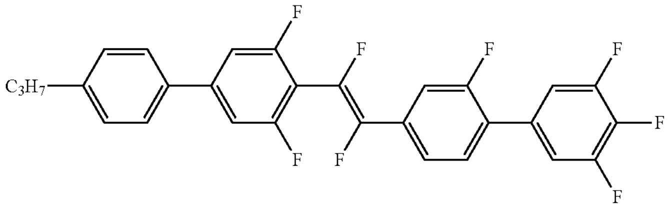 |
| 1-3-3 | 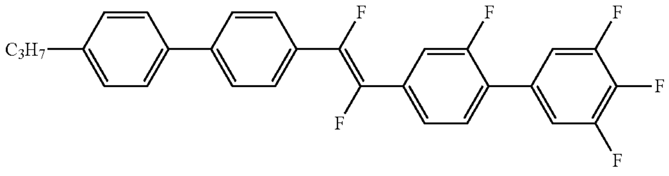 |

-continued
| No. | |
|---|---|
| 1-3-4 | 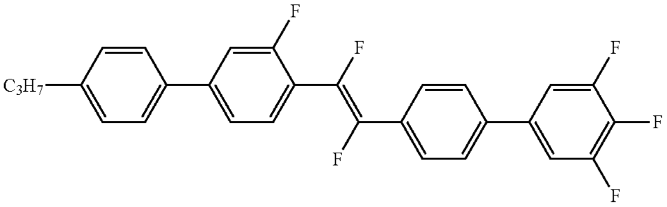 |
| 1-3-5 | 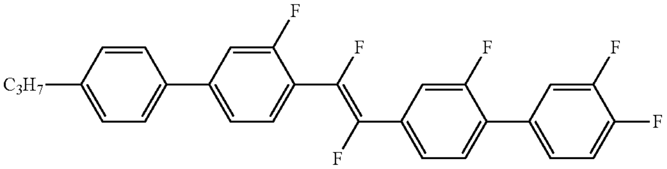 |
| 1-3-6 | 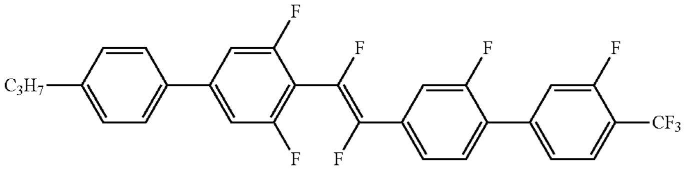 |
| 1-3-7 | 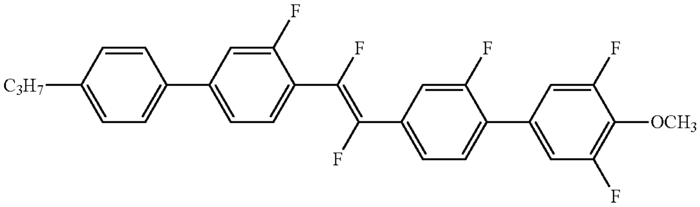 |
| 1-3-8 | 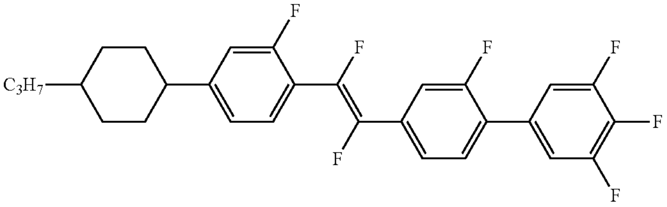 |
| 1-3-9 | 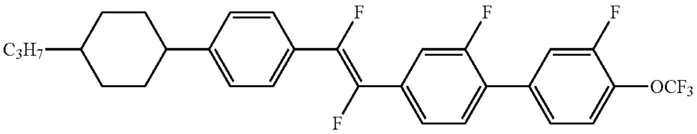 |
| 1-3-10 | 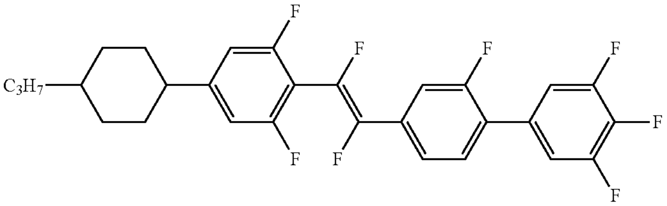 |
| 1-3-11 | 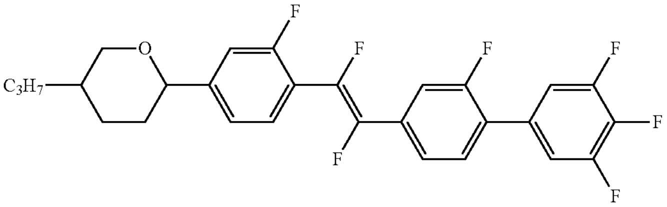 |

-continued
| No. | |
|---|---|
| 1-3-12 | 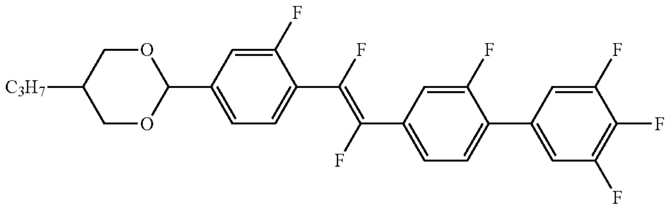 |
| 1-3-13 | 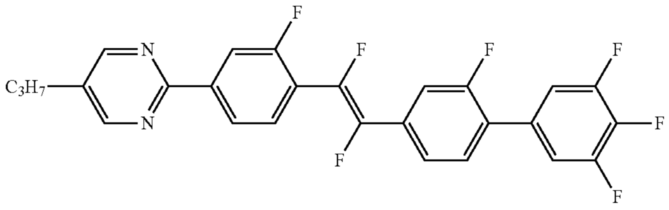 |
| 1-3-14 | 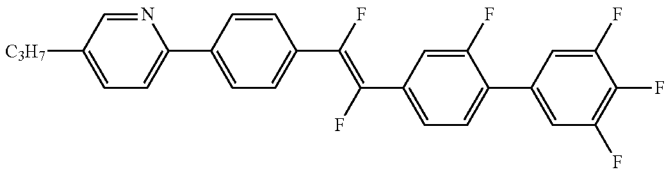 |
| 1-4-1 | 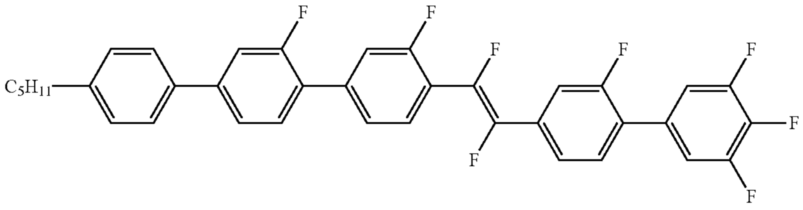 |
| 1-4-2 | 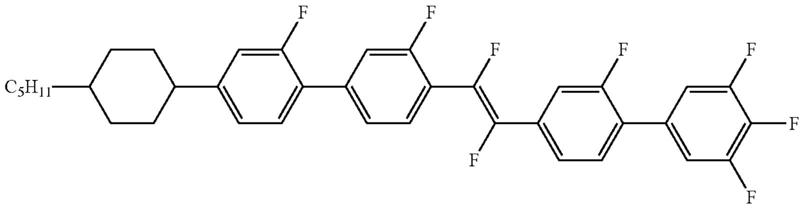 |
| 1-4-3 | 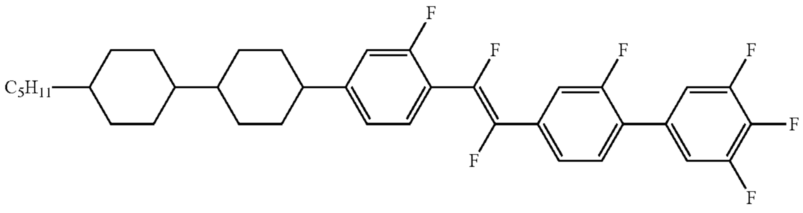 |
| 1-4-4 | 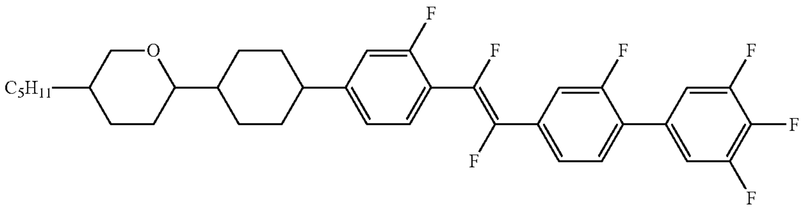 |

-continued

| No. | |
|---|---|
| 1-4-5 | 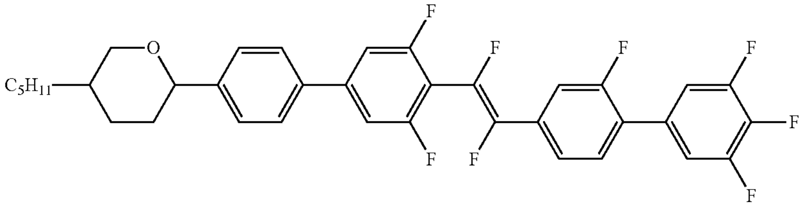 |
| 1-4-6 | 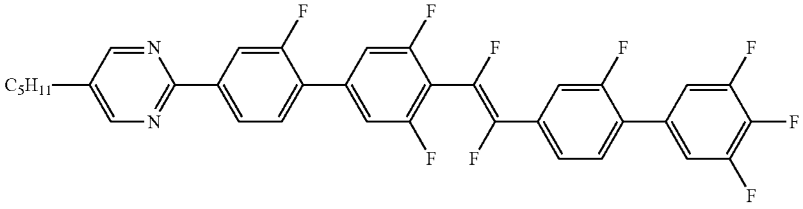 |

Comparative Example 1

As a comparative example, (E)-4-[1,2-difluoro-2-(3,4,5-trifluorophenyl)vinyl]-4'-propyl biphenyl (S-1-1) as described in WO 2006/133783 A1 was prepared.

(S-1-1)

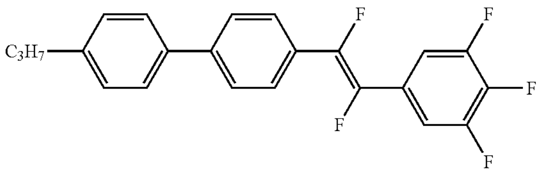

C 88.2 $S_A$ 185 N 188 I

Chemical shifts according to $^1$H-NMR analysis were as described below, and the compound obtained could be identified to be (E)-4-[1,2-difluoro-2-(3,4,5-trifluorophenyl)vinyl]-4'-propylbiphenyl.

Chemical shifts δ (ppm; $CDCl_3$); 7.80 (d, J=8.45 Hz, 2H), 7.70 (d, 8.40 Hz, 2H), 7.56 (d, J=8.10 Hz, 2H), 7.43 (dd, J=8.85 Hz, J=6.60 Hz, 2H), 7.29 (d, J=8.05 Hz, 2H), 2.65 (t, J=7.85 Hz, 2H), 1.74-1.65 (m, 2H), 0.98 (t, 7.35 Hz, 3H).

A phase transition temperature of comparative compound (S-1-1) obtained was as described below.

Phase transition temperature: C 88.2 $S_A$ 185 N 188 I.

Composition H including 90% of mother liquid crystals (A) and 10% of comparative compound (S-1-1) was prepared. Physical properties of composition H obtained were measured and values of physical properties of comparative compound (S-1-1) were calculated by extrapolating the measured values. The results were as described below.

Maximum temperature ($T_{NI}$)=143° C.; refractive index anisotropy (Δn)=0.317; dielectric anisotropy (Δ∈)=18.6; viscosity (η)=32.9 mPa·s.

Comparative compound (S-1-1) is compared with compounds (1-1-1), (1-1-11), (1-1-21), (1-1-25), (1-2-16) and (1-3-1) shown in Examples. First, when the phase transition temperatures are compared among respective compounds, compounds (1-1-1), (1-1-11) and (1-1-21) have a lower melting point than any other compounds have. When compatibility is compared among respective compounds, compound (S-1-1) can be added only by 10% to mother liquid crystals (A). In contrast, compounds (1-1-1), (1-1-11), (1-1-21), (1-1-25) and (1-2-16) can be added by 15% to mother liquid crystals (A). Therefore, the compound of the invention is definitely a more excellent compound that has a better compatibility with other compounds and can be used even at a lower temperature. Moreover, compounds (1-2-16) and (1-3-1) have a higher clearing point than any other compounds have. Therefore, the compound of the invention is definitely a more excellent compound that can be used in a wider temperature range.

Next, when comparative compound (S-1-1) is compared with compounds (1-1-1), (1-1-11), (1-1-21), (1-1-25), (1-2-16) and (1-3-1) in the values of physical properties, compounds (1-1-1), (1-1-11), (1-1-21), (1-1-25) and (1-3-1) have a larger dielectric anisotropy than any other compounds have. Therefore, the compound of the invention is definitely a more excellent compound that can decrease a threshold voltage of the composition.

A difference of comparative compound (S-1-1) from compound (1-1-1) of the invention is only as to whether lateral group $L^1$ in formula (1) is hydrogen or fluorine. However, melting points and compatibility with mother liquid crystal (A) are significantly different between comparative compound (S-1-1) and compound (1-1-1). The result indicates that lateral group $L^1$ being fluorine in a difluorostilbene is effective in improving compatibility with other compounds.

Comparative Example 2

Furthermore, (E)-1-(1,2-difluoro-2-[4-(trifluoromethoxy)phenyl]vinyl)-4-(5-pentyl tetrahydropyran-2-yl)benzene (S-2) described in WO 2006/133783 A1 was prepared as a comparative example.

(S-2)

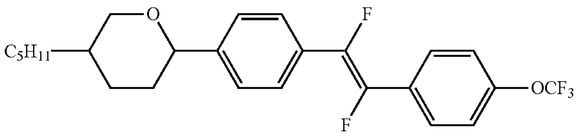

C 43.8 $S_B$ 111 $S_A$ 221 N 226 I

Chemical shifts according to $^{1}$H-NMR analysis were as described below, and the compound obtained could be identified to be (E)-1-(1,2-difluoro-2-[4-(trifluoromethoxy)phenyl]vinyl)-4-(5-pentyltetrahydropyran-2-yl)benzene.

Chemical shifts δ (ppm; $CDCl_3$); 7.79 (d, J=8.80 Hz, 2H), 7.73 (d, J=8.30 Hz, 2H), 7.44 (d, J=8.25 Hz, 2H), 7.29 (d, J=8.80 Hz, 2H), 4.32 (dd, J=11.4 Hz, J=1.90 Hz, 1H), 4.11 (dq, J=11.3 Hz, J=2.00 Hz, 1H), 3.23 (t, J=11.2 Hz, 1H), 2.01 (m, 1H), 1.90 (m, 1H), 1.74-1.53 (m, 3H), 1.41-1.24 (m, 6H), 1.24-1.10 (m, 2H), 0.90 (t, J=7.10 Hz, 3H).

A phase transition temperature of comparative compound (S-2) obtained was as described below.

Phase transition temperature: C 43.8 $S_B$ 111 $S_A$ 221 N 226 I.

Composition I including 85% of mother liquid crystals (A) and 15% of comparative compound (S-2) was prepared. Physical properties of composition I obtained were measured and values of physical properties of comparative compound (S-2) were calculated by extrapolating the measured values. The results were as described below.

Maximum temperature ($T_{NI}$)=174° C.; dielectric anisotropy ($\Delta\epsilon$)=8.93; refractive index anisotropy (Δn)=0.210; viscosity (η)=25.6 mPa·s.

When comparative compound (S-2) is compared with compounds (1-1-1), (1-1-11), (1-1-21), (1-1-25), (1-2-16) and (1-3-1) in the values of physical properties, the compounds of the invention have a larger dielectric anisotropy. Therefore, the compound of the invention is definitely a more excellent compound that can decrease a threshold voltage of the composition.

Example 14

Furthermore, typical compositions of the invention were summarized in Composition Example 1 to Composition Example 14. First, compounds as components of one of the compositions and amounts thereof (%) are shown. The compounds were described using symbols representing a left-terminal group, a bonding group, a ring and a right-terminal group according to definitions in Table 1. A configuration of 1,4-cyclohexylene and 1,3-dioxane-2,5-diyl is trans. When no symbol of a terminal group is described, the terminal group means hydrogen. Numbers described in a column of the compounds used in each Example correspond to numbers of formulas representing the compounds of the invention described above. Next, physical properties (measured values) of the compositions were shown.

Table Method for Description of Compounds using Symbols

R—($A_1$)—$Z_1$— . . . —$Z_n$—($A_n$)—R'

| 1) Left-terminal Group R— | Symbol |
|---|---|
| $C_nH_{2n+1}$— | n- |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |
| **2) Right-terminal Group —R'** | **Symbol** |
| —$C_nH_{2n+1}$ | -n |
| —$OC_nH_{2n+1}$ | —On |
| —CH=$CH_2$ | —V |
| —CH=CH—$C_nH_{2n+1}$ | —Vn |
| —$C_nH_{2n}$—CH=$CH_2$ | —nV |
| —$C_mH_{2m}$—CH=CH—$C_nH_{2n+1}$ | —mVn |
| —CH=$CF_2$ | —VFF |
| —$COOCH_3$ | —EMe |
| —F | —F |
| —Cl | —CL |
| —CN | —C |
| —$OCF_3$ | —OCF3 |
| **3) Bonding Group —$Z_n$—** | **Symbol** |
| —$C_nH_{2n}$— | n |
| —COO— | E |
| —CH=CH— | V |
| —CF=CF— | CF=CF |
| —$CH_2O$— | 1O |
| —$OCH_2$— | O1 |
| —$CF_2O$— | X |
| —C≡C— | T |
| **4) Ring Structure —$A_n$—** | **Symbol** |
| 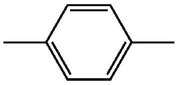 | B |

-continued
| Table Method for Description of Compounds using Symbols $R—(A_1)—Z_1— . . . —Z_n—(A_n)—R'$ | |
|---|---|
| 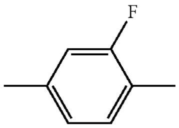 | B(F) |
| 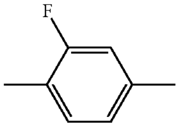 | B(2F) |
| 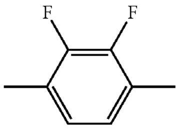 | B(2F,3F) |
| 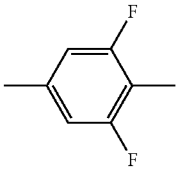 | B(F,F) |
| 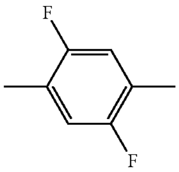 | B(2F,5F) |
| 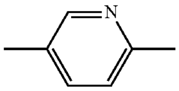 | Pr |
| 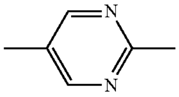 | Py |
| 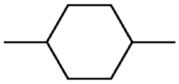 | H |
| 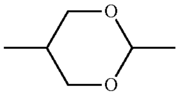 | G |
5) Example of Description
Example 1. 3-BB(F)CF═CFB(F,F)—F
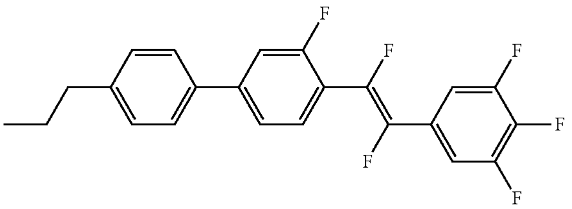 [SMILES: CCCc1ccc(-c2ccc(/C(F)=C(\F)c3cc(F)c(F)c(F)c3)c(F)c2)cc1]

-continued

Table Method for Description of Compounds using Symbols
$R-(A_1)-Z_1- \ldots -Z_n-(A_n)-R'$ Example 2. 3-HB(F)CF=CFB(F)—CF3

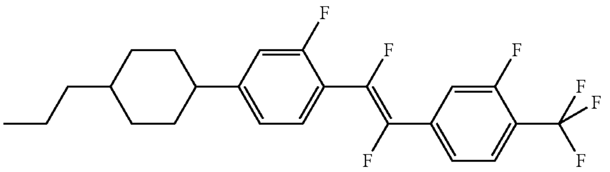 [SMILES: CCCC1CCC(c2ccc(/C(F)=C(\F)c3ccc(C(F)(F)F)c(F)c3)c(F)c2)CC1]

Example 3. 5-HBB(F)B-3

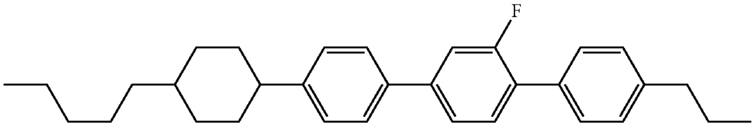 [SMILES: CCCCCC1CCC(c2ccc(-c3ccc(-c4ccc(CCC)cc4)c(F)c3)cc2)CC1]

Example 4. 3-HH-4

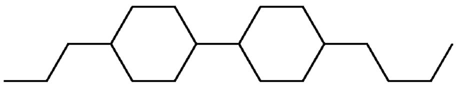 [SMILES: CCCCC1CCC(C2CCC(CCC)CC2)CC1]

Note:
Ex. is an abbreviation of an example.

Characteristic of the compositions can be measured according to the methods described below. Most of the methods are applied as described in EIAJ ED-2521A of the Standard of Electronic Industries Association of Japan, or as modified thereon. No TFT was attached to a TN device used for measurement.

Maximum Temperature of a Nematic Phase (NI; ° C.): A sample was placed on a hot plate in a melting point apparatus equipped with a polarizing microscope and was heated at a rate of 1° C. per minute. Temperature when a part of the sample began to change from a nematic phase to an isotropic liquid was measured. A higher limit of a temperature range of the nematic phase may be abbreviated as "maximum temperature."

Minimum temperature of a Nematic Phase ($T_C$; ° C.): A sample having a nematic phase was kept in freezers at temperatures of 0° C., −10° C., −20° C., −30° C. and −40° C. for 10 days, and then the liquid crystal phases were observed. For example, when the sample maintained the nematic phase at −20° C. and changed to crystals (or a smectic phase) at −30° C., $T_c$ was expressed as $T_c \leq -20$° C. A lower limit of a temperature range of the nematic phase may be abbreviated as "minimum temperature."

Viscosity (bulk viscosity; measured at 20° C.; mPa·s): A cone-plate (E type) viscometer was used for measurement.

Viscosity (rotational viscosity; δ1; measured at 25° C.; mPa·s):

1) A sample having a positive dielectric anisotropy: Measurement was carried out according to the method described in M. Imai et al., Molecular Crystals and Liquid Crystals, Vol. 259, 37 (1995). A sample was put in a TN device in which a twist angle was 0 degrees and a distance (cell gap) between two glass substrates was 5 micrometers. A voltage was stepwise applied to the TN device in the range of 16 V to 19.5 V at an increment of 0.5 V. After a period of 0.2 second with no application, a voltage was applied repeatedly under the conditions of only one of rectangular waves (rectangular pulse; 0.2 second) and no application (2 seconds). A peak current and a peak time of a transient current generated by the application were measured. A value of rotational viscosity was obtained from the measured values and a calculation equation (8) on page 40 of the paper presented by M. Imai et al. The value of the dielectric anisotropy required for the calculation was determined by means of the device used in measuring the rotational viscosity, according to the method for measuring the dielectric anisotropy as described below.

2) A sample having a negative dielectric anisotropy: Measurement was carried out according to the method described in M. Imai et al., Molecular Crystals and Liquid Crystals, Vol. 259, 37 (1995). A sample was put in a VA device in which a distance (cell gap) between two glass substrates was 20 micrometers. A voltage was stepwise applied to the device in the range of 30 V to 50 V at an increment of 1 V. After a period of 0.2 second with no application, a voltage was applied repeatedly under the conditions of only one of rectangular waves (rectangular pulse; 0.2 second) and no application (2 seconds). A peak current and a peak time of a transient current generated by the application were measured. A value of rotational viscosity was obtained from the measured values and a calculation equation (8) on page 40 of the paper presented by M. Imai et al. As for the value of the dielectric anisotropy required for the calculation, a value obtained by measurement according the method as described in the dielectric anisotropy below was used.

Refractive Index Anisotropy (Δn; measured at 25° C.): Measurement was carried out by means of an Abbe refractometer with a polarizing plate mounted on an ocular, using light at a wavelength of 589 nanometers. A surface of a main prism was rubbed in one direction, and then a sample was added dropwise onto the main prism. A refractive index (n||) was measured when the direction of polarized light was parallel to the direction of rubbing. A refractive index (n⊥) was measured when the direction of polarized light was perpendicular to the direction of rubbing. The value of the refractive index anisotropy was calculated from the equation: Δn=n||− n⊥. When a sample was a composition, the refractive index anisotropy was measured according to the method.

Dielectric Anisotropy (Δ∈; measured at 25° C.):

1) A composition having a positive dielectric anisotropy: A sample was put in a liquid crystal cell in which a distance (gap) between two glass substrates was about 9 micrometers and a twist angle was 80 degrees. A voltage of 20 V was applied to the cell, and a dielectric constant (4) in the major axis direction of liquid crystal molecules was measured. A voltage of 0.5 V was applied to the cell, and a dielectric constant (∈⊥) in the minor axis direction of the liquid crystal molecules was measured. The value of the dielectric anisotropy was calculated from the equation: Δ∈=∈||−∈⊥.

2) A composition having a negative dielectric anisotropy: A sample was put in a liquid crystal cell processed to a homeotropic alignment, a voltage of 0.5 V was applied, and a dielectric constant (∈||) was measured. A sample was put in a liquid crystal cell processed to a homogeneous alignment, a voltage of 0.5 V was applied, and a dielectric constant (∈⊥) was measured. The value of the dielectric anisotropy was calculated from the equation: Δ∈=∈||−∈⊥.

Threshold Voltage (Vth; measured at 25° C.; V): When a sample was a compound, a threshold voltage was measured after mixing the compound with a suitable composition. The threshold voltage of the compound is expressed in terms of an extrapolated value.

1) A composition having a positive dielectric anisotropy: A sample was put in a normally white mode liquid crystal display device in which a distance (gap) between two glass substrates was (0.5/Δn) micrometers and a twist angle was 80 degrees. Δn is expressed in terms of the value of the refractive index anisotropy measured according to the above method. Rectangular waves having a frequency of 32 Hz were applied to the device. A voltage of the rectangular waves was increased and a value of voltage when the transmittance of light passing through the device reached 90% was measured.

2) A composition having a negative dielectric anisotropy: A sample was put in a normally black mode liquid crystal display device processed to a homeotropic alignment in which a distance (cell gap) between two glass substrates was 9 micrometers. Rectangular waves having a frequency of 32 Hz were applied to the device. A voltage of the rectangular waves was increased and a value of voltage when the transmittance of light passing through the device reached 10% was measured.

Voltage Holding Ratio (VHR; measured at 25° C.; %): A TN device used for measurement had a polyimide alignment film, and a distance (cell gap) between two glass substrates was 6 micrometers. A sample was put in the device, and then the device was sealed with an ultraviolet-polymerizable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B was an area without decay. A voltage holding ratio is a percentage of area A to area B.

Helical Pitch (measured at 20° C.; μm): For measuring a helical pitch, the Cano wedge cell method was employed. A sample was injected into a Cano wedge cell, and a distance (a; unit: μm) between disclination lines observed from the cell was measured. A helical pitch (P) was calculated according to an equation: P=2×a×tan θ, wherein θ is an angle between two sheets of glass in the wedge cell.

A ratio of the components (percentage) is expressed in terms of weight percent (%) based on the total weight of the components.

Composition Example 1

| | | |
|---|---|---|
| 3-BB(F)CF=CFB(F,F)-F | (1-1-1) | 7% |
| 3-BB(F,F)CF=CFB(F,F)-F | (1-1-11) | 5% |
| 3-BEB(F)-C | (5-14) | 4% |
| 4-BEB(F)-C | (5-14) | 12% |
| 1V2-BEB(F,F)-C | (5-15) | 16% |
| 3-HB-O2 | (11-5) | 10% |
| 3-HH-4 | (11-1) | 3% |
| 3-HHB-F | (3-1) | 3% |
| 3-HHB-1 | (12-1) | 8% |
| 3-HHB-O1 | (12-1) | 4% |
| 3-HBEB-F | (3-37) | 4% |
| 3-HHEB-F | (3-10) | 7% |
| 3-H2BTB-2 | (12-16) | 4% |
| 3-H2BTB-3 | (12-16) | 4% |
| 3-H2BTB-4 | (12-16) | 4% |
| 3-HB(F)TB-2 | (12-17) | 5% |

NI = 80.6° C.; Δn = 0.154; Δε = 28.3; Vth = 1.05 V; η = 36.6 mPa · sec.

Composition Example 2

| | | |
|---|---|---|
| 3-HB(F)CF=CFB(F,F)-F | (1-1-21) | 7% |
| 3-HB(F)CF=CFB(F)-CF3 | (1-1-25) | 5% |
| 2-HB-C | (5-1) | 5% |
| 3-HB-C | (5-1) | 12% |
| 3-HB-O2 | (11-5) | 15% |
| 2-BTB-1 | (11-10) | 3% |
| 3-HHB-F | (3-1) | 4% |
| 3-HHB-1 | (12-1) | 8% |
| 3-HHB-3 | (12-1) | 14% |
| 3-HHEB-F | (3-10) | 4% |
| 5-HHEB-F | (3-10) | 4% |
| 3-HHB(F)-F | (3-2) | 7% |
| 5-HHB(F)-F | (3-2) | 7% |
| 3-HHB(F,F)-F | (3-3) | 5% |

NI = 96.8° C.; Δn = 0.111; Δε = 6.3; Vth = 2.09 V; η = 19.8 mPa · sec.

Composition Example 3

| | | |
|---|---|---|
| 3-BB(F)CF=CFB(F,F)-F | (1-1-1) | 4% |
| 3-HB(F)CF=CFB(F,F)-F | (1-1-21) | 4% |
| 3-BEB(F)-C | (5-14) | 8% |
| V-HB-C | (5-1) | 8% |
| 1V-HB-C | (5-1) | 8% |
| 3-HB-O2 | (11-5) | 3% |
| 3-HH-2V | (11-1) | 14% |
| 3-HH-2V1 | (11-1) | 7% |
| V2-HHB-1 | (12-1) | 15% |
| 3-HHB-1 | (12-1) | 5% |
| 3-HHEB-F | (3-10) | 7% |
| 3-H2BTB-2 | (12-16) | 6% |
| 3-H2BTB-3 | (12-16) | 6% |
| 3-H2BTB-4 | (12-16) | 5% |

NI = 102.7° C.; Δn = 0.140; Δε = 9.0; Vth = 2.21 V; η = 17.9 mPa · sec.

A helical pitch was 61.2 micrometers when 0.25 part by weight of optically active compound (Op-5) was added to 100 parts by weight of the composition described above.

Composition Example 4

| | | |
|---|---|---|
| 3-BB(F,F)CF=CFB(F,F)-F | (1-1-11) | 5% |
| 3-HB(F)CF=CFB(F)-CF3 | (1-1-25) | 5% |
| 5-BEB(F)-C | (5-14) | 5% |
| V-HB-C | (5-1) | 11% |
| 5-PyB-C | (5-9) | 6% |
| 4-BB-3 | (11-8) | 11% |
| 3-HH-2V | (11-1) | 10% |
| 5-HH-V | (11-1) | 5% |
| V-HHB-1 | (12-1) | 3% |
| V2-HHB-1 | (12-1) | 15% |
| 3-HHB-1 | (12-1) | 9% |
| 1V2-HBB-2 | (12-4) | 10% |
| 3-HHEBH-3 | (13-6) | 5% |

NI = 89.0° C.; $\Delta n$ = 0.129; $\Delta\epsilon$ = 7.2; Vth = 1.88 V; $\eta$ = 21.2 mPa · sec.

Composition Example 5

| | | |
|---|---|---|
| 3-BB(F)CF=CFB(F,F)-F | (1-1-1) | 5% |
| 3-HB(F)CF=CFB(F)-CF3 | (1-1-25) | 5% |
| 1V2-BEB(F,F)-C | (5-15) | 6% |
| 3-HB-C | (5-1) | 8% |
| 2-BTB-1 | (11-10) | 10% |
| 5-HH-VFF | (11-1) | 30% |
| 3-HHB-1 | (12-1) | 4% |
| VFF-HHB-1 | (12-1) | 8% |
| VFF2-HHB-1 | (12-1) | 11% |
| 3-H2BTB-2 | (12-16) | 5% |
| 3-H2BTB-3 | (12-16) | 4% |
| 3-H2BTB-4 | (12-16) | 4% |

NI = 86.3° C.; $\Delta n$ = 0.139; $\Delta\epsilon$ = 7.4; Vth = 2.03 V.

Composition Example 6

| | | |
|---|---|---|
| 3-BB(F,F)CF=CFB(F,F)-F | (1-1-11) | 4% |
| 3-HB(F)CF=CFB(F,F)-F | (1-1-21) | 3% |
| 5-HB-CL | (2-2) | 16% |
| 3-HH-4 | (11-1) | 12% |
| 3-HH-5 | (11-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 5% |
| 1O1-HBBH-5 | (13-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 112.9° C.; $\Delta n$ = 0.097; $\Delta\epsilon$ = 5.0; Vth = 2.19 V; $\eta$ = 20.9 mPa · sec.

Composition Example 7

| | | |
|---|---|---|
| 3-BB(F)B(F)CF=CFB(F,F)-F | (1-2-1) | 3% |
| 3-BB(F)CF=CFB(F)B(F,F)-F | (1-3-1) | 3% |
| 3-HHB(F,F)-F | (3-3) | 9% |

-continued

| | | |
|---|---|---|
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 21% |
| 5-HBB(F,F)-F | (3-24) | 20% |
| 3-H2BB(F,F)-F | (3-27) | 8% |
| 5-HHBB(F,F)-F | (4-6) | 3% |
| 5-HH2BB-F | (4-13) | 2% |
| 3-HH2BB(F,F)-F | (4-15) | 3% |
| 1O1-HBBH-5 | (13-1) | 4% |

Composition Example 8

| | | |
|---|---|---|
| 3-HB(F)B(F,F)CF=CFB(F)-OCF3 | (1-2-17) | 5% |
| 5-HB(F)B(F)CF=CFB(F)B(F,F)-F | (1-4-2) | 3% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 5% |
| 3-HH2B-OCF3 | (3-4) | 4% |
| 5-HH2B-OCF3 | (3-4) | 4% |
| 3-HHB(F,F)-OCF2H | (3-3) | 4% |
| 3-HHB(F,F)-OCF3 | (3-3) | 5% |
| 3-HH2B(F)-F | (3-5) | 3% |
| 3-HBB(F)-F | (3-23) | 5% |
| 5-HBB(F)-F | (3-23) | 7% |
| 5-HBBH-3 | (13-1) | 3% |
| 3-HB(F)BH-3 | (13-2) | 3% |

Composition Example 9

| | | |
|---|---|---|
| 3-BB(F)CF=CFB(F,F)-F | (1-1-1) | 3% |
| 3-BB(F)B(F)CF=CFB(F,F)-F | (1-2-1) | 3% |
| 5-HB-CL | (2-2) | 8% |
| 3-HH-4 | (11-1) | 8% |
| 3-HHB-1 | (12-1) | 2% |
| 3-HHB(F,F)-F | (3-3) | 8% |
| 3-HBB(F,F)-F | (3-24) | 20% |
| 5-HBB(F,F)-F | (3-24) | 15% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 6% |

Composition Example 10

| | | |
|---|---|---|
| 3-BB(F,F)CF=CFB(F,F)-F | (1-1-11) | 4% |
| 3-BB(F)CF=CFB(F)B(F,F)-F | (1-3-1) | 4% |
| 3-HB-CL | (2-2) | 3% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-19) | 15% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF3 | (3-21) | 8% |
| 5-H4HB(F,F)-CF3 | (3-21) | 10% |
| 5-H2HB(F,F)-F | (3-15) | 5% |

-continued

| | | |
|---|---|---|
| 5-H4HB(F,F)-F | (3-21) | 7% |
| 2-H2BB(F)-F | (3-26) | 5% |
| 3-H2BB(F)-F | (3-26) | 5% |
| 3-HBEB(F,F)-F | (3-39) | 5% |

Composition Example 11

| | | |
|---|---|---|
| 3-HB(F)CF=CFB(F,F)-F | (1-1-21) | 5% |
| 3-HB(F)B(F,F)CF=CFB(F)-OCF3 | (1-2-17) | 5% |
| 5-HB-CL | (2-2) | 7% |
| 7-HB(F,F)-F | (2-4) | 3% |
| 3-HH-4 | (11-1) | 10% |
| 3-HH-5 | (11-1) | 5% |
| 3-HB-O2 | (11-5) | 15% |
| 3-HHB-1 | (12-1) | 8% |
| 3-HHB-O1 | (12-1) | 5% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 6% |
| 3-H2HB(F,F)-F | (3-15) | 5% |
| 4-H2HB(F,F)-F | (3-15) | 5% |

Composition Example 12

| | | |
|---|---|---|
| 3-BB(F)CF=CFB(F,F)-F | (1-1-1) | 5% |
| 3-BB(F,F)CF=CFB(F,F)-F | (1-1-11) | 5% |
| 5-HB-CL | (2-2) | 3% |
| 7-HB(F)-F | (2-3) | 7% |
| 3-HH-4 | (11-1) | 9% |
| 3-HH-EMe | (11-2) | 23% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 5-HGB(F,F)-F | (3-103) | 6% |
| 2-H2GB(F,F)-F | (3-106) | 4% |
| 5-GHB(F,F)-F | (3-109) | 7% |

NI = 81.2° C.; $\Delta n = 0.080$; $\Delta\epsilon = 6.8$; $\eta = 21.7$ mPa · sec.

Composition Example 13

| | | |
|---|---|---|
| 3-HB(F)CF=CFB(F,F)-F | (1-1-21) | 5% |
| 3-HB(F)CF=CFB(F)-CF3 | (1-1-25) | 5% |
| 3-HB-O2 | (11-5) | 10% |
| 5-HB-CL | (2-2) | 13% |
| 3-HBB(F,F)-F | (3-24) | 7% |
| 3-PyB(F)-F | (2-15) | 10% |
| 5-PyB(F)-F | (2-15) | 10% |
| 3-PyBB-F | (3-80) | 10% |
| 4-PyBB-F | (3-80) | 10% |
| 5-PyBB-F | (3-80) | 10% |
| 5-HBB(F)B-3 | (13-5) | 10% |

NI = 85.3° C.; $\Delta n = 0.184$; $\Delta\epsilon = 9.7$; Vth = 1.52 V; $\eta = 38.6$ mPa · sec.

Composition Example 14

| | | |
|---|---|---|
| 3-BB(F)CF=CFB(F)B(F,F)-F | (1-3-1) | 5% |
| 5-HB(F)B(F)CF=CFB(F)B(F,F)-F | (1-4-2) | 4% |
| 3-HH-V | (11-1) | 25% |
| 3-BB(F,F)XB(F,F)-F | (3-97) | 18% |
| 3-HHB-1 | (12-1) | 2% |
| 2-HBB-F | (3-22) | 3% |
| 3-HBB-F | (3-22) | 4% |
| 3-HHB-CL | (3-1) | 6% |
| 1-BB(F)B-2V | (12-6) | 6% |
| 2-BB(F)B-2V | (12-6) | 6% |
| 3-BB(F)B-2V | (12-6) | 3% |
| 2-HHB(F,F)-F | (3-3) | 4% |
| 3-HHB(F,F)-F | (3-3) | 4% |
| 4-BB(F)B(F,F)XB(F,F)-F | (4-46) | 10% |

INDUSTRIAL APPLICABILITY

The invention provides a novel liquid crystal compound having general physical properties necessary for the compound, namely, stability to heat, light and so forth, a wide temperature range of a liquid crystal phase, a high clearing point, a good compatibility with other compounds, a large refractive index anisotropy, a large dielectric anisotropy and a small viscosity. The invention also provides a new liquid crystal composition having desirable characteristics by using the liquid crystal compound as a component and suitably selecting a ring, a substituent, a bonding group and so forth constituting the compound. Furthermore, a liquid crystal display device using the liquid crystal composition can be widely used for a display for a watch, a calculator, a personal computer or the like.

What is claimed is:

1. A compound represented by formula (1):

(1)

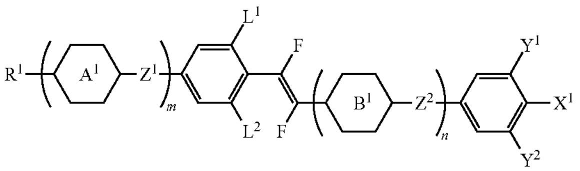

wherein, in formula (1), $R^1$ is alkyl having 1 to 20 carbons, and in the alkyl, arbitrary —$CH_2$— may be replaced by —O— or —S—, and arbitrary —$CH_2CH_2$— may be replaced by —CH=CH—; ring $A^1$ is independently 1,4-cyclohexylene, 1,3-dioxane-2,5-diyl, tetrahydropyran-2,5-diyl, pyrimidine-2,5-diyl, pyridine-2,5-diyl, 1,4-phenylene, or 1,4-phenylene in which arbitrary hydrogen is replaced by halogen; ring $B^1$ is independently 1,4-phenylene, 3-fluoro-1,4-phenylene, 3,5-difluoro-1,4-phenylene, 3-chloro-1,4-phenylene or 3-chloro-5-fluoro-1,4-phenylene; $Z^1$ and $Z^2$ are independently a single bond, —$CH_2CH_2$—, —CH=CH— or —C≡C—; $L^2$, $Y^1$ and $Y^2$ are independently hydrogen, fluorine or chlorine; $X^1$ is hydrogen, halogen, —C≡N, —N=C=S, —$SF_5$— or alkyl having 1 to 10 carbons, and in the alkyl, arbitrary —$CH_2$— may be replaced by —O— or —S—, and arbitrary —$CH_2CH_2$— may be replaced by —CH=CH—, and arbitrary hydrogen may be replaced by halogen; m is 1 or 2; n is 1; and $L^1$ is fluorine.

2. The compound according to claim 1, wherein, in formula (1), $R^1$ is alkyl having 1 to 20 carbons, alkenyl having 2 to 20 carbons, alkoxy having 1 to 19 carbons, alkenyloxy having 2 to 19 carbons or alkylthio having 1 to 19 carbons; and $X^1$ is hydrogen, halogen, —C≡N, —N=C=S, —$SF_5$, alkyl having 1 to 10 carbons, alkenyl having 2 to 10 carbons, alkoxy having 1 to 9 carbons, alkenyloxy having 2 to 9 carbons, thioalkyl having 1 to 9 carbons, —$CH_2F$, —$CHF_2$, —$CF_3$, —$(CH_2)_2$—F, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F, —$(CF_2)_5$—F, —$OCH_2F$, —$OCHF_2$, —$OCF_3$, —O—$(CH_2)_2$—F, —$OCF_2CH_2F$, —$OCF_2CHF_2$, —$OCH_2CF_3$, —O—$(CH_2)_3$—F, —O—$(CF_2)_3$—F, —$OCF_2CHFCF_3$, —$OCHFCF_2CF_3$, —$O(CH_2)_4$—F, —O—$(CF_2)_4$—F, —O—$(CH_2)_5$—F, —O—$(CF_2)_5$—F, —CH=CHF, —CH=$CF_2$, —CF=CHF, —CH=$CHCH_2F$, —CH=$CHCF_3$, —$(CH_2)_2$—CH=$CF_2$, —$CH_2CH$=$CHCF_3$ or —CH=$CHCF_2CF_3$.

3. The compound according to claim 1, wherein, in formula (1), $R^1$ is alkyl having 1 to 12 carbons, alkenyl having 2 to 12 carbons, alkoxy having 1 to 12 carbons or alkenyloxy having 2 to 12 carbons; $Z^1$ and $Z^2$ are independently a single bond, —$CH_2CH_2$— or —CH=CH—; and $X^1$ is fluorine, chlorine, —C≡N, —$CF_3$, —$CHF_2$, —$CH_2F$, —$OCF_3$, —$OCHF_2$ or —$OCH_2F$.

4. The compound according to claim 1, wherein, in formula (1), $R^1$ is alkyl having 1 to 12 carbons, alkenyl having 2 to 12 carbons or alkoxy having 1 to 12 carbons; and $Z^1$ and $Z^2$ are independently a single bond or —$CH_2CH_2$—, and $X^1$ is fluorine, chlorine, —$CF_3$ or —$OCF_3$.

5. The compound according to claim 1, represented by any one of formula (1-3) to formula (1-4):

(1-3)

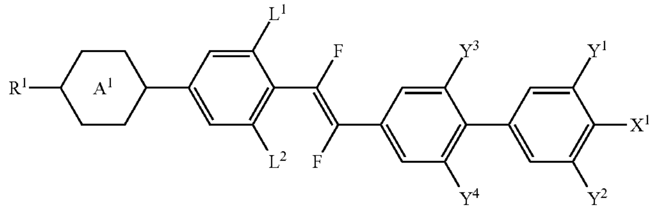

(1-4)

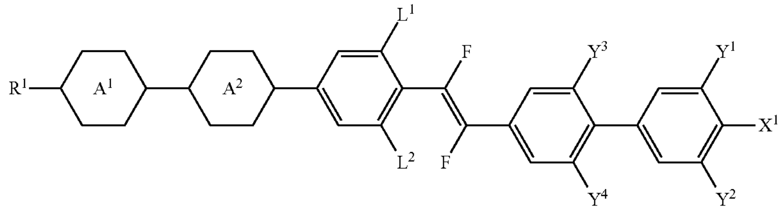

wherein, in the formulas, $R^1$ is alkyl having 1 to 12 carbons or alkenyl having 2 to 12 carbons; ring $A^1$ and ring $A^2$ are independently 1,4-cyclohexylene, 1,3-dioxane-2,5-diyl, tetrahydropyran-2,5-diyl, pyrimidine-2,5-diyl, pyridine-2,5-diyl, 1,4-phenylene, or 1,4-phenylene in which arbitrary hydrogen is replaced by halogen; $L^1$ is fluorine; $L^2$, $Y^1$, $Y^2$, $Y^3$ and $Y^4$ are independently hydrogen, fluorine or chlorine; and $X^1$ is fluorine, chlorine, —$CF_3$ or —$OCF_3$.

6. The compound according to claim 1, represented by any one of formula (1-21) to formula (1-33):

(1-21)

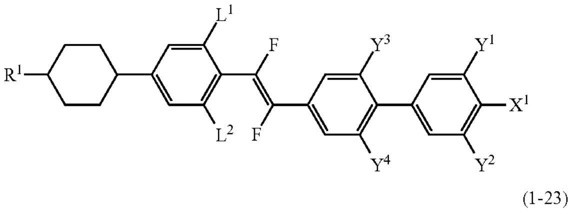

(1-22)

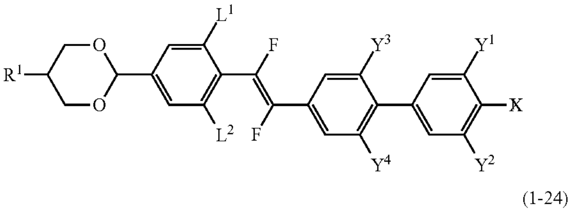

(1-23)

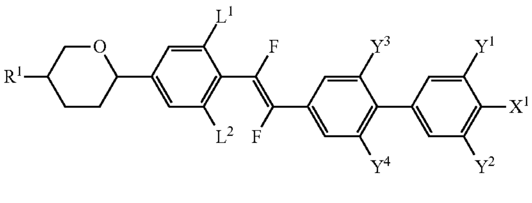

(1-24)

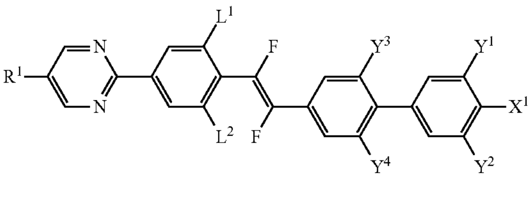

-continued
(1-25)
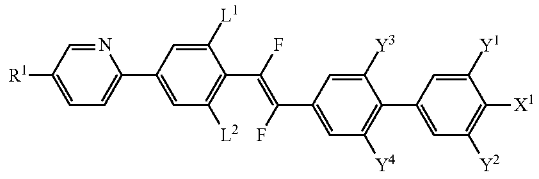
(1-26)
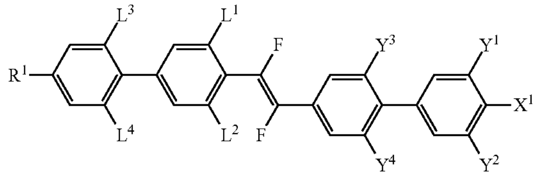
(1-27)
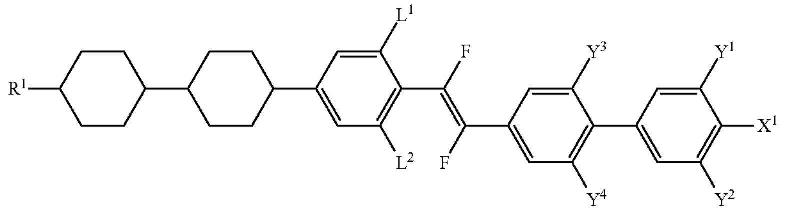
(1-28)
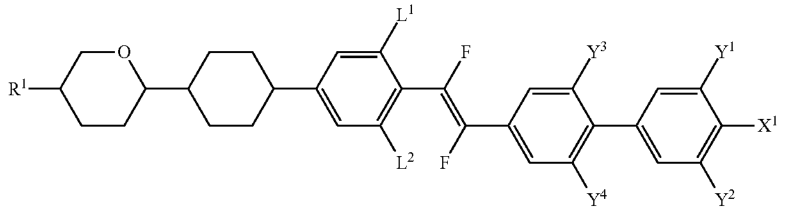
(1-29)
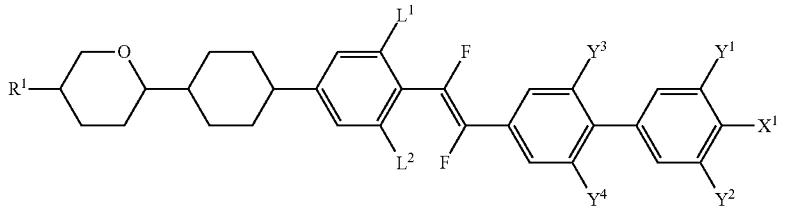
(1-30)
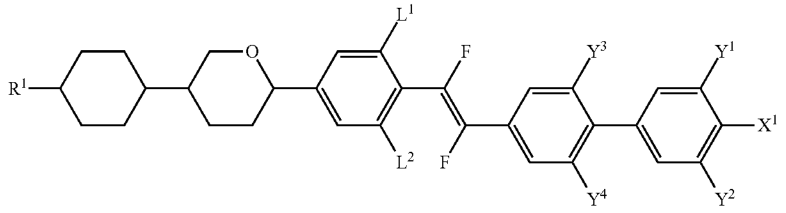
(1-31)
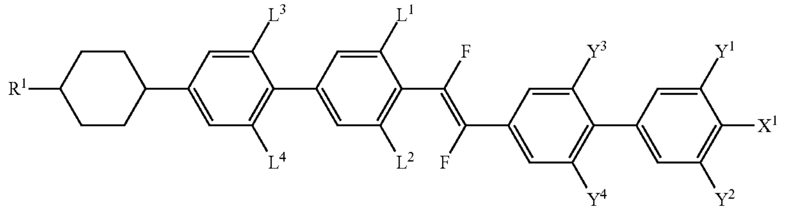
(1-32)
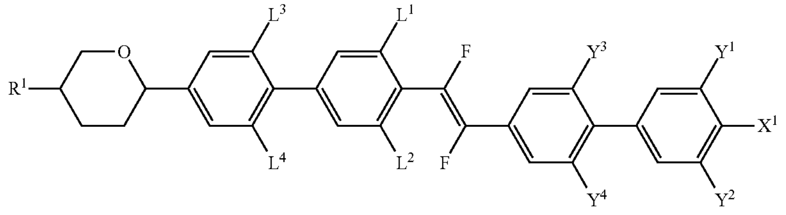

-continued (1-33)

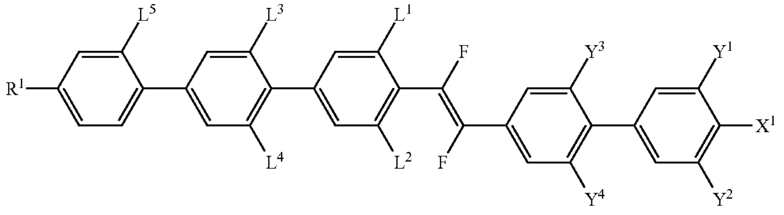

wherein, in the formulas, $R^1$ is alkyl having 1 to 12 carbons; $L^1$ is fluorine; $L^2$, $L^3$, $L^4$, $L^5$, $Y^1$, $Y^2$, $Y^3$ and $Y^4$ are independently hydrogen, chlorine or fluorine; and $X^1$ is fluorine, chlorine, $—CF_3$ or $—OCF_3$.

7. A liquid crystal composition, containing at least one compound according to claim 5 as one component, and including two or more components.

8. The liquid crystal composition according to claim 7, containing at least one compound selected from the group of compounds represented by formulas (2), (3) and (4) as one component:

(2)

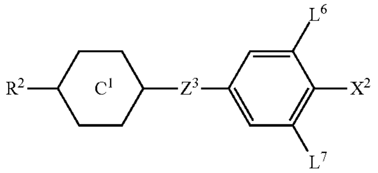

(3)

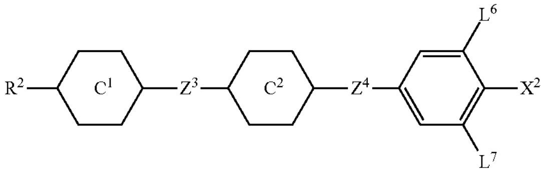

(4)

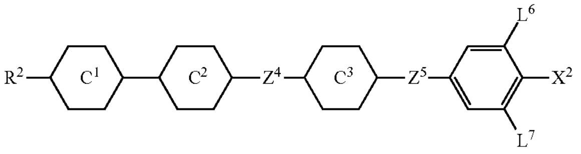

wherein, in the formulas, $R^2$ is alkyl having 1 to 10 carbons or alkenyl having 2 to 10 carbons, and in the alkyl and the alkenyl, arbitrary hydrogen may be replaced by fluorine, and arbitrary $—CH_2—$ may be replaced by $—O—$; $X^2$ is fluorine, chlorine, $—OCF_3$, $—OCHF_2$, $—CF_3$, $—CHF_2$, $—CH_2F$, $—OCF_2CHF_2$ or $—OCF_2CHFCF_3$; ring $C^1$, ring $C^2$ and ring $C^3$ are independently 1,4-cyclohexylene, 1,3-dioxane-2,5-diyl, pyrimidine-2,5-diyl, tetrahydropyran-2,5-diyl, 1,4-phenylene, or 1,4-phenylene in which arbitrary hydrogen is replaced by fluorine; $Z^3$, $Z^4$ and $Z^5$ are independently $—(CH_2)_2—$, $—(CH_2)_4—$, $—COO—$, $—CF_2O—$, $—OCF_2—$, $—CH{=}CH—$, $—C{\equiv}C—$, $—CH_2O—$ or a single bond; and $L^6$ and $L^7$ are independently hydrogen or fluorine.

9. The liquid crystal composition according to claim 7, containing at least one compound selected from the group of compounds represented by formula (5) as one component:

(5)

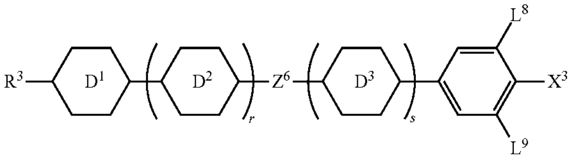

wherein, in formula (5), $R^3$ is alkyl having 1 to 10 carbons or alkenyl having 2 to 10 carbons, and in the alkyl and the alkenyl, arbitrary hydrogen may be replaced by fluorine, and arbitrary $—CH_2—$ may be replaced by $—O—$; $X^3$ is $—C{\equiv}N$ or $—C{\equiv}C—C{\equiv}N$; ring $D^1$, ring $D^2$ and ring $D^3$ are independently 1,4-cyclohexylene, 1,4-phenylene, 1,4-phenylene in which arbitrary hydrogen is replaced by fluorine, 1,3-dioxane-2,5-diyl, tetrahydropyran-2,5-diyl, or pyrimidine-2,5-diyl; $Z^6$ is $—(CH_2)_2—$, $—COO—$, $—CF_2O—$, $—OCF_2—$, $—C{\equiv}C—$, $—CH_2O—$ or a single bond; $L^8$ and $L^9$ are independently hydrogen or fluorine; and r and s are independently 0 or 1.

10. The liquid crystal composition according to claim 7, containing at least one compound selected from the group of compounds represented by formulas (6), (7), (8), (9) and (10) as one component:

(6)

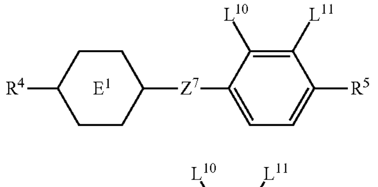

(7)

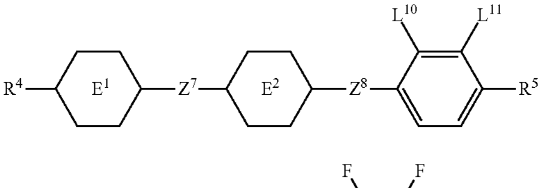

(8)

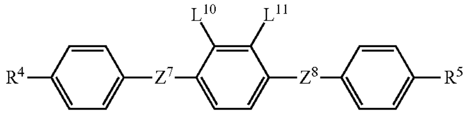

(9)

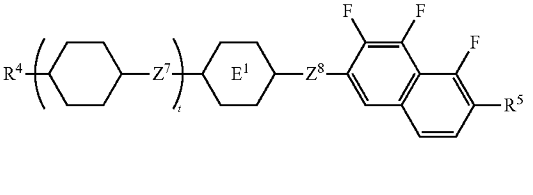

-continued (10)

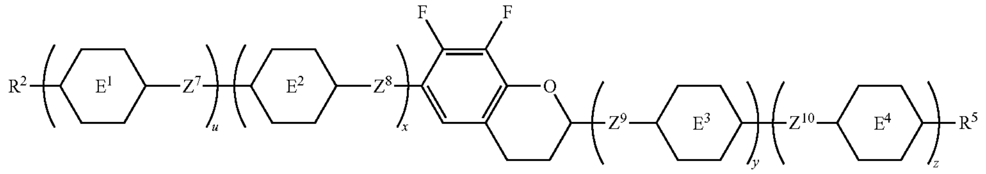

wherein, in the formulas, $R^4$ and $R^5$ are independently alkyl having 1 to 10 carbons or alkenyl having 2 to 10 carbons, and in the alkyl and the alkenyl, arbitrary hydrogen may be replaced by fluorine, and arbitrary $—CH_2—$ may be replaced by —O—; ring $E^1$, ring $E^2$, ring $E^3$ and ring $E^4$ are independently 1,4-cyclohexylene, 1,4-cyclohexenylene, 1,4-phenylene, 1,4-phenylene in which arbitrary hydrogen is replaced by fluorine, tetrahydropyran-2,5-diyl or decahydronaphthalene-2,6-diyl; $Z^7$, $Z^8$, $Z^9$ and $Z^{10}$ are independently $—(CH_2)_2—$, —COO—, $—CH_2O—$, $—OCF_2—$, $—OCF_2—(CH_2)_2—$ or a single bond; $L^{10}$ and $L^{11}$ are independently fluorine or chlorine; and t, u, x, y and z are independently 0 or 1, and a sum of u, x, y and z is 1 or 2.

11. The liquid crystal composition according to claim 7, containing at least one compound selected from the group of compounds represented by formulas (11), (12) and (13) as one component:

(11)

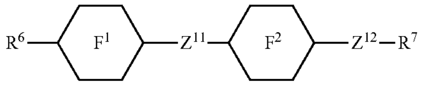

(12)

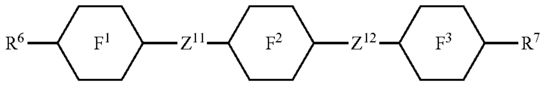

(13)

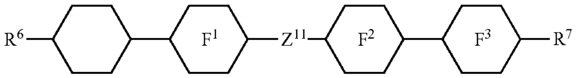

wherein, in the formulas, $R^6$ and $R^7$ are independently alkyl having 1 to 10 carbons or alkenyl having 2 to 10 carbons, and in the alkyl and the alkenyl, arbitrary hydrogen may be replaced by fluorine, and arbitrary may be replaced by —O—; ring $F^1$, ring $F^2$ and ring $F^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{11}$ and $Z^{12}$ are independently —C≡C—, —COO—, $—(CH_2)_2—$, —CH═CH— or a single bond.

12. The liquid crystal composition according to claim 8, further containing at least one compound selected from the group of compounds represented by formula (5):

(5)

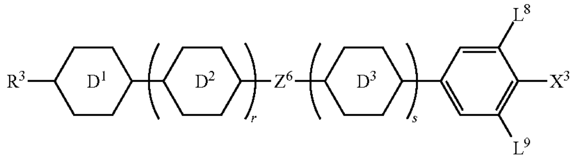

wherein, in formula (5), $R^3$ is alkyl having 1 to 10 carbons or alkenyl having 2 to 10 carbons, and in the alkyl and the alkenyl, arbitrary hydrogen may be replaced by fluorine, and arbitrary $—CH_2—$ may be replaced by —O—; $X^3$ is —C≡N or —C≡C—C≡N; ring $D^1$, ring $D^2$ and ring $D^3$ are independently 1,4-cyclohexylene, 1,4-phenylene, 1,4-phenylene in which arbitrary hydrogen is replaced by fluorine, 1,3-dioxane-2,5-diyl, tetrahydropyran-2,5-diyl, or pyrimidine-2,5-diyl; $Z^6$ is $—(CH_2)_2—$, —COO—, $—CF_2O—$, $—OCF_2—$, —C≡C—, $—CH_2O—$ or a single bond; $L^8$ and $L^9$ are independently hydrogen or fluorine; and r and s are independently 0 or 1.

13. The liquid crystal composition according to claim 8, further containing at least one compound selected from the group of compounds represented by formulas (11), (12) and (13):

(11)

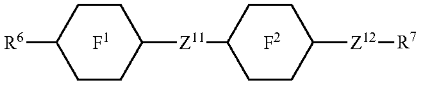

(12)

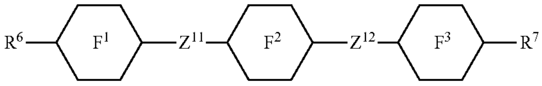

(13)

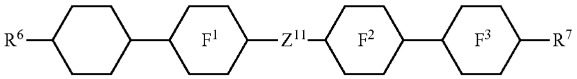

wherein, in the formulas, $R^6$ and $R^7$ are independently alkyl having 1 to 10 carbons or alkenyl having 2 to 10 carbons, and in the alkyl and the alkenyl, arbitrary hydrogen may be replaced by fluorine, and arbitrary $—CH_2—$ may be replaced by —O—; ring $F^1$, ring $F^2$ and ring $F^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{11}$ and $Z^{12}$ are independently —C≡C—, —COO—, $—(CH_2)_2—$, —CH═CH— or a single bond.

14. The liquid crystal composition according to claim 9, further containing at least one compound selected from the group of compounds represented by formulas (11), (12) and (13):

(11)

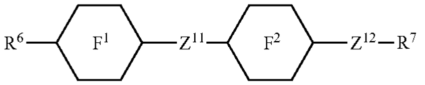

-continued (12)

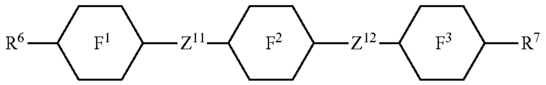

(13)

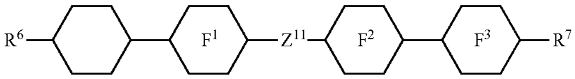

wherein, in the formulas, $R^6$ and $R^7$ are independently alkyl having 1 to 10 carbons or alkenyl having 2 to 10 carbons, and in the alkyl and the alkenyl, arbitrary hydrogen may be replaced by fluorine, and arbitrary $-CH_2-$ may be replaced by $-O-$; ring $F^1$, ring $F^2$ and ring $F^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{11}$ and $Z^{12}$ are independently $-C{\equiv}C-$, $-COO-$, $-(CH_2)_2-$, $-CH{=}CH-$ or a single bond.

15. The liquid crystal composition according to claim 10, further containing at least one compound selected from the group of compounds represented by formulas (11), (12) and (13):

(11)

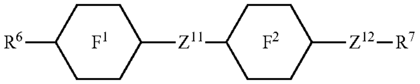

-continued (12)

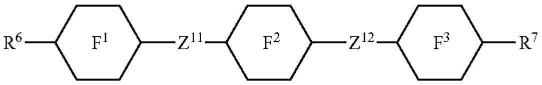

(13)

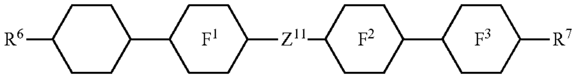

wherein, in the formulas, $R^6$ and $R^7$ are independently alkyl having 1 to 10 carbons or alkenyl having 2 to 10 carbons, and in the alkyl and the alkenyl, arbitrary hydrogen may be replaced by fluorine, and arbitrary $-CH_2-$ may be replaced by $-O-$; ring $F^1$, ring $F^2$ and ring $F^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{11}$ and $Z^{12}$ are independently $-C{\equiv}C-$, $-COO-$, $-(CH_2)_2-$, $-CH{=}CH-$ or a single bond.

16. The liquid crystal composition according to claim 7, further containing at least one optically active compound.

17. The liquid crystal composition according to claim 7, further containing at least one antioxidant and/or at least one ultraviolet light absorber.

18. A liquid crystal display device containing the liquid crystal composition according to claim 7.

* * * * *